(12) United States Patent
Lee et al.

(10) Patent No.: US 6,689,779 B2
(45) Date of Patent: Feb. 10, 2004

(54) OXAZOLIDINONE DERIVATIVES AND A PROCESS FOR THE PREPARATION THEREOF

(75) Inventors: Jae-Gul Lee, Suwon-si (KR); Won-Bin Leem, Yongin-si (KR); Jong-Hwan Cho, Yongin-si (KR); Sung-Hak Choi, Sungnam-si (KR); Jong-Jin Lee, Yongin-si (KR); Sang-Kuk Park, Suwon-si (KR); Tae-Hoo Lee, Yongin-si (KR); Dong-Goo Kim, Suwon-si (KR); Hyun-Jung Sung, Suwon-si (KR)

(73) Assignee: Dong A Pharm. Co., Ltd. (KR)

( * ) Notice: Subject to any disclaimer, the term of this patent is extended or adjusted under 35 U.S.C. 154(b) by 0 days.

(21) Appl. No.: 10/296,896

(22) PCT Filed: May 18, 2001

(86) PCT No.: PCT/KR01/00821

§ 371 (c)(1),
(2), (4) Date: Nov. 27, 2002

(87) PCT Pub. No.: WO01/94342

PCT Pub. Date: Dec. 13, 2001

(65) Prior Publication Data

US 2003/0166620 A1 Sep. 4, 2003

(30) Foreign Application Priority Data

Jun. 5, 2000 (KR) .......................................... 2000-30895
Jun. 5, 2000 (KR) .......................................... 2000-30896
Sep. 23, 2000 (KR) .......................................... 2000-56035
Mar. 7, 2001 (KR) .......................................... 2001-11691

(51) Int. Cl.$^7$ ..................... A61K 31/5377; A61P 31/04; C07D 413/14
(52) U.S. Cl. ..................... 514/235.8; 544/121; 544/131; 544/295; 544/364; 546/194; 546/256; 546/269.4; 546/271.4
(58) Field of Search ................ 544/121, 131, 544/364; 546/271.4; 514/235.8

(56) References Cited

FOREIGN PATENT DOCUMENTS

| WO | WO/93/09103 | 5/1993 |
| WO | WO/93/23384 | 11/1993 |
| WO | WO/95/14684 | 6/1995 |

*Primary Examiner*—Robert W. Ramsuer
(74) *Attorney, Agent, or Firm*—Muserlian, Lucas and Mercanti, LLP

(57) ABSTRACT

The present invention relates to novel oxazolidinone derivatives, their pharmaceutically acceptable salts and a process for the preparation thereof. More particularly, the present invention relates to oxazolidinone derivatives having pyridine or pyrimidine moeity substituted by heterocycle and heteroaromaticcycle at 4-position of phenyl ring. The compounds of the present invention have wide antibacterial spectrum, superior antibacterial activity and low toxicity, such that the compound of this invention can be used as an antibacterial agent.

7 Claims, No Drawings

OXAZOLIDINONE DERIVATIVES AND A PROCESS FOR THE PREPARATION THEREOF

This patent application claims a benefit of priority from Korean Patent Application No. 2000/30895 filed Jun. 5, 2000, Korean Patent Application No. 2000/30896 filed Jun. 5, 2000, Korean Patent Application No. 2000/56035 filed Sep. 23, 2000 and Korean Patent Application No. 2001/11691 filed Mar. 7, 2001; through PCT Application Serial No. PCT/KR01/00821 filed May 18, 2001, the contents of each of which are incorporated herein by reference.

TECHNICAL FIELD

The present invention relates to novel oxazolidinone derivatives of formula 1 with antibacterial activity, their pharmaceutically acceptable salts, and pharmaceutical compositions comprising the same. Also, the present invention is concerned with a method for the preparation thereof.

Formula 1

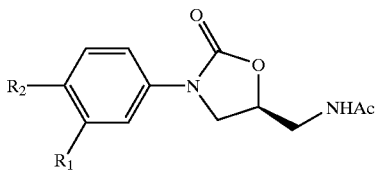

BACKGROUND OF THE INVENTION

Used as orally administrable antibacterial agents, oxazolidinone compounds are not products of fermentation, but artificially synthesized ones, and various structures of their derivatives are known. For instance, 3-phenyl-2-oxazolidinone derivatives having one or two substituents are stated in U.S. Pat. Nos. 4,948,801, 4,461,773, 4,340,606, 4,476,136, 4,250,318 and 4,128,654. 3-[(Monosubstituted) phenyl]-2-oxazolidinone derivatives of formula 2 are disclosed in EP 0312200, J. Med. Chem. 32, 1673(1989), and J. Med. Chem. 33, 2569 (1990), Tetrahedron, 45, 123(1989).

Formula 2

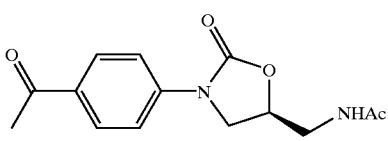

Pharmcia & Upjohn developed oxazolidinone derivatives of formula 3 and 4 (WO 93/23384, WO 95/14684 and WO 95/07271). Having succeeded in gaining the approval of the FDA (Food and Drug Administration) of U.S.A., the oxazolidinone derivatives of formula 3 are going to come into the market. However, these conventional synthetic oxazolidinone compounds was found to suffer from the disadvantage of showing antibacterial activity against a narrow spectrum of bacteria, being toxic to humans, and being poor in therapeutic activity in vivo.

Formula 3

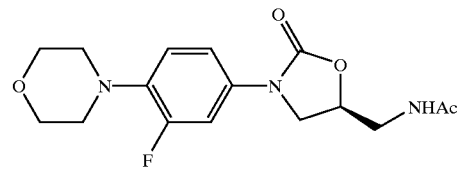

Formula 4

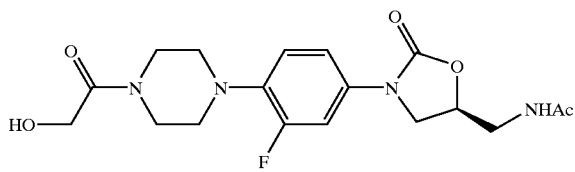

WO 93/09103 discloses oxazolidinone derivatives of formula 1, substituted with heterocyclics such as thiazole, indole, oxazole, and quinole as well as pyridine, at position 4 of the phenyl ring. However, these oxazolidinone derivatives do not provide sufficient medicinal effects because the heterocyclics bear simple substituents such as alkyl or amino groups.

SUMMARY OF THE INVENTION

Leading to the present invention, the intensive and thorough research on oxazolidinone derivatives, conducted by the present inventors aiming to overcome the above problems encountered in prior arts, resulted in the finding that oxazolidinone derivatives substituted with pyridine or pyrimidine derivatives at the 4 position of the phenyl ring have potent antibacterial activity against a broad spectrum of bacteria and their antibacterial activity is maintained high in vivo.

Therefore, it is an object of the present invention to provide oxazolidinone derivatives of formula 1, which potent in inhibitory activity against a broad spectrum of bacteria, and pharmaceutically acceptable salts thereof.

It is another object of the present invention to provide a process for preparing such an oxazolidinone derivative of formula 1, or its pharmaceutically acceptable salt.

It is a further object of the present invention to provide a pharmaceutical composition comprising such an oxazolidinone derivative of formula 1, or its pharmaceutically acceptable salt as a therapeutically effective ingredient.

DETAILED DESCRIPTION OF THE INVENTION

In accordance with an aspect of the present invention, there is provided an oxazolidinone derivative of formula 1:

Formula 1

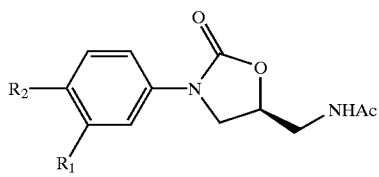

wherein, $R_1$ is H, F, Cl or $CF_3$;

$R_2$ is

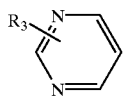 or 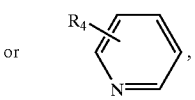, where $R_3$ is
1) H,
2) $C_1$–$C_4$ alkoxy, or piperazinyl optionally substituted with $R_5$,
   where $R_5$ is:
   (a) H;
   (b) Triphenylmethyl;
   (c) substituted or unsubstituted acetyl, provided that the substituted acetyl is selected from the group consisting of benzyloxyacetyl, acetoxyacetyl, hydroxy acetyl, $C_1$–$C_3$ alkylaminoacetoxyacetyl, acetyl substituted with halogen, morpholi-4-nylacetyl, imidazol-1-ylcarbonyloxy acetyl, $C_1$–$C_3$ alkoxycarbonylmethylaminoacetyl, $C_1$–$C_3$ alkoxyacetyl, t-butyl acetyl, phenyl acetyl optionally substituted with $C_1$–$C_3$ alkoxy, and $C_1$–$C_3$ alkoxyoxoacetyl;
   (d) substituted or unsubstituted benzoyl, provided that the substituted benzoyl is selected from the group consisting of $C_1$–$C_4$ selected from the group consisting of $C_1$–$C_4$ alkoxybenzoyl, trihalomethylbenzoyl and nitrobenzoyl;
   (e) substituted or unsubstituted carbonyl, provided that the substituted carbonyl is selected from the group consisting of $C_1$–$C_4$ haloalkylcarbonyl, phenoxycarbony, and benzyloxycarbonyl;
   (f) $C_1$–$C_3$ alkoxyphenyl of;
   (g) acryloyl optionally substituted with $C_1$–$C_3$ alkyl;
   (h) nicotinoyl;
   (i) pivaloyl;
   (j) crotonyl, or
   (k) n-valeryl, $R_4$ is: H; azido; —(C=O)$_l$—$R_6$; —$NR_7R_8$; —$(CH_2)_m$—$R_9$; or —$OR_{10}$,
   wherein $R_6$ is: H; $C_1$–$C_3$ alkoxy; amino; $C_1$–$C_3$ alkylamino; or $C_1$–$C_3$ hydroxyalkylamino,
   l is an integer of 1 or 2,
   $R_7$ and $R_8$, which may be the same or different, represent,
   (a) H;
   (b) $C_1$–$C_4$ alkyl optionally substituted with one or more phenyl groups, or $C_1$–$C_4$ alkenyl substituted with $C_1$–$C_3$ alkylamino;
   (c) substituted or unsubstituted acetyl, provided that the substituted acetyl is selected from the group consisting of acetoxyacetyl, hydroxyacetyl, $C_1$–$C_3$ alkylaminoacetoxyacetyl, $C_1$–$C_3$ alkoxyacetyl, aminoacetyl, azidoacetyl, acetylaminoacetyl, $C_1$–$C_3$ alkylaminoacetyl, aminopropionyl, and hydroxylpropionyl; or
   (d) nicotinoyl,
   $R_9$ is: H; azido; hydroxy; $C_1$–$C_3$ alkylaminoacetoxy; acetylthio, mercapto, cyano, a halogen atom, or a 5- or 6-membered heterocycle,
   m is an integer of 1–4, $R_{10}$ is: H; $C_1$–$C_3$ alkyl; acetyl; alkoxyalkyl; methanesulfonyl; or Heterocylic rings selected from the group consisting of
a) 5- or 6-membered heteroring containing one or more N or O as ring members, preferably represented by the following formula:

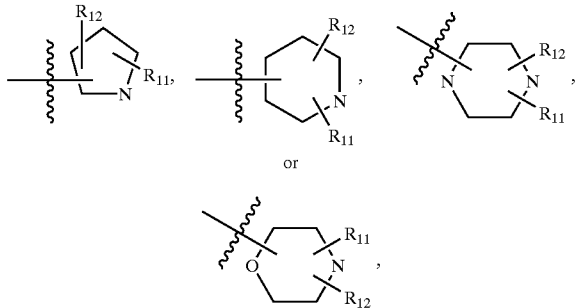

b) a 5-membered heterocyclic ring containing at least one nitrogen or oxygen atom or both of them, as ring members, in which any one carbon atom is saturated with two hydrogen atoms or forms a double bond with oxygen (ketone), nitrogen (imino) or sulfur (thioketone), preferably of the following formula:

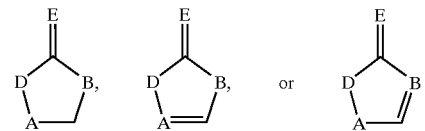

wherein A, B, and D, which may be the same or different, each represents a carbon, an oxygen or a nitrogen atom, and E represents two hydrogen atoms, an oxygen, a sulfur, or a nitrogen atom, and more preferably of the following formula:

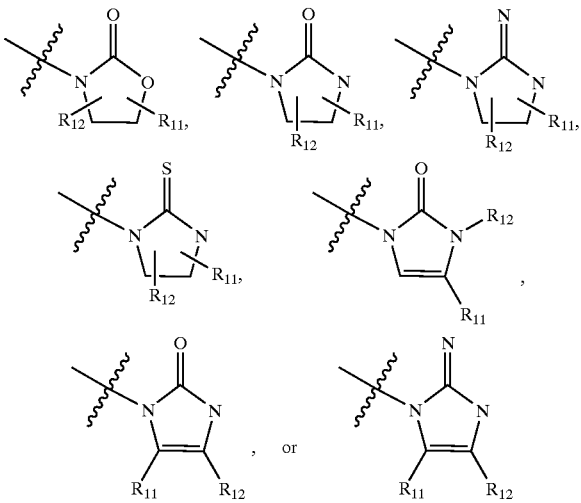

c) 5- or 6-membered hetero aromatic ring containing C, N, O or S as ring members and preferably one or two N or O, or at least one nitrogen and at least one oxygen atom together, as ring members of the following formula:

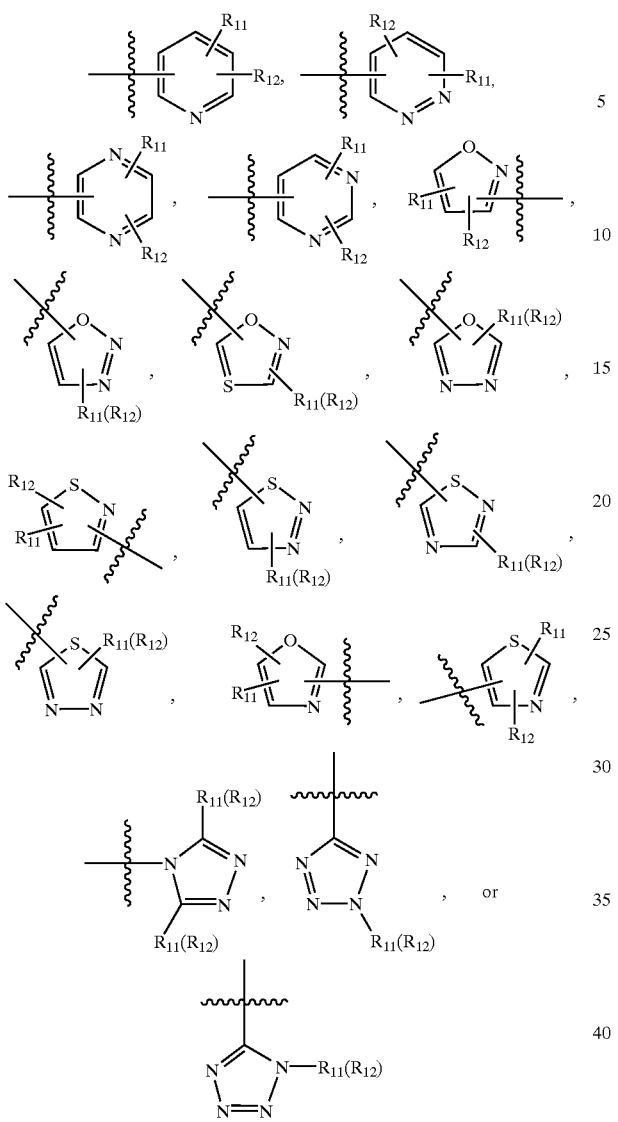

wherein $R_{11}$ and $R_{12}$, which are the same or different, each represents:

(i) H, F, Cl, Br or I;
(ii) $C_1$–$C_4$ alkyl substituted optionally with at least one substituent, provided that the substituted alkyl is selected from the group consisting of hydroxyalkyl, alkoxycarbonylalkyl, trihaloalkyl, acetoxyalkyl, alkylaminoalkyl, alkoxyalkyl, and methanesulfonyloxyalkyl;
(iii) substituted or unsubstituted acetyl, provided that the substituted acetyl is selected from the group consisting of acetoxyacetyl, hydroxyacetyl, $C_1$–$C_3$ alkylamino acetoxyacetyl, $C_1$–$C_3$ alkoxyacetyl, aminoacetyl, azidoacetyl, acetylaminoacetyl, $C_1$–$C_3$ alkylaminoacetyl, aminopropionyl, and hydroxypropionyl;
(iv) azido, hydroxy, mercapto, cyano, ketone, or amino;
(v) substituted or unsubstituted imino, provided that the substituted imino is selected from the group consisting of hydroxyimino, alkylimino, alkoxyimino or methanesulfonyloxyimino;
(vi) hydrozino optionally substituted with alkoxycarbonyl;
(vii) —$OR_{13}$, where $R_{13}$ is H, $C_1$–$C_3$ alkyl, acetyl, alkoxyalkyl, hydroxyacetyl or methanesulfonyl;
(viii) —$NR_{14}R_{15}$, wherein $R_{14}$ and $R_{15}$ represent independently H, $C_1$–$C_3$ alkyl, acetyl, alkoxylalkyl, hydroxyacetyl or methansulfonyl;
(ix) —(C=O)—$(R_{16})_n$—,
wherein $R_{16}$ is:
1) $C_1$–$C_6$ alkyl, or alkenyl optionally substituted with $C_1$–$C_3$ alkyl;
2) alkoxycarbonyl;
3) acetoxymethyl, benzyloxymethyl, hydroxymethyl, $C_1$–$C_3$ alkylacetoxymethyl, halomethyl, $C_1$–$C_3$ alkoxymethyl, morpholinylmethyl, $C_1$–$C_3$ alkoxycarbonylmethyl aminomethyl, $C_1$–$C_3$ methanesulfonyloxymethyl, alkoxyoxomethyl, $C_1$–$C_3$ nicotinoyloxymethyl, alkoxyphenylmethyl, benzyl, or trihalomethyl;
4) $C_1$–$C_3$ alkoxy, phenyloxy, allyloxy, $C_1$–$C_3$ haloalkyloxy, benzyloxy optionally substituted with nitoro, or 9-fluorenylmethyloxy;
5) Nicotinoylmethyl; or
6) a 5- or 6-membered heterocyclic ring Preferable, concrete examples of the compounds of formula 1 include:

1) (S)-[N-3-(4-pyrimidin-5-yl)-3-fluorophenyl]-2-oxo-5-oxazolidinyl]methyl acetamide (compound of Example 1)
2) (S)-[N-3-(4-(2-methoxypyrimidin-5-yl)-3-fluorophenyl)-2-oxo-5-oxazolidinyl]methyl acetamide (compound of Example 2)
3) (S)-[N-3-(4-(2-aminopyrimidin-5-yl)-3-fluorophenyl)-2-oxo-5-oxazolidinyl]methyl acetamide (compound of Example 3)
4) (S)-[N-3-(4-(2-(4-triphenylmethylpiperazin-1-yl)pyrimidin-5-yl)-3-fluorophenyl)-2-oxo-5-oxazolidinyl]methyl acetamide (compound of Example 4)
5) (S)-[N-3-(4-(2-piperazin-1-ylpyrimidin-5-yl)-3-fluorophenyl)-2-oxo-5-oxazolidinyl]methyl acetamide (compound of Example 5)
6) (S)-[N-3-(4-(2-(4-acetylpiperazin-1-yl)pyrimidin-5-yl)-3-fluorophenyl)-2-oxo-5-oxazolidinyl]methyl acetamide (compound of Example 6)
7) (S)-[N-3-(4-(2-(4-benzyloxyacetylpiperazin-1-yl)pyrimidin-5-yl)-3-fluorophenyl)-2-oxo-5-oxazolidinyl]methyl acetamide (compound of Example 7)
8) (S)-[N-3-(4-(2-(4-acetoxyacetylpiperazin-1-yl)pyrimidin-5-yl)-3-fluorophenyl)-2-oxo-5-oxazolidinyl]methyl acetamide (compound of Example 8)
9) (S)-[N-3-(4-(2-(4-hydroxyacetylpiperazin-1-yl)pyrimidin-5-yl)-3-fluorophenyl)-2-oxo-5-oxazolidinyl]methyl acetamide (compound of Example 9)
10) (S)-[N-3-(4-(2-(4-dimethylaminoacetoxyacetylpiperazin-1-yl)pyrimidin-5-yl)-3-fluorophenyl)-2-oxo-5-oxazolidinyl]methyl acetamide (compound of Example 10)
11) (S)-[N-3-(4-(2-(4-bromoacetylpiperazin-1-yl)pyrimidin-5-yl)-3-fluorophenyl)-2-oxo-5-oxazolidinyl]methyl acetamide (compound of Example 11)
12) (S)-[N-3-(4-(2-(4-morpholin-4-ylacetylpiperazin-1-yl)pyrimidin-5-yl)-3-fluorophenyl)-2-oxo-5-oxazolidinyl]methyl acetamide (compound of Example 12)

13) (S)-[N-3-(4-(2-(4-imidazol-1-ylcarbonyloxyacetylpiperazin-1-yl)pyrimidin-5-yl)-3-fluorophenyl)-2-oxo-5-oxazolidinyl]methyl acetamide (compound of Example 13)
14) (S)-[N-3-(4-(2-(4-chloroacetylpiperazin-1-yl)pyrimidin-5-yl)-3-fluorophenyl)-2-oxo-5-oxazolidinyl]methyl acetamide (compound of Example 14)
15) (S)-[N-3-(4-(2-(4-methoxycarbonylmethylaminoacetylpiperazin-1-yl)pyrimidin-5-yl)-3-fluorophenyl)-2-oxo-5-oxazolidiyl]methyl acetamide (compound of Example 15)
16) (S)-[N-3-(4-(2-(4-methoxyphenylpiperazin-4-yl)acetylpiperazin-1-yl)pyrimidin-5-yl)-3-fluorophenyl)-2-oxo-5-oxazolidinyl]methyl acetamide (compound of Example 16)
17) (S)-[N-3-(4-(2-(4-methoxyacetylpiperazin-1-yl)pyrimidin-5-yl)-3-fluorophenyl)-2-oxo-5-oxazolidinyl]methyl acetamide (compound of Example 17)
18) (S)-[N-3-(4-(2-(4-acryloylpiperazin-1-yl)pyrimidin-5-yl)-3-fluorophenyl)-2-oxo-5-oxazolidinyl]methyl acetamide (compound of Example 18)
19) (S)-[N-3-(4-(2-(4-ethoxyoxoacetylpiperazin-1-yl)pyrimidin-5-yl)-3-fluorophenyl)-2-oxo-5-oxazolidinyl]methyl acetamide (compound of Example 19)
20) (S)-[N-3-(4-(2-(4-nicotinoylpiperazin-1-yl)pyrimidin-5-yl)-3-fluorophenyl)-2-oxo-5-oxazolidinyl]methyl acetamide (compound of Example 20)
21) (S)-[N-3-(4-(2-(4-pivaloylpiperazin-1-yl)pyrimidin-5-yl)-3-fluorophenyl)-2-oxo-5-oxazolidinyl]methyl acetamide (compound of Example 21)
22) (S)-[N-3-(4-(2-(4-t-butylacetylpiperazin-1-yl)pyrimidin-5-yl)-3-fluorophenyl)-2-oxo-5-oxazolidinyl]methyl acetamide (compound of Example 22).
23) (S)-[N-3-(4-(2-(4-(2,5-dimethoxyphenyl)acetylpiperazine-1-yl)pyrimidin-5-yl)-3-fluorophenyl)-2-oxo-5-oxazolidinyl]methyl acetamide (compound of Example 23)
24) (S)-[N-3-(4-(2-(4-(3,3-dimethylacryloyl)piperazin-1-yl)pyrimidin-5-yl)-3-fluorophenyl)-2-oxo-5-oxazolidinyl]methyl acetamide (compound of Example 24)
25) (S)-[N-3-(4-(2-(4-(2,6-dimethoxybenzoyl)piperazin-1-yl)pyrimidin-5-yl)-3-fluorophenyl)-2-oxo-5-oxazolidinyl]methyl acetamide (compound of Example 25)
26) (S)-[N-3-(4-(2-(4-(2-trifluoromethylbenzoyl)piperazin-1-yl)pyrimidin-5-yl)-3-fluorophenyl)-2-oxo-5-oxazolidinyl]methyl acetamide (compound of Example-26)
27) (S)-[N-3-(4-(2-(4-(4-trifluoromethylbenzoyl)piperazin-1-yl)pyrimidin-5-yl)-3-fluorophenyl)-2-oxo-5-oxazolidinyl]methyl acetamide (compound of Example 27)
28) (S)-[N-3-(4-(2-(4-phenylacetylpiperazin-1-yl)pyrimidin-5-yl)-3-fluorophenyl)-2-oxo-5-oxazolidinyl]methyl acetamide (compound of Example 28)
29) (S)-[N-3-(4-(2-(4-(3,5-dinitrobenzoyl)piperazin-1-yl)pyrimidin-5-yl)-3-fluorophenyl)-2-oxo-5-oxazolidinyl]methyl acetamide (compound of Example 29)
30) (S)-[N-3-(4-(2-(4-crotonylpiperazin-1-yl)pyrimidin-5-yl)-3-fluorophenyl)-2-oxo-5-oxazolidinyl]methyl acetamide (compound of Example 30)
31) (S)-[N-3-(4-(2-(4-trichloroacetylpiperazin-1-yl)pyrimidin-5-yl)-3-fluorophenyl)-2-oxo-5-oxazolidinyl]methyl acetamide (compound of Example 31)
32) (S)-[N-3-(4-(2-(4-n-valerylpiperazin-1-yl)pyrimidin-5-yl)-3-fluorophenyl)-2-oxo-5-oxazolidinyl]methyl acetamide (compound of Example 32)
33) (S)-[N-3-(4-(2-(4-(1-bromoethylcarbonyl)piperazin-1-yl)pyrimidin-5-yl)-3-fluorophenyl)-2-oxo-5-oxazolidinyl]methyl acetamide (compound of Example 33).
34) (S)-[N-3-(4-(2-(4-phenoxycarbonylpiperazin-1-yl)pyrimidin-5-yl)-3-fluorophenyl)-2-oxo-5-oxazolidinyl]methyl acetamide (compound of Example 34)
35) (S)-[N-3-(4-(2-(4-benzyloxycarbonylpiperazin-1-yl)pyrimidin-5-yl)-3-fluorophenyl)-2-oxo-5-oxazolidinyl]methyl acetamide (compound of Example 35)
36) (S)-[N-3-(4-pyridin-2-yl)-3-fluorophenyl]-2-oxo-5-oxazolidinyl]methyl acetamide (compound of Example 36)
37) (S)-[N-3-(4-(2-aminopyridin-5-yl)-3-fluorophenyl)-2-oxo-5-oxazolidinyl]methyl acetamide (compound of Example 37)
38) (S)-[N-3-(4-(3-methoxycarbonylpyridin-5-yl)-3-fluorophenyl)-2-oxo-5-oxazolidinyl]methyl acetamide (compound of Example 38)
39) (S)-[N-3-(4-(2-acetylaminopyridin-5-yl)-3-fluorophenyl)-?-oxo-5-oxazolidinyl]methyl acetamide (compound of Example 39)
40) (S)-[N-3-(4-(2-acetoxyacetylaminopyridin-5-yl)-3-fluorophenyl)-2-oxo-5-oxazolidinyl]methyl acetamide (compound of Example 40)
41) (S)-[N-3-(4-(2-hydroxyacetylaminopyridin-5-yl)-3-fluorophenyl)-2-oxo-5-oxazolidinyl]methyl acetamide (compound of Example 41)
42) (S)-[N-3-(4-(2-imidazol-1-yl-pyridin-5-yl)-3-fluorophenyl)-2-oxo-5-oxazolidinyl]methyl acetamide (compound of Example 42)
43) (S)-[N-3-(4-(2-morpholin-4-yl-pyridin-5-yl)-3-fluorophenyl)-2-oxo-5-oxazolidinyl]methyl acetamide (compound of Example 43)
44) (S)-[N-3-(4-(2-triphenylmethylaminopyridin-5-yl)-3-fluorophenyl)-2-oxo-5-oxazolidinyl]methyl acetamide (compound of Example 44)
45) (S)-[N-3-(4-(2-methoxypyridin-5-yl)-3-fluorophenyl)-2-oxo-5-oxazolidinyl]methyl acetamide (compound of Example 45)
46) (S)-[N-3-(4-(2-methoxyacetylaminopyridin-5-yl)-3-fluorophenyl)-2-oxo-5-oxazolidinyl]methyl acetamide (compound of Example 46)
47) (S)-[N-3-(4-(2-(4-triphenylmethylpiperazin-1-yl)pyridin-5-yl)-3-fluorophenyl)-2-oxo-5-oxazolidinyl]methyl acetamide (compound of Example 47)
48) (S)-[N-3-(4-(2-triphenylmethylaminopyridin-5-yl)-3-fluorophenyl)-2-oxo-5-oxazolidinyl]methyl acetamide (compound of Example 48)
49) (S)-[N-3-(4-(2-azidopyridin-5-yl)-3-fluorophenyl)-2-oxo-5-oxazolidinyl]methyl acetamide (compound of Example 49)

50) (S)-[N-3-(4-(2-hydroxymethylpyridin-4-yl)-3-fluorophenyl)-2-oxo-5-oxazolidinyl]methyl acetamide (compound of Example 50)
51) (S)-[N-3-(4-(2-methoxycarbonylpyridin-4-yl)-3-fluorophenyl)-2-oxo-5-oxazolidinyl]methyl acetamide (compound of Example 51)
52) (S)-[N-3-(4-(2-dimethylaminocarbonylpyridin-4-yl)-3-fluorophenyl)-2-oxo-5-oxazolidinyl]methyl acetamide (compound of Example 52)
53) (S)-[N-3-(4-(2-hydroxypyridin-5-yl)-3-fluorophenyl)-2-oxo-5-oxazolidinyl]methyl acetamide (compound of Example 53)
54) (S)-[N-3-(4-(N-2-dimethylaminoacetoxyacetylaminopyridin-4-yl)-3-fluorophenyl)-2-oxo-5-oxazolidinyl]methyl acetamide (compound of Example 54)
55) (S)-[N-3-(4-(2-methylaminopyridin-4-yl)-3-fluorophenyl)-2-oxo-5-oxazolidinyl]methyl acetamide (compound of Example 55)
56) (S)-[N-3-(4-(2-dimethylaminopyridin-4-yl)-3-fluorophenyl)-2-oxo-5-oxazolidinyl]methyl acetamide (compound of Example 56)
57) (S)-[N-3-(4-(2-hydroxyacetylaminopyridin-5-yl)-3-fluorophenyl)-2-oxo-5-oxazolidinyl]methyl acetamide
65) (S)-[N-3-(4-(2-N,N-di(2-hydroxyethyl)aminocarbonylpyridin-4-yl)-3-fluorophenyl)-2-oxo-5-oxazolidinyl]methyl acetamide (compound of Example 65)
66) (S)-[N-3-(4-(2-piperazin-1-ylpyridin-5-yl)-3-fluorophenyl)-2-oxo-5-oxazolidinyl]methyl acetamide (compound of Example 66)
67) (S)-[N-3-(4-(2-(4-acetoxyacetylpiperazin-1-yl)pyridin-5-yl)-3-fluorophenyl)-2-oxo-5-oxazolidinyl]methyl acetamide (compound of Example 67)
68) (S)-[N-3-(4-(2-(4-benzyloxyacetylpiperazin-1-yl)pyridin-5-yl)-3-fluorophenyl)-2-oxo-5-oxazolidinyl]methyl acetamide (compound of Example 68)
69) (S)-[N-3-(4-(2-(4-hydroxyacetylpiperazin-1-yl)pyridin-5-yl)-3-fluorophenyl)-2-oxo-5-oxazolidinyl]methyl acetamide (compound of Example 69)
70) (S)-[N-3-(4-(2-(4-dimethylaminoacetoxyacetylpiperazin-1-yl)pyridin-5-yl)-3-fluorophenyl)-2-oxo-5-oxazolidinyl]methyl acetamide (compound of Example 70)
71) (S)-[N-3-(4-(2-(4-chloroacetylpiperazin-1-yl)pyridin-5-yl)-3-fluorophenyl)-2-oxo-5-oxazolidinyl]methyl acetamide (compound of Example 71)
65) (S)-[N-3-(4-(2-N,N-di(2-hydroxyethyl)aminocarbonylpyridin-4-yl)-3-fluorophenyl)-2-oxo-5-oxazolidinyl]methyl acetamide (compound of Example 65)
66) (S)-[N-3-(4-(2-piperazin-1-ylpyridin-5-yl)-3-fluorophenyl)-2-oxo-5-oxazolidinyl]methyl acetamide (compound of Example 66)
67) (S)-[N-3-(4-(2-(4-acetoxyacetylpiperazin-1-yl)pyridin-5-yl)-3-fluorophenyl)-2-oxo-5-oxazolidinyl]methyl acetamide (compound of Example 67)
68) (S)-[N-3-(4-(2-(4-benzyloxyacetylpiperazin-1-yl)pyridin-5-yl)-3-fluorophenyl)-2-oxo-5-oxazolidinyl]methyl acetamide (compound of Example 68)
69) (S)-[N-3-(4-(2-(4-hydroxyacetylpiperazin-1-yl)pyridin-5-yl)-3-fluorophenyl)-2-oxo-5-oxazolidinyl]methyl acetamide (compound of Example 69)
70) (S)-[N-3-(4-(2-(4-dimethylaminoacetoxyacetylpiperazin-1-yl)pyridin-5-yl)-3-fluorophenyl)-2-oxo-5-oxazolidinyl]methyl acetamide (compound of Example 70)
71) (S)-[N-3-(4-(2-(4-chloroacetylpiperazin-1-yl)pyridin-5-yl)-3-fluorophenyl)-2-oxo-5-oxazolidinyl]methyl acetamide (compound of Example 71)
72) (S)-[N-3-(4-(2-(4-acetylpiperazin-1-yl)pyridin-5-yl)-3-fluorophenyl)-2-oxo-5-oxazolidinyl]methyl acetamide (compound of Example 72)
73) (S)-[N-3-(4-(2-(4-methoxyacetylpiperazin-1-yl)pyridin-5-yl)-3-fluorophenyl)-2-oxo-5-oxazolidinyl]methyl acetamide (compound of Example 73)
74) (S)-[N-3-(4-(2-(4-morpholinylacetylpiperazin-1-yl)pyridin-5-yl)-3-fluorophenyl)-2-oxo-5-oxazolidinyl]methyl acetamide (compound of Example 74)
75) (S)-[N-3-(4-(2-(4-methoxycarbonylmethylaminoacetylpiperazin-1-yl)pyridin-5-yl)-3-fluorophenyl)-2-oxo-5-oxazolidinyl]methyl acetamide (compound of Example 75)
76) (S)-[N-3-(4-(2-(4-ethoxycarbonylpiperidin-1-yl)pyridin-5-yl)-3-fluorophenyl)-2-oxo-5-oxazolidinyl]methyl acetamide (compound of Example 76)
77) (S)-[N-3-(4-(2-azidomethylpyridin-4-yl)-3-fluorophenyl)-2-oxo-5-oxazolidinyl]methyl acetamide (compound of Example 77)
78) (S)-[N-3-(4-(2-imidazol-1-yl)methylpyridin-4-yl)-3-fluorophenyl]-2-oxo-5-oxazolidinyl]methyl acetamide (compound of Example 78)
79) (S)-[N-3-(4-(2-morpholin-4-yl)methylpyridin-4-yl)-3-fluorophenyl)-2-oxo-5-oxazolidinyl]methyl acetamide (compound of Example 79)
80) (S)-[N-3-(4-(2-acetylthiomethylpyridin-4-yl)-3-fluorophenyl)-2-oxo-5-oxazolidinyl]methyl acetamide (compound of Example 80)
81) (S)-[N-3-(4-(2-mercaptomethylpyridin-4-yl)-3-fluorophenyl)-2-oxo-5-oxazolidinyl]methyl acetamide (compound of Example 81)
82) (S)-[N-3-(4-(2-(4-methanesulfonyloxyacetylpiperazin-1-yl)pyridin-5-yl)-3-fluorophenyl)-2-oxo-5-oxazolidinyl]methyl acetamide (compound of Example 82)
83) (S)-[N-3-(4-(2-(4-acryloylpiperazin-1-yl)pyridin-5-yl)-3-fluorophenyl)-2-oxo-5-oxazolidinyl]methyl acetamide (compound of Example 83)
84) (S)-[N-3-(4-(2-(4-ethoxyoxoacetylpiperazin-1-yl)pyridin-1-yl)-3-fluorophenyl)-2-oxo-5-oxazolidinyl]methyl acetamide (compound of Example 84)
85) (S)-[N-3-(4-(2-(4-nicotinoylpiperazin-1-yl)pyridin-5-yl)-3-fluorophenyl)-2-oxo-5-oxazolidinyl]methyl acetamide (compound of Example 85)
86) (S)-[N-3-(4-(2-(4-pivaloylpiperazin-1-yl)pyridin-5-yl)-3-fluorophenyl)-2-oxo-5-oxazolidinyl]methyl acetamide (compound of Example 86)
87) (S)-[N-3-(4-(2-(4-tetrabutylacetylpiperazin-1-yl)pyridin-5-yl)-3-fluorophenyl)-2-oxo-5-oxazolidinyl]methyl acetamide (compound of Example 87)
88) (S)-[N-3-(4-(2-(4-nicotinoyloxyacetylpiperazin-1-yl)pyridin-5-yl)-3-fluorophenyl)-2-oxo-5-oxazolidinyl]methyl acetamide (compound of Example 88)
89) (S)-[N-3-(4-(2-(4-(2,5-dimethoxyphenylacetyl)piperazin-1-yl)pyridin-5-yl)-3-fluorophenyl)-2-oxo-5-oxazolidinyl]methyl acetamide (compound of Example 89)
90) (S)-[N-3-(4-(2-(4-(3,3-dimethylacryloyl)piperazin-1-yl)pyridin-5-yl)-3-fluorophenyl)-2-oxo-5-oxazolidinyl]methyl acetamide (compound of Example 90)

91) (S)-[N-3-(4-(2-(4-(2,6-dimethoxybenzoyl)piperazin-1-yl)pyridin-5-yl)-3-fluorophenyl)-2-oxo-5-oxazolidinyl]methyl acetamide (compound of Example 91)
92) (S)-[N-3-(4-(2-(4-(2-trifluoromethyl)benzoyl)piperazin-1-yl)pyridin-5-yl)-3-fluorophenyl]-2-oxo-5-oxazolidinyl]methyl acetamide (compound of Example 92)
93) (S)-[N-3-(4-(2-(4-(4-trifluoromethyl)benzoyl)piperazin-1-yl)pyridin-5-yl)-3-fluorophenyl]-2-oxo-5-oxazolidinyl]methyl acetamide (compound of Example 93)
94) (S)-[N-3-(4-(2-(4-benzylcarbonylpiperazin-1-yl)pyridin-5-yl)-3-fluorophenyl)-2-oxo-5-oxazolidinyl] methyl acetamide (compound of Example 94)
95) (S)-[N-3-(4-(2-(4-crotonylpiperazin-1-yl)pyridin-5-yl)-3-fluorophenyl)-2-oxo-5-oxazolidinyl]methyl acetamide (compound of Example 95)
96) (S)-[N-3-(4-(2-(4-trifluoromethylcarbonylpiperazin-1-yl)pyridin-5-yl)-3-fluorophenyl)-2-oxo-5-oxazolidinyl]methyl acetamide (compound of Example 96)
97) (S)-[N-3-(4-(2-(4-n-valerylpiperazin-1-yl)pyridin-5-yl)-3-fluorophenyl)-2-oxo-5-oxazolidinyl]methyl acetamide (compound of Example 97)
98) (S)-[N-3-(4-(2-(4-phenyloxycarbonylpiperazin-1-yl)pyridin-5-yl)-3-fluorophenyl)-2-oxo-5-oxazolidinyl] methyl acetamide (compound of Example 98)
99) (S)-[N-3-(4-(2-(4-allyloxycarbonylpiperazin-1-yl)pyridin-5-yl)-3-fluorophenyl)-2-oxo-5-oxazolidinyl] methyl acetamide (compound of Example 99)
100) (S)-[N-3-(4-(2-(4-(1-chloroethy)oxycarbonylpiperazin-1-yl)pyridin-5-yl)-3-fluorophenyl)-2-oxo-5-oxazolidinyl]methyl acetamide (compound of Example 100)
101) (S)-[N-3-(4-(2-(4-(4-nitrobenzyl)oxycarbonylpiperazin-1-yl)pyridin-5-yl)-3-fluorophenyl)-2-oxo-5-oxazolidinyl]methyl acetamide (compound of Example 101)
102) (S)-[N-3-(4-(2-(4-benzyloxycarbonylpiperazin-1-yl)pyridin-5-yl)-3-fluorophenyl)-2-oxo-5-oxazolidinyl] methyl acetamide (compound of Example 102)
103) (S)-[N-3-(4-(2-(4-(9-fluorenylmethyloxycarbonyl)piperazin-1-yl)pyridin-5-yl)-3-fluorophenyl)-2-oxo-5-oxazoldinyl]methyl acetamide (compound of Example 103)
104) (S)-[N-3-(4-(2-(4-(2-pyrimidinyl)piperazin-1-yl)pyridin-5-yl)-3-fluorophenyl)-2-oxo-5-oxazolidinyl] methyl acetamide (compound of Example 104)
105) (S)-[N-3-(4-(2-(4-methoxycarbonylmethylpiperazin-1-yl)pyridin-5-yl)-3-fluorophenyl)-2-oxo-5-oxazolidinyl]methyl acetamide (compound of Example 105)
106) (S)-[N-3-(4-(2-fluoromethylpyridin-4-yl)-3-fluorophenyl)-2-oxo-5-oxazolidinyl]methyl acetamide (compound of Example 106)
107) (S)-[N-3-(4-(2-cyanomethylpyridin-4-yl)-3-fluorophenyl)-2-oxo-5-oxazolidinyl]methyl acetamide (compound of Example 107)
108) (S)-[N-3-(4-(2-methylpyridin-4-yl)-3-fluorophenyl)-2-oxo-5-oxazolidinyl]methyl acetamide (compound of Example 108)
109) (S)-[N-3-(4-(2-(4-(2-hydroxy)ethylpiperazin-1-yl)pyridin-5-yl)-3-fluorophenyl)-2-oxo-5-oxazolidinyl] methyl acetamide (compound of Example 109)
110) (S)-[N-3-(4-(2-(4-(2-acetoxy)ethylpiperazin-1-yl)pyridin-5-yl)-3-fluorophenyl)-2-oxo-5-oxazolidinyl] methyl acetamide (compound of Example 110)
111) (S)-[N-3-(4-(2-(4-methoxycarbonylpiperazin-1-yl)pyridin-5-yl)-3-fluorophenyl)-2-oxo-5-oxazolidinyl] methylacetamide (compound of Example 111)
112) (S)-[N-3-(4-(2-(4-(2-methanesulfonyloxy)ethylpiperazin-1-yl)pyridin-5-yl)-3-fluorophenyl)-2-oxo-5-oxazolidinyl]methyl acetamide (compound of Example 112)
113) (S)-[N-3-(4-(2-(4-(4-hydroxymethyl)imidazol-1-yl)pyridin-5-yl)-3-fluorophenyl)-2-oxo-5-oxazolidinyl] methyl acetamide (compound of Example 113)
114) (S)-[N-3-(4-(2-aminoacetylaminopyridin-5-yl)-3-fluorophenyl)-2-oxo-5-oxazolidinyl]methyl acetamide (compound of Example 114)
115) (S)-[N-3-(4-(2-(4-cyanopiperazin-1-yl)pyridin-5-yl)-3-fluorophenyl)-2-oxo-5-oxazolidinyl]methyl acetamide (compound of Example 115)
116) (S)-[N-3-(4-(2-(4-carboxamideoximpiperazin-1-yl)pyridin-5-yl)-3-fluorophenyl)-2-oxo-5-oxazolidinyl] methyl acetamide (compound of Example 116)
117) (S)-[N-3-(4-(2-(4-oxopiperidin-1-yl)pyridin-5-yl)-3-fluorophenyl)-2-oxo-5-oxazolidinyl]methyl acetamide (compound of Example 117)
118) (S)-[N-3-(4-(2-azidoacetylaminopyridin-5-yl)-3-fluorophenyl)-2-oxo-5-oxazolidinyl]methyl acetamide (compound of Example 118)
119) (S)-[N-3-(4-(2-(1,2,3,4,6,7-hexahydro-5-oxo-1,4-diazepan-1-yl)-pyridin-5-yl)-3-fluorophenyl)-2-oxo-5-oxazolidinyl]methyl acetamide (compound of Example 119)
120) (S)-[N-3-(4-(2-N-(dimethylaminomethylene)aminopyridin-5-yl)-3-fluorophenyl)-2-oxo-5-oxazolidinyl]methyl acetamide (compound of Example 120)
121) (S)-[N-3-(4-(2-(4-hydroxyiminopiperidin-1-yl)pyridin-5-yl)-3-fluorophenyl)-2-oxo-5-oxazolidinyl] methyl acetamide (compound of Example 121)
122) (s)-[N-3-(4-(2-(4-methanesulfonyloxyiminopiperidin-1-yl)pyridin-5-yl)-3-fluorophenyl)-2-oxo-5-oxazolidinyl]methyl acetamide (compound of Example 122)
123) (S)-[N-3-(4-(2-(4-methyliminopiperidin-1-yl)pyridin-5-yl)-3-fluorophenyl)-2-oxo-5-oxazolidinyl] methyl acetamide (compound of Example 123)
124) (S)-[N-3-(4-(2-(4-methoxycarbonylhydrazino piperidin-1-yl)pyridin-5-yl)-3-fluorophenyl)-2-oxo-5-oxazolidinyl]methyl acetamide (compound of Example 124)
125) (S)-[N-3-(4-(2-N-(L-alanyl)aminopyridin-5-yl)-3-fluorophenyl)-2-oxo-5-oxazolidinyl]methyl acetamide (compound of Example 125)
126) (S)-[N-3-(4-(2-acetylaminoacetylaminopyridin-5-yl)-3-fluorophenyl)-2-oxo-5-oxazolidinyl]methyl acetamide (compound of Example 126)
127) (S)-[N-3-(4-(2-dimethylaminoacetylaminopyridin-5-yl)-3-fluorophenyl)-2-oxo-5-oxazolidinyl]methyl acetamide (compound of Example 127)
128) (S)-[N-3-(4-(2-nicotinoylaminopyridin-5-yl)-3-fluorophenyl)-2-oxo-5-oxazolidinyl]methyl acetamide (compound of Example 128)
129) (S)-[N-3-(4-(2-(1,2,4-triazol-1-yl)pyridin-5-yl)-3-fluorophenyl)-2-oxo-5-oxazolidinyl]methyl acetamide (compound of Example 129)

130) (S)-[N-3-(4-(2-(4-hydroxypiperidin-1-yl)pyridin-5-yl)-3-fluorophenyl)-2-oxo-5-oxazolidinyl]methyl acetamide (compound of Example 130)
131) (S)-[N-3-(4-(2-N,N-(hydroxyacetyl)methylaminopyridin-5-yl)-3-fluorophenyl)-2-oxo-5-oxazolidinyl]methyl acetamide (compound of Example 131)
132) (S)-[N-3-(4-(2-(4-methylimidazol-1-yl)pyridin-5-yl)-3-fluorophenyl)-2-oxo-5-oxazolidinyl]methyl acetamide (compound of Example 132)
133) (S)-[N-3-(4-(2-(2-hydroxypropionyl)aminopyridin-5-yl)-3-fluorophenyl)-2-oxo-5-oxazolidinyl]methyl acetamide (compound of Example 133)
134) (S)-[N-3-(4-(2-(3-amino-1,2,4-triazol-1-yl)pyridin-5-yl)-3-fluorophenyl)-2-oxo-5-oxazolidinyl]methyl acetamide (compound of Example 134)
135) (S)-[N-3-(4-(2-(4-ethoxycarbonylimidazol-1-yl)pyridin-5-yl)-3-fluorophenyl)-2-oxo-5-oxazolidinyl]methyl acetamide (compound of Example 135)
136) (S)-(N-3-(4-(2-(1-tetrazolyl)-pyridin-5-yl)-3-fluorophenyl)-2-oxo-5-oxazolidinyl)methyl acetamide (compound of Example 136)
137) (S)-[N-3-(4-(2-(5-methyl-(1,3,4)-oxadiazol-2-yl)-pyridin-5-yl)-3-fluorophenyl)-2-oxo-5-oxazolidinyl]methyl acetamide (compound of Example 137)
138) (S)-[N-3-(4-(2-(5-methyl-(1,2,4)-oxadiazol-3-yl)pyridin-5-yl)-3-fluorophenyl)-2-oxo-5-oxazolidinyl]methyl acetamide (compound of Example 138)
139) (S)-[N-3-(4-(2-(1-methyl-5-tetrazolyl)-pyridin-5-yl)-3-fluorophenyl)-2-oxo-5-oxazolidinyl]methyl acetamide (compound of Example 139)
140) (S)-[N-3-(4-(2-(2-methyl-5-tetrazolyl)-pyridin-5-yl)-3-fluorophenyl)-2-oxo-5-oxazolidinyl]methyl acetamide (compound of Example 140)
141) (S)-[N-3-(4-(2-(4-ethoxycarbonyl-(1,2,3)-triazol-1-yl)-5-pyridinyl)-3-fluorophenyl)-2-oxo-5-oxazolidinyl]methyl acetamide (compound of Example 141)
142) (S)-[N-3-(4-(2-(3-pyrrolynyl)-5-pyridinyl)-3-fluorophenyl)-2-oxo-5-oxazolidinyl]methyl acetamide (compound of Example 142)
143) (S)-[N-3-(4-(2-(2-oxo-(1,3)-oxazolidin-3-yl)-pyridin-5-yl)-3-fluorophenyl)-2-oxo-5-oxazolidinyl]methyl acetamide (compound of Example 143)
144) (S)-[N-3-(4-(2-((1,3)-oxazol-5-yl)-pyridin-5-yl)-3-fluorophenyl)-2-oxo-5-oxazolidinyl]methyl acetamide (compound of Example 144)
145) (S)-[N-3-(4-(2-((1,2,4)-oxadiazol-3-yl)-pyridin-5-yl)-3-fluorophenyl)-2-oxo-5-oxazolidinyl]methyl acetamide (compound of Example 145)
146) (S)-[N-3-(4-(2-((1,2,3)-triazol-1-yl)-pyridin-5-yl)-3-fluorophenyl)-2-oxo-5-oxazolidinyl]methyl acetamide (compound of Example 146)
147) (S)-[N-3-(4-(2-(3-methyl-2-oxo-2,3-dihydro-(1,3,4)-triazol-1-yl)-5-pyridinyl)-3-fluorophenyl)-2-oxo-5-oxazolidinyl]methyl acetamide (compound of Example 147)
148) (S)-[N-3-(4-(2-(2-oxo-(1,3)-imidazolidin-1-yl)-pyridin-5-yl)-3-fluorophenyl)-2-oxo-5-oxazolidinyl]methyl acetamide (compound of Example 148)
149) (S)-[N-3-(4-(2-(4-hydroxy-piperidin-1-yl)-5-pyridinyl)-3-fluorophenyl)-2-oxo-5-oxazolidinyl]methyl acetamide (compound of Example 149)
150) (S)-[N-3-(4-(2-(2-oxo-(2,3)-dihydro-(1,3,4)-triazol-1-yl)-5-pyridinyl)-3-fluorophenyl)-2-oxo-5-oxazolidinyl]methyl acetamide (compound of Example 150)
151) (S)-[N-3-(4-(2-(5-hydroxymethyl-(1,2,4)-oxadiazol-3-yl)-5-pyridinyl)-3-fluorophenyl)-2-oxo-5-oxazolidinyl]methyl acetamide (compound of Example 151)
152) (S)-[N-3-(4-(2-(5-tetrazolyl)-5-pyridinyl)-3-fluorophenyl)-2-oxo-5-oxazolidinyl]methyl acetamide (compound of Example 152)
153) (S)-[N-3-(4-(2-(5-methoxymethyl-(1,2,4)-oxadiazol-3-yl)-5-pyridinyl)-3-fluorophenyl)-2-oxo-5-oxazolidinyl]methyl acetamide (compound of Example 153)
154) (S)-[N-3-(4-(2-(5-trichloromethyl-(1,2,4)-oxadiazol-3-yl)-5-pyridinyl)-3-fluorophenyl)-2-oxo-5-oxazolidinyl]methyl acetamide (compound of Example 154)
155) (S)-[N-3-(4-(2-(5-dimethylamino-(1,2,4)-oxadiazol-3-yl)-5-pyridinyl)-3-fluorophenyl)-2-oxo-5-oxazolidinyl]methyl acetamide (compound of Example 155)
156) (S)-[N-3-(4-(2-(5-amino-(1,2,4)-oxadiazol-3-yl)-pyridin-5-yl)-3-fluorophenyl)-2-oxo-5-oxazolidinyl]methyl acetamide (compound of Example 156)
157) (S)-[N-3-(4-(2-(4-acetylamino-1-piperidinyl)-pyridin-5-yl)-3-fluorophenyl)-2-oxo-5-oxazolidinyl]methyl acetamide (compound of Example 157)
158) (S)-[N-3-(4-(2-(4-acetyloxymethylcarbonylamino-piperidin-1-yl)-pyridin-5-yl)-3-fluorophenyl)-2-oxo-5-oxazolidinyl]methyl acetamide (compound of Example 158)
159) (S)-[N-3-(4-(2-(4-hydroxymethylcarbonylamino-piperidin-1-yl)-pyridin-5-yl)-3-fluorophenyl)-2-oxo-5-oxazolidinyl]methyl acetamide (compound of Example 159)
160) (S)-[N-3-(4-(2-(3,4-dihydroxy-pyrrolidin-1-yl)-pyridin-5-yl)-3-fluorophenyl)-2-oxo-5-oxazolidinyl]methyl acetamide (compound of Example 160).

More preferable examples of the compounds of formula 1 include;

1) (S)-[N-3-(4-(2-(1,2,4-triazol-1-yl)pyridin-5-yl)-3-fluorophenyl)-2-oxo-5-oxazolidinyl]methyl acetamide (compound of Example 129),
2) (S)-[N-3-(4-(2-(5-methyl-(1,3,4)-oxadiazol-2-yl)-pyridin-5-yl)3-fluorophenyl)-2-oxo-5-oxazolidinyl]methyl acetamide (compound of Example 137),
3) (S)-[N-3-(4-(2-(5-methyl-1,2,4-oxadiazol-3-yl)-pyridin-5-yl)-3-fluorophenyl)-2-oxo-5-oxazolidinyl]methyl acetamide (compound of Example 138),
4) (S)-[N-3-(4-(2-(1-methyl-5-tetrazolyl)-pyridin-5-yl)-3-fluorophenyl)-2-oxo-5-oxazolidinyl]methyl acetamide (compound of Example 139), and
5) (S)-[N-3-(4-(2-oxo-(1,3)-oxazolidin-3-yl)-pyridin-5-yl)-3-fluorophenyl]-2-oxo-5-oxazolidinyl]methyl acetamide (compound of Example 143).

As for the pharmaceutically acceptable salt, it is preferably an acid addition salt prepared by use of a pharmaceutically acceptable free acid. Whether it is inorganic or organic, a free acid can be used if it is pharmaceutically acceptable. Examples of the inorganic free acid include hydrochloric acid, bromic acid, sulfuric acid, and phosphoric acid. Available organic free acids are exemplified by citric acid, acetic acid, lactic acid, tartaric acid, maleic acid, fumaric acid, gluconic acid, methane sulfonic acid, glyconic acid, succinic acid, 4-toluenesulfonic acid, galuturonic acid, embonic acid, glutamic acid, and aspartic acid.

In addition, the pharmaceutically acceptable salt of the compound of formula 1 can be prepared using a base.

Available is pharmaceutically acceptable metals, especially alkaline metal. Examples of useful metal include sodium and potassium.

In accordance with another aspect of the present invention, there is provided a method for preparing an oxazolidinone derivative of formula 1. As se en in the following Scheme 1, the preparation of the oxazolidinone derivative is achieved by reacting a triyethylstanyl oxazolidinone derivative 2 with a pyridine derivative 3 in the presence of a palladium catalyst.

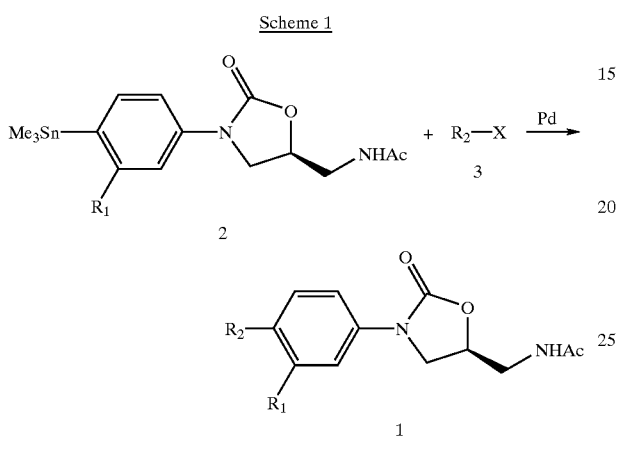

(wherein $R_1$, $R_2$ and X are each as defined above).

A detailed reaction route for the preparation of the oxazolidinone derivative of the present invention is illustrated in the following Scheme 2. As shown, the oxazolidinone derivative is prepared by:

a) aminating a hydroxymethyloxazolidinone derivative 4 at its hydroxy group to give an amine compound 5 (step 1), b) acetylating the amine compound 5 by use of acetic anhydride to produce an acetyl compound 6 (step 2), c) halogenating the acetyl compound 6 at its phenyl ring to produce a halogen compound 7 (step 3);

d) stannylating the halogen compound 7 in the presence of a palladium catalyst to give a trimethylstannyl oxazolidinone derivative 2 (step 4), and e) substituting the trimetyistannyl group of the oxazolidinone derivative 2 with a pyridine or pyrimidine moiety in the presence of a palladium catalyst to yield a compound 1 (step 5).

Scheme 2

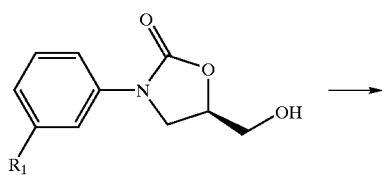

wherein $R_1$ and $R_2$ are as defined above, and X is a halogen atom.

Below, a detail description will be stepwise given of the method for preparing oxazolidinone derivatives of the present invention The hydroxymethyl oxazolidinone derivative of formula 4, used as the starting material in Scheme 4, can be readily synthesized by well-known processes. For example, a benzyloxycarbonyl group is introduced into the amine group of aniline and then reacted with glycidylbutyrate in the presence of a strong base to obtain the starting material. Examples of the strong base suitable for use in this synthesis include n-butyl lithium, sec-butyl lithium and tert-butyl lithium with preference for n-butyl lithium. The synthesis is preferably carried out at −78° C.

In the step 1, the hydroxy group of the hydroxymethyloxazolidinone derivative 4 is converted into an amine group. In this regard, a leaving group is first attached to the hydroxy group for the introduction of an azide group which is then reduced into an amine group.

Suitable as the leaving group are methane sulfonyl, para-toluene sulfonyl, and halogen. Preferably, the attachment of the leaving group is conducted at 0° C.

Because azide is a good nucleophile, the leaving group, such as methane sulfonyl, para-toluene sulfonyl or halogen, can be readily substituted by azide through nucleophilic displacement. For this reaction, sodium azide is used in an amount of about 1 to 3 equivalents relative to the methyloxazolidinone derivative reactant. The nuclegophilic displacement is preferably carried out 80 to 110° C. for 1 to 2 hours in a solvent, which is exemplified by dimethylformamide, dimethylsulfoxide and 1,4-dioxane.

Next, reduction of the resulting azide provides the primary amine of formula 5. This reduction is achieved by catalytic hydrogenation or by use of triphenyl phosphine. As for the catalytic hydrogenation, it is preferably carried out at room temperature under a hydrogen atmosphere using palladium in a solvent selected from the group consisting of tetrahydrofuran, methanol and mixtures thereof. When using triphenyl phosphine, the azide compound is refluxed in a tetrahydrofuran solution added with a small amount of water for 2 hours to produce the primary amine.

In the step 2, the amine compound of the formula 5, obtained in the step 1, is reacted with acetic anhydride in the presence of a base to give the corresponding compound of formula 6. Suitable base for use in this acetylation are triethyl amine, pyridine, and diisopropylethyl amine.

In the step 3, the compound of formula 6 is halogenated on position 4 of its phenyl ring to produce the corresponding compound of formula 7.

Preferable halide with which the phenyl ring is substituted is iodide. The iodination is preferably conducted by reacting the compound of formula 6 with iodine monochloride (ICl) alone, or iodine in the presence of silver trifluoroacetate (CF₃COOAg) at room temperature.

In the step 4, the halide group on position 4 of the phenyl ring is displaced with trimethyl stannyl by reaction with hexametylditin in the presence of a palladium catalyst to give the trimethylstannyl oxazolidinone derivative of formula 2. Dichlorobistriphenylphosphine palladium (II), or tetrakistriphenylphosphine palladium (0) is useful as the palladium catalyst.

This displacement is preferably carried out at 90 to 120° C. in a solvent, such as 1,4-dioxane, dimethylformamide, or tetrahydrofuran.

In the step 5, the trimethylstannyl oxazolidinone derivative of formula 2 is reacted with the pyridine or pyrimidine derivative of formula 3 in the presence of a palladium (0) or a palladium (II) catalyst to prepare the oxazolidinone compound of the present invention.

Preferably, this reaction is conducted at 60 to 150° C. for about 30 min to 12 hours. As a solvent for the reaction, dimethylformamide, 1,4-dioxane, and tetrahydrofuran may be used alone or in combination.

For use in the present invention, the pyridine halide of formula 3 can be prepared from, for example, dibromopyridine and pyridine, as illustrated in Scheme 3. Such preparation is reported in the literature (*J. Medicinal Chem.* V41, 2399(1998), *Chem. Pharm. Bull*, 314(1996), *J. Med. Chem.* 957(2000), *J. Med. Chem.* 1230(2000), *J. Med. Chem.* 1086(1991), *J. Med. Chem.* 2837(1997), *J. Med. Chem.* 2019(1998))

Scheme 3

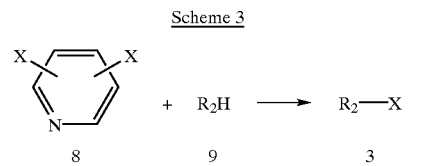

Wherein, R₂ and X are as defined above.

When R₂ is piperazinylpyrimidine, the synthesis of the compound of formula 1 progress by way of the intermediates of Scheme 4

Scheme 4

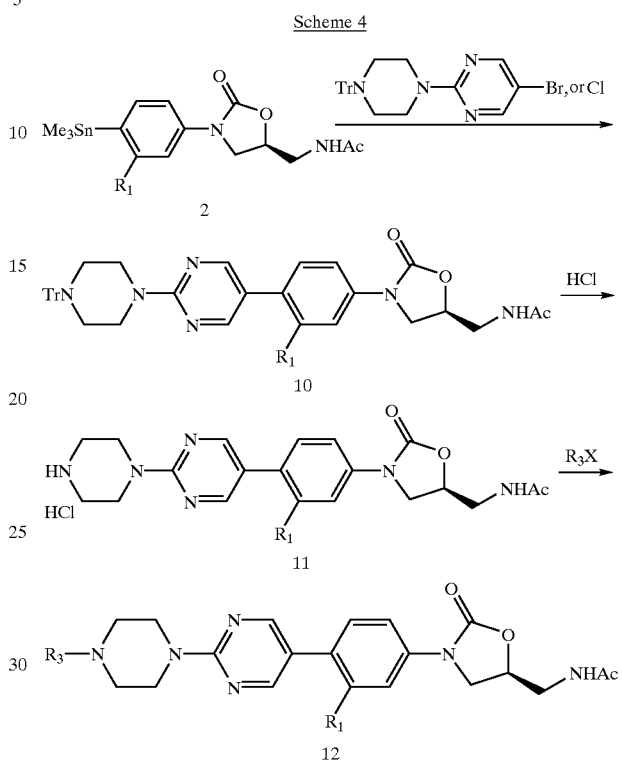

wherein, R₁ and R₃ are each as defined above, and X is a halogen atom.

As illustrated in Scheme 4, the trimetylstannly group of the compound of formula 2 is displaced with triphenylmethyl-protected piperazine pyrimidine, followed by the removal of the protecting group by use of a hydrochloric acid solution. The resulting deprotected compound of formula 11 is substituted on the amine group of the piperidine moiety to synthesize the compound of formula 12.

When R₂ is pyridine, the synthesis of the compound of formula 1 progress by way of the intermediates of Scheme 5

Scheme 5

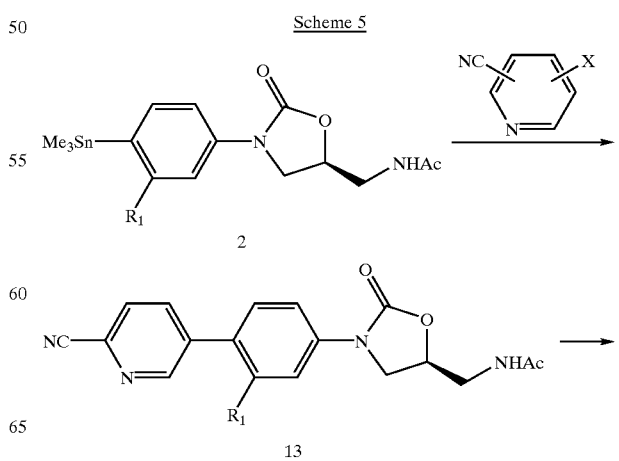

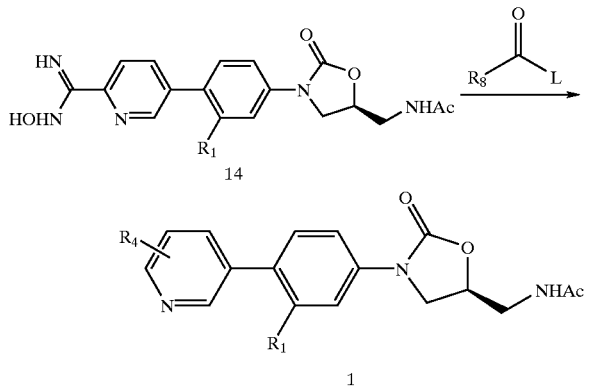

Wherein R₁, R₂, R₆ and X are each as defined above, and L is a typical leaving group and preferably halogen or methylcarbonyl oxy group.

As illustrated in Scheme 5, the trimethylstannyl, oxazolidinone derivative of formula 2 is reacted with a cyanopyridine derivative to synthesize an intermediate of formula 13, whose cyano group is then subjected to imination using hydroxylamine to form the corresponding compound of formula 14. It is cyclized to the desired compound as a result of reaction with a carboxylic acid derivative.

As for the synthesis of the intermediate of formula 13, it is performed by refluxing the reactants at 100 to 120° C. for 4 to 10 hours in an organic solvent, such as N-methylpyrrolidine or tetrahydrofuran.

In the presence of sodium hydrogen carbonate and hydroxylamine hydrochloride, the compound of formula 13 is iminated at a reflux temperature for 2 to 5 hours. Alcohols can be used as solvents with preference for ethanol, methanol or isopropanol.

Reaction of the compound of formula 14 with an activated carboxylic acid derivative provides the oxazolidinone derivative of formula 1. The activated carboxylic acid derivative is acyl chloride in which R₆ is substituted, or acetic anhydride. The cyclization is conducted at a reflux temperature for 4 to 8 hours in a solvent such as pyridine, tetrahydrofuran or acetone.

In accordance with a further aspect of the present invention, there is provided a pharmaceutical composition comprising the compound of formula 1 as an effective ingredient conferring antibacterial activity.

For formulating a pharmaceutical composition, at least one species of the compound of formula 1 is admixed with at least one pharmaceutically acceptable expedient, which is nontoxic to humans and inactive.

Administrable via oral or parenteral routes, the compounds of formula 1 may be used with ordinary medicine forms.

That is, the compounds of formula 1 can be formulated into various dosage forms for oral or parenteral administration. For formulation, pharmaceutically acceptable diluents, expedients and/or carriers may be used, including fillers, thickeners, binders, wetting agents, disintegrants, surfactants, etc. Solid dosage forms for oral administration are exemplified by tablets, pills, powders, granules, and capsules. These solid forms are prepared by admixing at least one compound of formula 1 with at least one expedient, such as starch, calcium carbonate, sucrose, lactose, gelatine, etc. In addition to expedients, a lubricant such as magnesium styrate may be added.

Exemplified by suspensions, internal solutions, emulsions, syrups, etc., liquid dosage forms for oral administration may comprise simple diluents, such as water and liquid paraffin, as well as wetting agents, sweeteners, aromatics, and/or perspectives.

Dosage forms for parenteral administration include sterile aqueous solutions, non-aqueous solvents, suspensions, emulsions, freeze-dried agents, suppositories, etc. For formulation of non-aqueous solvents and suspensions, vegetable oils, such as propylene glycol and polyethylene glycol, or injectable esters such as ethyl oleate, may be used. As bases for suppositories, Witepsol, macrogol, Tween 61, cocoa oil, laurinic acid, and glycerogelatine are useful.

In general, the compound of formula 1 may be administered in a total dose of 1.2 g to adults in 2 or 3 installments a day. However, the dose may vary depending on the conditions of the subject, including, for example, physical constitutions and weights of patients, kinds and severity of diseases, administration routes and intervals, etc.

It is found that not only does the compound of formula 1 show inhibitory activity against a broad spectrum of bacteria, but its antibacterial activity is excellent in vivo. For example, the compound of the present invention can exert potent antibacterial activity versus various human and animal pathogens, including Gram-positive bacteria such as Staphylococi, Enterococci and Streptococi, anaerobic microorganisms such as Bacteroides and Clostridia, and acid-resistant microorganisms such as *Mycobacterium tuberculosis* and *Mycobacterium avium*.

A better understanding of the present invention may be obtained in light of the following examples which are set forth to illustrate, but are not to be construed to limit the present invention.

PREPARATION EXAMPLE 1

Preparation of N-Carbobenzoxy-3-fluoroaniline

In 1 L of tetrahydrofuran (THF) was dissolved 100 g (0.90 moles) of 3-fluoroaniline and the solution was added with 150 g (1.8 moles) of sodium hydrogen carbonate. After being cooled to 0° C., the solution was slowly added with 154 ml (1.08 moles) of N-carbobenzyloxy chloride (CbzCl) for reaction. While the temperature was maintained at 0° C., the reaction mixture was let to react for 2 hours with stirring. Afterwards, the reaction was extracted with 0.5 L of ethyl acetate. The organic layer, after being separated, was washed with brine, dried over anhydrous MgSO₄, and concentrated in vacuo. The residue was washed twice with n-hexane to afford the title compound as a white crystal. 132 g. Yield 85%.

PREPARATION EXAMPLE 2

(R)-[N-3-(3-Fluorophenyl)-2-oxo-5-oxazolidinyl] methanol

In 1.3 L of THF was dissolved 133 g (0.54 moles) of N-carbobenzoxy-3-fluoroaniline prepared in Preparation Example 1 and the solution was cooled to −78° C. To the solution, 370 ml of n-butyl lithium (n-BuLi, 1.6 M/n-hexane, 0.59 moles) was slowly added in a nitrogen atmosphere, followed by stirring for 10 min. Following cautious introduction of 84 ml (1.1 moles) of (R)-(−)-glycidylbutyrate, the reaction mixture was stirred for 2 hours at the same temperature and allowed to stand for 24 hours at room temperature for reaction. After completion of the reaction, the solution was added with an ammonium chloride (NH₄Cl) solution and extracted with 0.5 L of ethyl acetate at room temperature. The organic layer, thus separated, was washed with brine, dried over anhydrous magnesium sulfate, and concentrated in vacuo. The residue was dissolved in 100 ml of ethyl acetate and washed with n-hexane to give white crystals, which were purified to the title compound. 80 g. Yield 70%.

$^1$H NMR (DMSO-d$_6$) δ 7.85 (t, 4H), 7.58 (dd, 1H), 7.23 (dd, 8H), 4.69 (m, 1H), 4.02 (t, 1H), 3.80 (dd, 1H), 3.60 (br dd, 2H).

PREPARATION EXAMPLE 3

Preparation of (R)-[N-3-(3-Fluorophenyl)-2-oxo-5-oxazolidinyl]methylmethane Sulfonate In 300 ml of methylene chloride was dissolved 55.1 g (0.26 mol) of (R)-[N-3-(3-fluorophenyl)-2-oxo-5-oxazolidinyl]ethanol, and 54.4 ml (0.39 moles) of triethylamine and 24 ml (0.312 moles) of methanesulfonyl chloride were slowly added to the solution at 0° C. After being stirred at 0° C. for about 40 min, the solution was added with water, extracted with chloroform, dried over anhydrous magnesium sulfate, concentrated under vacuum, and dried to give the title compound. 78.3 g.

PREPARATION EXAMPLE 4

Preparation of (R)-[N-3-(3-Fluorophenyl)-2-oxo-5-oxazolidinyl]methyl Azide

In 800 ml of dimethylformamide was dissolved 78 g (0.27 moles) of (R)-[N-3-(3-fluorophenyl)-2-oxo-5-oxazblidinyl] ethyl methane sulfonate and the solution was added with 26.3 g (0.41 moles) of sodium azide and stirred at 100° C. for 2 hours. The solution was separated into layers by adding water, followed by extraction with ethyl acetate. The ethyl acetate layer was dehydrated, concentrated under vacuum, and dried to obtain the title compound. 70 g.

PREPARATION EXAMPLE 5

Preparation of (S)-[N-3-(3-Fluorophenyl)-2-oxo-5-oxazolidinyl]methyl Amine

In a mixture of tetrahydrofuran (400 ml) and methanol (80 ml) was dissolved 70 g of (R)-[N-3-(3-fluorophenyl)-2-oxo-5-oxazolidinyl]methyl azide, and the azide compound was reduced at room temperature for 24 hours under a hydrogen atmosphere in the presence of 8 g of palladium on carbon (Pd/C) with stirring, followed by filtration and concentration in vacuo to obtain the tile compound. 54.6 g.

PREPARATION EXAMPLE 6

Preparation of (S)-[N-3-(3-Fluorophenyl)-2-oxo-5-oxazolidinyl]methyl Acetamide

In 500 ml of methylene chloride was dissolved 54.6 g (0.26 moles) of (S)-[N-3-(3-fluorophenyl)-2-oxo-5-oxazolidinyl]methyl amine and the solution was reacted with 36.8 ml (0.39 moles) of acetic anhydride at 0° C. for 1 hour in the presence of 72.4 ml (0.52 moles) of triethyl amine with stirring. Afterwards, the reaction mixture was added with water, and extracted with chloroform. The organic layer thus obtained was washed with brine, dried, and concentrated in vacuo to give ivory powder which was then three times washed with n-hexane to obtain the title compound. 49.6 g. Yield 76%.

PREPARATION EXAMPLE 7

Preparation of (S)-[N-3-(4-Iodo-3-fluorophenyl)-2-oxo-5-oxazolidinyl]methyl Acetamide In a mixture of acetic acid (2.5 L) and trifluoroacetic acid (700 ml) was dissolved 54.5 g (0.22 moles) of (S)-[N-3-(3-fluorophenyl)-2-oxo-5-oxazolidinyl]ethyl acetamide which was then slowly added at room temperature with a solution of 455.7 g (2.8 moles) of iodine monochloride (ICl) in 300 ml of acetic acid. Iodination was carried out for 15 hours at room temperature with stirring, followed by the addition of diethyl ether to give precipitates. They, after being filtered, were dissolved in a mixture of chloroform and methanol, washed with sodium thiosulfate and sodium hydrogen carbonate (NaHCO$_3$), and dehydrated. The residue was concentrated under vacuum and dried to obtain the title compound. 59.5 g. Yield 80.4%

$^1$H NMR (DMSO-d$_6$) δ 8.23 (t, 1H), 7.82 (dd, 1H), 7.56 (dd, 1H), 7.18 (dd, 1H), 4.74 (m, 1H), 4.10 (t, 1H), 3.73 (dd, 1H), 3.40 (br dd, 2H), 1.83 (s,3H).

PREPARATION EXAMPLE 8

Preparation of (S)-[N-3-(4-Trimethylstannyl-3-fluorophenyl)-2-oxo-5-oxazolidinyl]methyl Acetamide In 660 ml of 1,4-dioxane was dissolved 50 g of (S)-[N-3-(4-iodo-3-fluorophenyl)-2-oxo-5-oxazolidinyl]methyl acetamide which was then reacted for 2 hours with 52 g of hexamethyldilin in the presence of 9.3 g of dichlorobistriphenylphosphine palladium (II) with refluxing. The reaction solution was filtered by use of cellite and the filtrate was concentrated under vacuum. From the residue, the title compound was separated through column chromatography. 45 g.

PREPARATION EXAMPLE 9

Preparation of 2-Piperazin-1-yl-5-iodopyrimidine

In a mixture of acetic acid (5 ml), water (1 ml) and sulfuric acid (0.15 ml) was dissolved 2 g of 1-(2-pyrimidyl) piperazine which was then reacted with 0.86 g of iodine in the presence of 0.38 g of periodic acid at 100° C. for 6 hours with stirring. Chloroform was added to the reaction mixture, followed by washing with sodium hydrogen carbonate and brine. The organic layer thus obtained was dehydrated, filtered and concentrated under vacuum. Purification with column chromatography provided the title compound. 600 mg.

$^1$H-NMR (CDCl$_3$) δ 8.16 (s, 2H), 3.87 (m, 4H), 3.0 (m, 4H).

PREPARATION EXAMPLE 10

Preparation of 2-(4-Triphenylmethylpiperazin-1-yl)-5-iodopyrimidine

In 100 ml of methylene chloride was dissolved 13 g of 2-piperazin-1-yl-5-iodopyrimidine which was then reacted with 15 g of triphenylmethyl chloride at room temperature for 1 hour in the presence of 16 ml of triethylamine with stirring. The reaction mixture was added with methylene chloride, after which the organic layer was washed with water and brine, dehydrated, filtered and concentrated under vacuum. The residue was purified by use of ethyl acetate and a small quantity of methanol to obtain the title compound. 10 g.

$^1$H-NMR (CDCl$_3$) δ 8.13 (s, 2H), 7.49 (m, 5H), 7.23 (m, 10H), 3.86 (m, 4H), 2.33 (m, 4H).

PREPARATION EXAMPLE 11

Preparation of 2-Acetylamino-5-bromopyridine

In 29 ml of pyridine was dissolved 1 g of 2-amino-5-bromopyridine which was then acetylated through reaction with 0.61 ml of acetyl chloride at room temperature for 15 hours with stirring. Following the addition of water, the reaction mixture was extracted with ethyl acetate, and the organic layer thus obtained was washed with brine. Dehydration, filtration and concentration under vacuum of the organic layer provided a solid which was then recrystallized in ethanol and hexane to obtain the title compound. 1.06 g. Yield 85%.

$^1$H-NMR (CDCl$_3$) δ 8.60 (s, 1H), 8.34 (d, 1H), 8.18 (d, 1H), 7.79 (dd, 1H), 2.18 (s, 3H).

PREPARATION EXAMPLE 12

Preparation of 2-Acetoxyacetylamino-5-bromopyridine

In 29 ml of methylene chloride was dissolved 1 g of 2-amino-5-bromopyridine which was then reacted with 0.93 ml of acetoxyacetyl chloride in the presence of 1.61 ml of triethyl amine at room temperature for 1 hour with stirring. Water was added to the reaction mixture before extraction with methylene chloride. The organic layer thus obtained was washed with brine, dehydrated, filtered and concentrated in vacuo. Recrystallization of the concentrate in ethyl ether gave the title compound. 615 mg.

$^1$H-NMR (CDCl$_3$) δ 8.57 (s, 1H), 8.32 (d, 1H), 8.15 (d, 1H), 7.82 (dd, 1H), 4.73 (s, 2H), 2.21 (s, 3H).

PREPARATION EXAMPLE 13

Preparation of 2-(1-Tetrazolyl)-5-bromopyridine

In 10 ml of 1-methyl-2-pyrrolidone was dissolved 1.0 g of 2,5-dibromopyridine and the solution was added with 0.5 g of 1,2,3,4-tetrazole, along with 1.75 g of potassium carbonate. The reaction mixture was reacted at 100° C. for 3 hours with stirring. After completion of the reaction, the reaction mixture was added with water and extracted with ethyl acetate. The organic layer thus obtained was dehydrated, filtered and concentrated and the concentrate was subjected to column chromatography to give the title compound. 0.8 g.

$^1$H-NMR (DMSO-d$_6$) δ 10.17 (s, 1H), 8.80 (d, 1H), 8.40 (dd, 1H), 8.00 (d, 1H).

PREPARATION EXAMPLE 14

Preparation of 2-[5-Methyl-(1,3,4)-oxadiazol-2-yl]-5-bromopyridine

In 10 ml of acetic anhydride was dissolved 1 g of 2-(5-tetrazolyl)-5-bromopyridine, followed by refluxing for 2 hours. After completion of the reaction, the same post-treatment as in Preparation Example 13 was conducted to give the title compound. 0.6 g.

$^1$H-NMR (CDCl$_3$) δ 8.79 (d, 1H), 8.09 (dd, 1H), 7.97 (dd, 1H), 2.64 (s, 3H).

PREPARATION EXAMPLE 15

Preparation of 2-[5-Methyl-(1,2,4)-oxadiazol-3-yl]-5-bromopyridine

In 250 ml of acetic anhydride was dissolved 8.6 g of 2-(imino-N-hydroxyaminomethyl)-5-bromopyridine and the solution was refluxed for one day. After completion of the reaction, the same post-treatment as in Preparation Example. 13 was conducted to give the title compound. 2.8 g.

$^1$H-NMR (CDCl$_3$) δ 8.80 (dd, 1H), 7.96 (dd, 2H), 2.67 (s, 3H).

PREPARATION EXAMPLE 16

Preparation of 2-(1-Methyl-5-tetrazolyl)-5-bromopyridine and 2-(2-Methyl-5-tetrazolyl)-5-bromopyridine In 5 ml of dimethylformamide was dissolved 400 mg of 2-(5-tetrazolyl)-5-bromopyridine and the solution was reacted with 502 mg of iodomethane in the presence of 300 mg of potassium hydroxide at room temperature for 1 hour with stirring. After completion of the reaction, a post-treatment similar to that of Preparation Example 3 was conducted to obtain 110 mg of 2-(1-methyl-5-tetrazolyl)-5-bromopyridine (thin layer chromatography eluting with a mixture of 1:4 ethyl acetate:hexane, Rf: 0.3) and 220 mg of 2-(2-methyl-5-tetrazolyl)-5-bromopyridine (thin layer chromatography eluting with a mixture of 1:4 ethyl acetate:hexane, Rf: 0.5).

NMR data of 2-(1-methyl-5-tetrazolyl)-5-bromopyridine
$^1$H-NMR (CDCl$_3$) δ 8.80 (d, 1H), 8.11 (d, 1H), 7.96 (dd, 1H), 4.43 (s, 3H).

PREPARATION EXAMPLE 17

Preparation of 2-[4-Carboxyethoxy-(1,2,3)-triazol-1-yl]-5-bromopyridine

In 1 ml of dimethylformamide was dissolved 100 mg of 2-azide-5-bromopyridine, followed by the addition of 10 mg of ethyl propiolate at room temperature. Temperature elevation of the reaction mixture to 120° C. made a reaction progress faster. After completion of the reaction, the same post-treatment as in Preparation Example 13 was conducted to obtain the title compound. 100 mg.

$^1$H-NMR (DMSO-d$_6$) δ 8.85 (d, 1H), 8.74 (dd, 1H), 8.34 (dd, 1H), 8.06 (t, 1H), 4.38 (q, 2H), 2.03 (s, 1H), 1.23 (t, 3H).

PREPARATION EXAMPLE 18

Preparation of 2-(3-Pyrrolin-1-yl)-5-bromopyridine

In 100 ml of 1-methyl-2-pyrrolidone was dissolved 10 g of 2,5-dibromopyridine which was then added with 3.5 ml of 3-pyrrolidine, along with 8.7 g of potassium carbonate at room temperature, followed by reacting them at 100° C. for 24 hours. After completion of the reaction, the same post-treatment was carried out as in Preparation Example 3 to obtain the title compound. 8 g.

$^1$H-NMR (CDCl$_3$) δ 7.48 (d, 1H), 7.39 (dd, 1H), 6.21 (d, 1H), 5.89 (s, 2H), 4.15 (s, 4H).

PREPARATION EXAMPLE 19

Preparation of 2-[2-oxo-(1,3)-Oxazolidin-1-yl]-5-bromopyridine

In 20 ml of 1-methyl-2-pyrrolidone was dissolved 1.2 g of 2-oxazolidone which was then added with 3.92 g of 2,5-dibromopyridine, along with 3.81 g of potassium carbonate at room temperature. Reaction was conducted at 120° C. for 4 hours with stirring. After completion of the reaction, the same post-treatment as in Preparation Example 13 was carried out to obtain the title compound. 50 mg.

$^1$H-NMR (DMSO-d$_6$) δ 8.33 (d, 1H), 8.12 (dd, 1H), 7.79 (dd, 1H), 4.47 (m, 2H), 4.22 (m, 2H).

PREPARATION EXAMPLE 20

Preparation of 2-[(1,2,4)-Oxadiazol-3-yl]-5-bromopyridine

In 10 ml of triethyloxoformate was dissolved 1.0 g of 2-(imino-N-hydroxyaminomethyl)-5-bromopyridine, after which 2–3 drops of trifluoroboronetherate (BF$_3$etherate) were added to the solution which was then reacted for 3 hours with refluxing. After completion of the reaction, the same post-treatment as in Preparation Example 3 was carried out to obtain the title compound. 0.7 g.

$^1$H-NMR (CDCl$_3$) δ 8.77 (brs, 2H), 8.00 (m, 2H).

PREPARATION EXAMPLE 21

Preparation of 2-[(1,2,3)-Triazol-1-yl]-5-bromopyridine

In 20 ml of 1-methyl-2-pyrrolidone was dissolved 1.72 g of 2,5-dibromopyridine, followed by the addition of 500 mg of 2H-(1,2,3)-triazole and 3 g of potassium carbonate at room temperature. Reaction was conducted at 100° C. for 24 hours. After completion of the reaction, the same post-treatment as in Preparation Example 3 was carried out to obtain the title compound. 120 mg.

$^1$H-NMR (DMSO-d$_6$) δ 8.85 (d, 1H), 8.75 (dd, 1H), 8.34 (dd, 1H), 8.06 (t, 1H), 8.00 (s, 1H).

PREPARATION EXAMPLE 22

Preparation of 2-[3-Methyl-2-oxo-(2,3)-dihydro-(1,3,4)-triazol-1-yl]-5-bromopyridine In dimethylformamide was dissolved 311 mg of 2-[2-oxo-(2,3)-dihydro-(1,3,4)-triazol-1-yl]-5-bromopyridine and the solution was added with 217 mg of potassium hydroxide and then dropwise with 366 ml of iodomethane at 0° C. Reaction was conducted at room temperature for 4 hours and led to completion. After the reaction was completed, the same post-treatment as in Preparation Example 13 was carried out to obtain the title compound. 290 mg.

$^1$H-NMR (DMSO-d$_6$) δ 8.62 (d, 1H), 8.61 (s, 1H), 8.27 (dd, 1H), 8.13 (d, 1H), 3.39 (s, 3H).

PREPARATION EXAMPLE 23

Preparation of 2-[3-t-Butoxycarbonyl-2-oxo-(2,3)-dihydro-(1,3,4)-triazol-1-yl]-5-bromopyridine In 20 ml of methylenechloride was dissolved 1.6 g of 2-[2-oxo-(2,3)-dihydro-(1,3,4)-triazol-1-yl]-5-bromopyridine which was added with 1.11 ml of triethyl amine and 3.4 g of di-tert-butylcarbonate. Reaction was conducted at room temperature for 1 hour with the catalytic aid of a small amount of dimethylaminopyrrolidine with stirring. After the reaction was terminated, the same post-treatment as in Preparation Example 13 was carried out to obtain the title compound. 2.84 g.

$^1$H-NMR (CDCl$_3$) δ 8.47 (s, 1H), 8.45 (dd, 1H), 8.13 (d, 1H), 7.91 (dd, 1H), 1.16–1.20 (m, 9H).

PREPARATION EXAMPLE 24

Preparation of 2-[2-oxo-(1,3)-Imidazolidin-1-yl]-5-bromopyridine

In 50 ml of 1-methyl-2-pyrrolidone was dissolved 15.14 g of 2,5-dibromopyridine and the solution was added with 5.0 g of 2-oxo-1,3-imidazolidine(2-imidazolidone, 2-imidazolidione) and 16.05 g of potassium carbonate at room temperature. The reactants were reacted at 100° C. for 24 hours with stirring. After completion of the reaction, the same post-treatment as in Preparation Example 13 was carried out to obtain the title compound. 2.0 g.

$^1$H-NMR (CDCl$_3$) δ 8.55 (d, 1H), 8.45 (s, 1H), 8.34 (d, 1H), 8.15 (dd, 1H).

PREPARATION EXAMPLE 25

Preparation of 2-[(1,3)-Oxazol-5-yl]-5-bromopyridine

In 5.4 ml of methanol was dissolved 200 mg of 5-bromo-2-formyl pyridine (5-bromo-2-pyridinyl aldehyde) which was then reacted with 231 mg of tosylmethylisocyanide for 3 hours in the presence of 178 mg of potassium carbonate under reflux. After completion of the reaction, the same post-treatment as in Preparation Example 13 was carried out to obtain the title compound. 204 mg.

$^1$H-NMR (CDCl$_3$) δ 8.65 (d, 1H), 7.95 (s, 1H), 7.89 (dd, 1H), 7.68 (s, 1H), 7.56 (d, 1H).

PREPARATION EXAMPLE 26

Preparation of 2-(4-Hydroxy-piperidin-1-yl-5-bromopyridine

In 100 ml of 1-methyl-2-pyrrolidone was dissolved 10 g of 2,5-dibromopyridine which was then added with 5.2 g of 4-hydroxypiperidine, along with 17.5 g of potassium carbonate at room temperature. Reaction was conducted at 100° C. for 3 hours with stirring. After completion of the reaction, the same post-treatment as in Preparation Example 13 was carried out to obtain the title compound. 9 g.

$^1$H-NMR (CDCl$_3$) δ 7.43 (d, 1H), 7.38 (dd, 1H), 6.21 (d, 1H), 4.69 (m, 1H), 3.72 (m, 2H), 3.12 (m, 2H), 1.75 (m, 2H), 1.34 (m, 2H).

PREPARATION EXAMPLE 27

Preparation of 2-[3-t-Butoxycarbonyl-2-oxo-(1,3)-imidazolidin-1-yl]-5-bromopyridine In 2 ml of tetrahydrofuran was dissolved 200 mg of 2-(2-oxo-1,3-imidazolidin-1-yl)-5-bromopyridine, followed by reaction with 216 mg of di-tert-butyldicarbonate at room temperature for 4 hours in the presence of 300 ml of triethyl amine. After completion of the reaction, the same post-treatment as in Preparation Example 13 was carried out to obtain the title compound. 310 mg.

$^1$H-NMR (CDCl$_3$) δ 8.31 (d, 1H), 8,21 (d, 1H), 7.72 (dd, 1H), 3.99 (m, 2H), 3.87 (m, 2H), 1.54 (s, 9H).

EXAMPLE 1

Preparation of (S)-[N-3-(4-Pyrimidin-5-yl)-3-fluorophenyl)-2-oxo-5-oxazolidinyl]methyl Acetamide In 4 ml of dimethylformamide was dissolved 322 mg of (S)-[N-3-(4-trimethylstannyl-3-fluorophenyl)-2-oxo-5-oxazolidinyl]methyl acetamide and the solution was added with 400 mg of 5-iodopyrimidine, 0.27 ml of triethyl amine, and 0.22 g of dichlorobistriphenylphosphine palladium (II) at room temperature. Subsequently, reaction was conducted for 4 hours at 100° C. with stirring. Water was added to the reaction mixture which was then extracted with ethyl acetate. The organic layer thus separated was washed with brine, dehydrated, filtered and concentrated in vacuo. Through column chromatography, the concentrate was purified to the title compound. 100 mg.

$^1$H-NMR (CDCl$_3$) δ 9.16 (s, 1H), 8.87 (s, 2H), 7.62 (dd, 1H), 7.43 (t, 1H), 7.33 (dd, 1H), 6.37 (bt, 1H), 4.82 (m, 1H), 4.08 (t, 1H), 3.84 (dd, 1H), 3.67 (m, 2H), 2.00 (s, 3H).

EXAMPLE 2

Preparation of (S)-[N-3-(4-(2-Methoxypyrimidin-5-yl)-3-fluorophenyl)-2-oxo-5-oxazolidinyl]methyl Acetamide The title compound was prepared in a manner similar to that of Example 1, except that, 2-methoxy-5- iodopyrimidine, instead of 5-iodopyrimidine, was used as a starting material.

EXAMPLE 3

Preparation of (S)-[N-3-(4-(2-Aminopyrimidin-5-yl)-3-fluorophenyl)-2-oxo-5-oxazolidinyl]methyl Acetamide The same procedure as in Example 1 was conducted, except for using, instead of 5-iodopyrimidine, 2-amino-5-bromopyrimidine as a starting material, to prepare the title compound. 45 mg.

$^1$H-NMR (DMSO-$d_6$) 8.42 (s, 1H), 8.30 (s, 1H), 8.26 (t, 1H), 7.53 (m, 4H), 6.67 (s, 1H), 4.75 (m, 1H), 4.16 (m, 1H), 3.77 (m, 1H), 3.42 (m, 2H), 1.83 (s, 3H).

EXAMPLE 4

Preparation of (S)-[N-3-(4-(2-(4-Triphenylmethylpiperazin-1-yl)pyrimidin-5-yl)-3-fluorophenyl)-2-oxo-5-oxazolidinyl]methyl Acetamide In 5.6 ml of dimethylformamide was dissolved 400 mg of (S)-[N-3-(4-trimethylstannyl-3-fluorophenyl)-2-oxo-5-oxazolidinyl]methyl acetamide which was then reacted with 770 mg of 2-(4-triphenylmethylpiperazin-1-yl)-5-iodopyrimidine at 80° C. for 1 hour in the presence of 48 mg of copper chloride. Water was added to the reaction mixture, followed by extraction with ethyl acetate. The organic layer thus obtained was washed with brine, dehydrated, filtered and concentrated in vacuo. The concentrate was purified by column chromatography to give the title compound. 300 mg.

$^1$H-NMR (DMSO-$d_6$) 8.48 (s, 2H), 8.25 (t, 1H), 7.40 (m, 15H), 7.17 (m, 2H), 6.95 (m, 1H), 4.72 (m, 1H), 4.11 (m, 1H), 3.73 (m, 1H), 3.40 (t, 2H), 1.81 (s, 3H).

EXAMPLE 5

Preparation of (S)-[N-3-(4-(2-Piperazin-1-yl-pyrimidin-5-yl)-3-fluorophenyl)-2-oxo-5-oxazolidinyl]methyl Acetamide Hydrochloride To a solution of 200 mg of (S)-[N-3-(4-(2-(4-triphenylmethylpiperazin-1-yl)pyrimidin-5-yl)-3-fluorophenyl)-2-oxo-5-oxazolidinyl]methyl acetamide in tetrahydrofuran was added 1 ml of a 6 N hydrochloride solution at room temperature, followed by stirring for 24 hours. The solid thus formed was purified and washed with tetrahydrofuran and ethyl ether to obtain the title compound. 110 mg.

$^1$H-NMR (DMSO-$d_6$) 9.49 (bs, 1H), 8.63 (s, 2H), 8.33 (t, 1H), 7.49 (m, 4H), 4.74 (m, 1H), 4.13 (t, 1H), 4.02 (m, 4H), 3.78 (dd, 1H), 3.41 (t, 2H), 3.16 (m, 4H), 1.81 (s, 3H).

EXAMPLE 6

Preparation of (S)-[N-3-(4-(2-(4-Acetylpiperazin-1-yl)pyrimidin-5-yl)-3-fluorophenyl)-2-oxo-5-oxazolidinyl]methyl Acetamide A solution of 30 mg of (S)-[N-3-(4-(2-piperazin-1-ylpyrimidin-5-yl)-3-fluorophenyl)-2-oxo-5-oxazolidinyl]methyl acetamide hydrochloride in tetrahydrofuran were added with 10 μl of acetyl chloride and 30.3 1 of triethyl amine at room temperature and let to react for 30 min with stirring. After completion of the acetylation, chloroform was added to the reaction mixture which was then washed with water and brine. The organic layer thus obtained was dehydrated, filtered and concentrated in vacuo. The concentrate was subjected to column chromatography to give the title compound. 30 mg.

$^1$H-NMR (CDCl$_3$) 8.47 (s, 2H), 7.53 (dd, 1H), 7.29 (m, 2H), 6.30 (t, 1H), 4.79 (m, 1H), 3.86 (m, 5H), 3.66 (m, 4H), 3.51 (m, 2H), 2.14 (s, 3H), 2.01 (s, 3H).

EXAMPLE 7

Preparation of (S)-[N-3-(4-(2-(4-Benzyloxyacetylpiperazin-1-yl)pyrimidin-5-yl)-3-fluorophenyl)-2-oxo-5-oxazolidinyl]methyl Acetamide The same procedure as in Example 6 was conducted, except for using, instead of acetyl chloride, 26.6 μl of benzyloxyacetyl chloride as a starting material, to prepare the title compound. 30 mg.

$^1$H-NMR (CDCl$_3$) δ 8.48 (s, 2H), 1.52 (dd, 1H), 7.27 (m, 7H), 6.15 (t, 1H), 4.79 (m, 1H), 4.60 (s, 2H), 4.21 (s, 2H), 4.05 (t, 1H), 3.83 (m, 5H), 3.65 (m, 6H), 2.01 (s, 3H).

EXAMPLE 8

Preparation of (S)-[N-3-(4-(2-(4-Acetoxyacetylpiperazin-1-yl)pyrimidin-5-yl)-3-fluorophenyl)-2-oxo-5-oxazolidinyl]methyl Acetamide The same procedure as in Example 6 was conducted, except for using, instead of acetyl chloride, 16 μl of acetoxyacetyl chloride as a starting material, to prepare the title compound. 23 mg.

$^1$H-NMR (CDCl$_3$) δ 8.49 (d, 2H), 7.56 (dd, 1H), 7.35 (m, 2H), 6.04 (t, 1H), 4.80 (m, 1H), 4.77 (s, 2H), 4.06 (t, 1H), 3.95 (m, 4H), 3.70 (m, 5H), 3.50 (m, 2H), 2.21 (s, 3H), 2.01 (s, 3H).

EXAMPLE 9

Preparation of (S)-[N-3-(4-(2-(4-Hydroxyacetylpiperazin-1-yl)pyrimidin-5-yl)-3-fluorophenyl)-2-oxo-5-oxazolidinyl]methyl Acetamide In methanol was dissolved 220 mg of the title compound of Example 8 which was then hydroxylated with 1 ml of a 1 N KOH solution at room temperature for 1 hour with stirring. Following the removal of excess alcohol by concentration under vacuum, the residue was added with water and extracted with chloroform. The organic layer was dehydrated, filtered and concentrated in vacuo. Purification through column chromatography provided the title compound. 189 mg.

$^1$H-NMR (CDCl$_3$) δ 8.48 (s, 2H), 7.54 (dd, 1H), 7.34 (t, 1H), 7.26 (dd, 1H), 4.79 (m, 1H), 4.21 (s, 2H), 4.05 (t, 1H), 3.88 (m, 4H), 3.77 (m, 4H), 3.65 (m, 1H), 3.34 (m, 2H), 2.00 (s, 3H).

EXAMPLE 10

Preparation of (S)-[N-3-(4-(2-(4-Dimethylaminoacetoxyacetylpiperazin-1-yl)pyrimidin-5-yl)-3-fluorophenyl)-2-oxo-5-oxazolidinyl]methyl Acetamide In 2.5 ml of pyridine was dissolved 50 mg of (S)-[N-3-(4-(2-(4-hydroxyacetylpiperazin-1-yl)pyrimidin-5-yl)-3- fluorophenyl)-2-oxo-5-oxazolidinyl]methyl acetamide and the solution was dropwise added with 43.7 mg of N,N-dimethylglycine, 84 mg of 1-(3-dimethylaminopropyl)-3-ethylcarbodiimide hydrochloride, and 20 mg of 4-dimethylaminopyridine and stirred at room temperature for 15 hours. The reaction mixture was added with water and extracted with ethyl acetate. The organic layer thus obtained, after being washed with brine, was dehydrated, filtered and concentrated in vacuo. The concentrate was purified by column chromatography to obtain the title compound. 22 mg.

$^1$H-NMR (CDCl$_3$) δ 8.49 (s, 2H), 7.56 (dd, 1H), 7.34 (t, 1H), 7.27 (dd, 1H), 6.01 (t, 1H), 4.83 (s, 2H), 4.79 (m, 1H), 4.06 (t, 1H), 3.89 (m, 4H), 3.78 (m, 4H), 3.32 (s, 2H), 2.40 (s, 6H), 2.01 (s, 3H).

EXAMPLE 11

Preparation of (S)-[N-3-(4-(2-(4-Bromoacetylpiperazin-1-yl)pyrimidin-5-yl)-3-fluorophenyl)-2-oxo-5-oxazolidinyl]methyl Acetamide The same procedure as in Example 6 was conducted, except for using, instead of acetyl chloride, 63.06 μl of bromoacetyl, to prepare the title compound. 49 mg.

$^1$H-NMR (CDCl$_3$) δ 8.49 (s, 2H), 7.56 (dd, 1H), 7.34 (t, 1H), 7.26 (dd, 1H), 6.01 (t, 1H), 4.80 (m, 1H), 4.06 (t, 1H), 3.95 (m, 4H), 3.87 (s), 3.77 (m, 4H), 3.65 (m, 1H), 3.34 (m, 2H), 2.00 (s, 3H).

EXAMPLE 12

Preparation of (S)-[N-3-(4-(2-(Morpholin-4-yl)-methylcarbonlypiperazin-1-yl)pyrimidin-5-yl)-3-fluorophenyl]-2-oxo-5-oxazolidinyl]methyl Acetamide In tetrahydrofuran, 25 mg of (S)-[N-3-(4-(2-(4-bromoacetylpiperazin-1-yl)pyrimidin-5-yl)-3-fluorophenyl)-2-oxo-5-oxazolidinyl]methyl acetamide was reacted with 8 μl of morpholine at room temperature for 2 hours in the presence of 19.3 μl of triethyl amine. The reaction mixture was concentrated in vacuo, followed by purification through column chromatography to give the title compound. 25 mg.

$^1$H-NMR (CDCl$_3$) δ 8.50 (d, 2H), 7.56 (dd, 1H), 7.35 (m, 2H), 5.99 (t, 1H), 4.79 (m, 1H), 4.06 (t, 1H), 3.89 (m, 5H), 3.73 (m, 10H), 2.55 (m, 4H), 2.01 (s, 3H).

EXAMPLE 13

Preparation of (S)-[N-3-(4-(2-(4-(Imidazol-1-yl-carbonyloxymethyl Carbonyl Piperazin-1-yl) pyrimidin-5-yl)-3-fluorophenyl)-2-oxo-5-oxazolidinyl)methyl Acetamide In tetrahydrofuran, 30 mg of (S)-[N-3-(4-(2-(4-hydroxyacetylpiperazin-1-yl)pyrimidin-5-yl)-3-fluorophenyl)-2-oxo-5-oxazolidinyl]methyl acetamide was reacted with 34 mg of 1,1-carbonyldiimidazole at room temperature for 1 hour with stirring. The reaction mixture was added with chloroform and washed with sodium hydrogen carbonate. The organic layer thus obtained was dehydrated, filtered and concentrated in vacuo. Column chromatography with the concentrate provided the title compound. 28 mg.

$^1$H-NMR (CDCl$_3$) δ 8.50 (d, 2H), 8.19 (s, 1H), 7.56 (dd, 1H), 7.50 (s, 1H), 7.35 (m, 2H), 7.07 (s, 1H), 6.06 (t, 1H), 5.06 (s, 2H), 4.79 (m, 1H), 4.06 (t, 1H), 3.95 (m, 4H), 3.75 (m, 5H), 3.48 (m, 2H), 2.01 (s, 3H).

EXAMPLE 14

Preparation of (S)-[N-3-(4-(2-(4-Chloroacetylpiperazin-1-yl)pyrimidin-5-yl)-3-fluorophenyl)-2-oxo-5-oxazolidinyl]methyl Acetamide The same procedure as in Example 6 was conducted, except for using, instead of acetyl chloride, 54.5 μl of chloroacetyl chloride as a starting material, to prepare the title compound. 102 mg.

$^1$H-NMR (CDCl$_3$) δ 8.49 (s, 2H), 7.56 (dd, 1H), 7.39 (t, 1H), 7.27 (dd, 1H), 6.01 (t, 1H), 4.78 (m, 1H), 4.11 (s, 2H), 4.05 (t, 1H), 3.88 (m, 4H), 3.77 (m, 4H), 3.65 (m, 6H), 2.01 (s, 3H).

EXAMPLE 15

Preparation of (S)-[N-3-(4-(2-(4-Methoxycarbonylmethylaminoacetylpiperazin-1-yl) pyrimidin-5-yl)-3-fluorophenyl)-2-oxo-5-oxazolidinyl]methyl Acetamide In methanol was dissolved 50 mg of the title compound of Example 14 and the solution was added with 181 μl of triethyl amine and 32 mg of glycine methylester and refluxed for 4 hours. Following removal of excess methanol, the residue was added with water and extracted with chloroform. The organic layer thus separated was dehydrated, filtered and concentrated in vacuo. Through column chromatography, the concentrate was purified to the title compound. 20 mg.

EXAMPLE 16

Preparation of (S)-[N-3-(4-(2-(4-(4-Methoxyphenylpiperazin-4-yl)acetylpiperazin-1-yl) pyrimidin-5-yl)-3-fluorophenyl)-2-oxo-5-oxazolidinyl]methyl Acetamide Except for starting with 18 mg of methoxyphenylpiperazine instead of glycinemethylester hydrochloride, the same procedure as in Example 15 was conducted to prepare the title compound. 32 mg.

$^1$H-NMR (CDCl$_3$) δ 8.49 (d, 2H), 7.56 (dd, 1H), 7.35 (m, 2H), 6.86 (q, 4H), 6.04 (t, 1H), 4.79 (m, 1H), 4.06 (t, 1H), 3.88 (m, 5H), 3.74 (s, 3H), 3.70 (m, 8H), 2.01 (s, 3H).

EXAMPLE 17

Preparation of (S)-[N-3-(4-(2-(4-Methoxyacetylpiperazin-1-yl)pyrimidin-5-yl)-3-fluorophenyl)-2-oxo-5-oxazolidinyl]methyl Acetamide Except for starting with 13 μl of methoxyacetyl chloride instead of acetyl chloride, the same procedure as in Example 6 was conducted to prepare the title compound. 32 mg.

$^1$H-NMR (CDCl$_3$) 8.48 (d, 2H), 7.56 (dd, 1H), 7.35 (m, 2H), 6.35 (t, 1H), 4.79 (m, 1H), 4.14 (s, 2H), 4.06 (t, 1H), 3.87 (m, 5H), 3.65 (m, 4H), 3.58 (m, 2H), 3.42 (s, 3H), 2.01 (s, 3H).

EXAMPLE 18

Preparation of (S)-[N-3-(4-(2-(4-Acryloylpiperazin-1-yl)pyrimidin-5-yl)-3-fluorophenyl)-2-oxo-5-oxazolidinyl]methyl Acetamide Except for starting with 14 μl of acryloyl chloride instead of acetyl chloride, the same procedure as in Example 6 was conducted to prepare the title compound. 28 mg.

¹H-NMR (CDCl₃) δ 8.49 (d, 2H), 7.56 (dd, 1H), 7.35 (m, 2H), 6.62 (dd, 1H), 6.36 (dd, 1H), 6.09 (t, 1H), 5.75 (dd, 1H), 4.80 (m, 1H), 4.06 (t, 1H), 3.97 (m, 4H), 3.85 (m, 3H), 3.68 (m, 4H), 2.01 (s, 3H).

EXAMPLE 19

Preparation of (S)-[N-3-(4-(2-(4-Ethoxyoxoacetylpiperazin-1-yl)pyrimidin-5-yl)-3-fluorophenyl)-2-oxo-5-oxazolidinyl]methyl Acetamide Except for starting with 16 μl of ethylchlorooxoacetate instead of acetyl chloride, the same procedure as in Example 6 was conducted to prepare the title compound. 30 mg.

¹H-NMR (CDCl₃) δ 8.50 (d, 2H), 7.56 (dd, 1H), 7.35 (m, 2H), 7.13 (m, 3H), 6.03 (t, 1H), 4.79 (m, 1H), 4.37 (q, 2H), 4.06 (t, 1H), 3.95 (m, 4H), 3.75 (m, 5H), 3.51 (m, 2H), 2.01 (s, 3H), 1.37 (t, 3H).

EXAMPLE 20

Preparation of (S)-[N-3-(4-(2-(4-Nicotinoylpiperazin-1-yl)pyrimidin-5-yl)-3-fluorophenyl)-2-oxo-5-oxazolidinyl]methyl Acetamide Except for starting with 26 mg of nicotinoyl chloride instead of acetyl chloride, the same procedure as in Example 6 was conducted to prepare the title compound. 22 mg.

¹H-NMR (CDCl₃) 8.70 (s, 2H), 8.50 (s, 2H), 7.82 (d, 1H), 7.56 (dd, 1H), 7.35 (m, 2H), 5.99 (t, 1H), 4.80 (m, 1H), 4.06 (t, 1H), 3.95 (m, 4H), 3.75 (m, 7H), 2.01 (s, 3H).

EXAMPLE 21

Preparation of (S)-[N-3-(4-(2-(4-Pivaloylpiperazin-1-yl)pyrimidin-5-yl)-3-fluorophenyl)-2-oxo-5-oxazolidinyl]methyl Acetamide Except for starting with 17.4 μl of pivaloylchloride instead of acetylchloride, the title compound was prepared in a manner similar to that of Example 6. 30 mg.

¹H-NMR (CDCl₃) 8.49 (d, 2H), 7.56 (dd, 1H), 7.35 (m, 2H), 6.05 (t, 1H), 4.79 (m, 1H), 4.06 (t, 1H), 3.88 (m, 4H), 3.65 (m, 7H), 2.01 (s, 3H), 1.30 (s, 9H).

EXAMPLE 22

Preparation of (S)-[N-3-(4-(2-(4-t-Butylacetylpiperazin-1-yl)pyrimidin-5-yl)-3-fluorophenyl)-2-oxo-5-oxazolidinyl]methyl Acetamide Except for starting with 20 μl of t-butylacetyl chloride instead of acetylchloride, the title compound was prepared in a manner similar to that of Example 6. 20 mg.

¹H-NMR (CDCl₃) 8.48 (d, 2H), 7.56 (dd, 1H), 7.35 (m, 2H), 6.27 (t, 1H), 4.79 (m, 1H), 4.05 (t, 1H), 3.87 (m, 4H), 3.69 (m, 4H), 3.58 (m, 3H), 2.01 (s, 3H), 1.05 (s, 9H).

EXAMPLE 23

Preparation of (S)-[N-3-(4-(2-(4-(2,5-Dimethoxyphenyl)acetylpiperazin-1-yl)pyrimidin-5-yl)-3-fluorophenyl)-2-oxo-5-oxazolidinyl]methyl Acetamide Except for starting with 30 mg of 2,5-dimethoxyphenylacetyl chloride instead of acetylchloride, the title compound was prepared in a manner similar to that of Example 6. 36 mg.

¹H-NMR (CDCl₃) δ 8.48 (d, 2H), 7.55 (dd, 1H), 7.33 (m, 2H), 6.84 (m, 1H), 6.76 (m, 2H), 6.03 (t, 1H), 4.79 (m, 1H), 4.06 (t, 1H), 3.78 (s, 3H), 3.72 (s, 3H), 2.00 (s, 3H).

EXAMPLE 24

Preparation of (S)-[N-3-(4-(2-(4-(3,3-Dimethylacryloyl)piperazine-1-yl)pyrimidin-5-yl)-3-fluorophenyl)-2-oxo-5-oxazolidinyl]methyl Acetamide Except for starting with 16 μl of 3,3-dimethylacryloyl chloride instead of acetylchloride, the title compound was prepared in a manner similar to that of Example 6. 20 mg.

¹H-NMR (CDCl₃) δ 8.49 (d, 2H), 7.56 (dd, 1H), 7.34 (m, 2H), 6.04 (t, 1H), 5.81 (s, 1H), 4.79 (m, 1H), 4.06 (t, 1H), 3.85 (m, 5H), 3.70 (m, 5H), 3.62 (m, 2H), 2.01 (s, 3H).

EXAMPLE 25

Preparation of (S)-[N-3-(4-(2-(4-(2,6-Dimethoxybenzoyl)piperazine-1-yl)pyrimidin-5-yl)-3-fluorophenyl)-2-oxo-5-oxazolidinyl]methyl Acetamide Except for starting with 29 mg of 2,6-dimethoxybenzoyl chloride instead of acetylchloride, the title compound was prepared in a manner similar to that of Example 6. 27 mg.

¹H-NMR (CDCl₃) 8.48 (d, 2H), 7.56 (dd, 1H), 7.35 (m, 3H), 6.58 (d, 2H), 6.04 (t, 1H), 4.79 (m, 1H), 4.06 (t, 1H), 3.95 (m, 4H), 3.75 (m, 5H), 3.31 (m, 2H), 2.01 (s, 3H).

EXAMPLE 26

Preparation of (S)-[N-3-(4-(2-(4-(2-Trifluoromethylbenzoyl)piperazin-1-yl)pyrimidin-5-yl)-3-fluorophenyl)-2-oxo-5-oxazolidinyl]methyl Acetamide Except for starting with 29 μl of 2-trifluoromethylbenzoyl chloride instead of acetylchloride, the title compound was prepared in a manner similar to that of Example 6. 36 mg.

¹H-NMR (CDCl₃) 8.47 (d, 2H), 7.74 (d, 1H), 7.57 (m, 3H), 7.38 (m, 2H), 7.34 (m, 1H), 6.07 (t, 1H), 4.79 (m, 1H), 4.06 (t, 1H), 3.95 (m, 6H), 3.64 (m, 2H) 3.25 (m, 2H), 2.01 (s, 3H).

EXAMPLE 27

Preparation of (S)-[N-3-(4-(2-(4-(4-Trifluoromethylbenzoyl)piperazin-1-yl)pyrimidin-5-yl)-3-fluorophenyl)-2-oxo-5-oxazolidinyl]methyl Acetamide Except for starting with 40 μl of 4-trifluoromethylbenzoyl chloride instead of acetylchloride, the title compound was prepared in a manner similar to that of Example 6. 35 mg.

¹H-NMR (CDCl₃) δ 8.50 (d, 2H), 7.72 (d, 2H), 7.57 (m, 3H), 7.35 (m, 2H), 6.01 (t, 1H), 4.79 (m, 1H), 4.09 (t, 1H), 3.95 (m, 4H), 3.75 (m, 7H), 2.01 (s, 3H).

EXAMPLE 28

Preparation of (S)-[N-3-(4-(2-(4-Phenylacetylpiperazin-1-yl)pyrimidin-5-yl)-3-fluorophenyl)-2-oxo-5-oxazolidinyl]methyl Acetamide Except for starting with 20 μl of phenylacetyl chloride instead of acetylchloride, the title compound was prepared in a manner similar to that of Example 6. 23 mg.

EXAMPLE 29

Preparation of (S)-[N-3-(4-(2-(4-(3,5-Dinitrobenzoyl)piperazin-1-yl)pyrimidin-5-yl)-3-fluorophenyl)-2-oxo-5-oxazolidinyl]methyl Acetamide Except for starting with 20 μl of 3,5-dinitrobenzoyl chloride instead of acetylchloride, the title compound was prepared in a manner similar to that of Example 6. 20 mg.

$^1$H-NMR (CDCl$_3$) δ 8.50 (d, 2H), 8.30 (d, 1H), 7.62 (d, 1H), 7.56 (dd, 1H), 7.35 (m, 1H), 7.27 (dd, 1H), 6.02 (t, 1H), 4.79 (m, 1H), 4.06 (t, 1H), 2.01 (s, 3H).

EXAMPLE 30

Preparation of (S)-[N-3-(4-(2-(4-Crotonylpiperazin-1-yl)pyrimidin-5-yl)-3-fluorophenyl)-2-oxo-5-oxazolidinyl]methyl Acetamide Except for starting with 14 μl of crotonyl chloride instead of acetylchloride, the title compound was prepared in a manner similar to that of Example 6.25 mg.

$^1$H-NMR (CDCl$_3$) δ 8.49 (d, 2H), 7.56 (dd, 1H), 7.35 (m, 2H), 6.69 (m, 1H), 6.28 (dd, 1H), 6.01 (t, 1H), 4.79 (m, 1H), 4.06 (t, 1H), 3.95 (m, 4H), 3.75 (m, 7H), 2.01 (s, 3H), 1.90 (dd, 3H).

EXAMPLE 31

Preparation of (S)-[N-3-(4-(2-(4-Trichloroacetylpiperazin-1-yl)pyrimidin-5-yl)-3-fluorophenyl)-2-oxo-5-oxazolidinyl]methyl Acetamide Except for starting with 32 μl of trichloroacetyl chloride instead of acetylchloride, the title compound was prepared in a manner similar to that of Example 6. 25 mg.

$^1$H-NMR (CDCl$_3$) δ 8.50 (d, 2H), 7.56 (dd, 1H), 7.37 (m, 2H), 6.03 (t, 1H), 4.80 (m, 1H), 4.06 (t, 1H), 3.95 (m, 4H), 3.75 (m, 7H), 2.01 (s, 3H).

EXAMPLE 32

Preparation of (S)-[N-3-(4-(2-(4-n-Valerylpiperazin-1-yl)pyrimidin-5-yl)-3-fluorophenyl)-2-oxo-5-oxazolidinyl]methyl Acetamide Except for starting with 25 μl of valeryl chloride instead of acetylchloride, the title compound was prepared in a manner similar to that of Example 6.35 mg.

EXAMPLE 33

Preparation of (S)-[N-3-(4-(2-(4-(1-Bromoethylcarbonyl)piperazin-1-yl)pyrimidin-5-yl)-3-fluorophenyl)-2-oxo-5-oxazolidinyl]methyl Acetamide Except for starting with 12 μl of bromoethylcarbonyl chloride instead of acetylchloride, the title compound was prepared in a manner similar to that of Example 6. 10 mg.

EXAMPLE 34

Preparation of (S)-[N-3-(4-(2-(4-Phenoxycarbonylpiperazin-1-yl)pyrimidin-5-yl)-3-fluorophenyl)-2-oxo-5-oxazolidinyl]methyl Acetamide Except for starting with 18 μl of phenylchloroformate instead of acetylchloride, the title compound was prepared in a manner similar to that of Example 6.15 mg.

$^1$H-NMR (CDCl$_3$) δ 8.50 (d, 2H), 7.56 (dd, 1H), 7.35 (m, 4H), 7.13 (m, 3H), 6.79 (t, 1H), 4.79 (t, 1H), 4.06 (t, 1H), 3.95 (m, 4H), 3.75 (m, 7H), 2.01 (s, 3H).

EXAMPLE 35

Preparation of (S)-[N-3-(4-(2-(4-Benzyloxycarbonylbenzyloxycarbonylpiperazin-1-yl)pyrimidin-5-yl)-3-fluorophenyl)-2-oxo-5-oxazolidinyl]methyl Acetamide Except for starting with 17 μl of benzylcarbonyl chloride instead of acetylchloride, the title compound was prepared in a manner similar to that of Example 6. 22 mg.

$^1$H-NMR (CDCl$_3$) δ 8.47 (d, 2H), 7.55 (dd, 1H), 6.35 (t, 4H), 5.15 (s, 3H), 4.79 (m, 1H), 4.06 (t, 1H), 3.85 (m, 4H), 3.78 (dd, 1H), 3.58 (m, 4H), 2.01 (s, 3H).

EXAMPLE 36

Preparation of (S)-[N-3-(4-Pyridin-2-yl)-3-fluorophenyl]-2-oxo-5-oxazolidinyl]methyl Acetamide In 4 ml of dimethylformamide was dissolved 300 mg of (S)-[N-3-(4-trimethylstannyl-3-fluorophenyl)-2-oxo-5-oxazolidinyl]methyl acetamide which was then reacted with 0.14 ml of 2-bromopyridine in the presence of 0.25 ml of triethylamine with the catalytic aid of 0.2 g of dichlorobistriphenylphosphine palladium (II) at 100° C. with stirring after their addition at room temperature. After completion of the reaction, the reaction mixture was added with water and extracted with ethyl acetate. The organic layer thus separated was washed with brine, dehydrated, filtered and concentrated in vacuo. Through column chromatography, the concentrate was purified to the title compound. 50 mg.

EXAMPLE 37

Preparation of (S)-[N-3-(4-(2-Aminopyridin-5-yl)-3-fluorophenyl)-2-oxo-5-oxazolidinyl]methyl Acetamide With the exception of adding, instead of 2-bromopyridine, 5.0 g of 2-amino-5-iodopyridine2-bromopyridine as a starting material, the same procedure as in Example 36 was conducted to give the title compound. 15 g. Yield 45%.

$^1$H-NMR (DMSO-d$_6$) δ 8.26 (t, 1H), 8.08 (s, 1H), 7.52 (m, 3H), 7.32 (dd, 1H), 8.51 (d, 1H), 6.14 (s, 2H), 4.74 (m, 1H), 4.14 (t, 1H), 3.75 (dd, 1H), 3.41 (m, 2H), 1.85 (s, 3H).

EXAMPLE 38

Preparation of (S)-[N-3-(4-(3-Methoxycarbonylpyridin-5-yl)-3-fluorophenyl)-2-oxo-5-oxazolidinyl]methyl Acetamide In 2.4 ml of dimethylformamide was dissolved 200 mg of (S)-[N-3-(4-trimethylstannyl-3-fluorophenyl)-2-oxo-5-oxazolidinyl]methyl acetamide 200 mg which was then reacted with 260.3 mg of methyl 5-bromopyridine-3-carboxylate in the presence of 0.17 ml of triethylamine with the catalytic aid of 135 mg of dichlorobistriphenylphosphine palladium (II) at 100° C. for 3 hours with stirring after their addition at room temperature. Water was then added to the reaction mixture, followed by the extraction with ethyl acetate. The organic layer was washed with brine, dehydrated, filtered and concentrated in vacuo. Purification of the concentrate through column chromatography provided the title compound. 60 mg.

¹H-NMR (CDCl₃) δ 9.16 (d, 1H), 8.90 (t, 1H), 8.42 (m, 1H), 7.60 (dd, 1H), 7.45 (t, 1H), 7.30 (dd, 1H), 6.16 (bt, 1H), 4.81 (m, 1H), 4.10 (t, 1H), 3.96 (s, 3H), 3.81 (dd, 1H), 3.70 (m, 2H), 2.02 (s, 3H).

EXAMPLE 39

Preparation of (S)-[N-3-(4-(2-Acetylaminopyridin-5-yl)-3-fluorophenyl)-2-oxo-5-oxazolidinyl]methyl Acetamide With the exception of using 260 mg of 2-amino-5-iodopyridine-2-bromopyridine as a starting material, the same procedure as in Example 38 was conducted to give the title compound. 45 mg.

¹H-NMR (DMSO-d₆) δ 8.48 (s, 1H), 8.28 (t, 1H), 8.15 (d, 1H), 7.98 (d, 1H), 7.64 (m, 1H), 7.43 (m, 1H), 4.76 (m, 1H), 4.18 (t, 1H), 3.79 (t, 1H), 3.42 (t, 2H), 2.10 (s, 3H), 1.82 (s, 3H).

EXAMPLE 40

Preparation of (S)-[N-3-(4-(2-Acetoxyacetylaminopyridin-5-yl)-3-fluorophenyl)-2-oxo-5-oxazolidinyl]methyl Acetamide In 5.6 ml of dimethylformamide was dissolved 467 mg of (S)-[N-3-(4-trimethylstannyl-3-fluorophenyl)-2-oxo-5-oxazolidinyl]methyl acetamide which was then reacted with 615 mg of 2-acetoxyacetylamino-5-bromopyridine in the presence of 0.39 ml of triethyl amine with the catalytic aid of 237 ml of dichlorobistriphenylphosphine palladium (II) at 100° C. for 4 hours with stirring after their addition at room temperature. Water was added to the reaction mixture, followed by extraction with ethyl acetate. The organic layer was washed with brine, dehydrated, filtered, and concentrated in vacuo. The concentrate was purified through column chromatography to give the title compound. 218 mg.

¹H-NMR (DMSO-d₆) δ 8.50 (s, 1H), 8.28 (t, 1H), 8.12 (d, 1H), 8.00 (d, 1H), 7.64 (m, 2H), 7.39 (m, 1H), 4.76 (m, 4H), 4.15 (t, 1H), 3.78 (dd, 1H), 3.42 (t, 2H), 2.10 (s, 3H), 1.82 (s, 3H).

EXAMPLE 41

Preparation of (S)-[N-3-(4-(2-Hydroxyacetylaminopyridin-5-yl)-3-fluorophenyl)-2-oxo-5-oxazolidinyl]methyl Acetamide In a mixture of methanol (1 ml) and chloroform (1 ml) was dissolved 100 mg of (S)-[N-3-(4-(2-acetoxyacetyl aminopyridin-5-yl)-3-fluorophenyl)-2-oxo-5-oxazolidinyl]methyl acetamide, following dropwise addition of a 1 N KOH solution at room temperature. Reaction was performed at room temperature for 1 hour with stirring. After being added with water, the reaction mixture was extracted with ethyl acetate. The organic layer thus separated was washed with brine, dehydrated, filtered and concentrated under vacuum to give a solid. It was recrystallized in methylenechloride and hexane to provide the title compound. 50 mg.

¹H-NMR (DMSO-d₆) δ 8.50 (s, 1H), 8.28 (d, 1H), 8.17 (d, 1H), 7.99 (d, 1H), 7.64 (m, 2H), 7.42 (dd, 1H), 5.75 (t, 1H), 4.76 (m, 1H), 4.13 (t, 1H), 4.05 (d, 2H), 3.79 (dd, 1H), 3.42 (t, 2H), 1.83 (s, 3H).

EXAMPLE 42

Preparation of (S)-[N-3-(4-(2-Imidazol-1-ylpyridin-5-yl)-3-fluorophenyl)-2-oxo-5-oxazolidinyl]methyl Acetamide With the exception of starting with 2-imidazolyl-5-bromopyridine, the same procedure as in Example 38 was carried out to give the title compound.

¹H-NMR (CDCl₃) δ 8.61 (s, 1H), 8.39 (s, 1H), 8.00 (dd, 1H), 7.87 (s, 1H), 7.61 (dd, 1H), 7.49 (m, 2H), 7.32 (dd, 1H), 7.21 (s, 1H), 6.13 (t, 1H), 4.80 (m, 1H), 4.08 (t, 1H), 3.81 (dd, 1H), 3.61 (m, 2H), 2.02 (s, 3H).

EXAMPLE 43

Preparation of (S)-[N-3-(4-(2-(4-Morpholinyl)-pyridin-5-yl)-3-fluorophenyl)-2-oxo-5-oxazolidinyl] methyl Acetamide With the exception of starting with 2-(4-morpholinyl)-5-bromopyridine, the same procedure as in Example 38 was carried out to give the title compound.

¹H-NMR (CDCl₃) δ 8.31 (s, 1H), 7.87 (dd, 1H), 7.50 (dd, 1H), 7.38 (t, 1H), 7.20 (dd, 1H), 6.65 (d, 1H), 6.55 (t, 1H), 4.79 (m, 1H), 4.04 (t, 1H), 3.81 (m, 5H), 3.62 (m, 2H), 3.52 (m, 4H), 2.00 (s, 3H).

EXAMPLE 44

Preparation of (S)-[N-3-(4-(2-Triphenylmethylaminopyridin-5-yl)-3-fluorophenyl)-2-oxo-5-oxazolidinyl]methyl Acetamide With the exception of starting with 2-triphenylmethylamino-5-bromopyridine, the same procedure as in Example 38 was carried out to give the title compound.

EXAMPLE 45

Preparation of (S)-[N-3-(4-(2-Methoxypyridin-5-yl)-3-fluorophenyl)-2-oxo-5-oxazolidinyl]methyl Acetamide In 5 ml of dimethylformamide was dissolved 430 mg of (S)-[N-3-(4-trimethylstannyl-3-fluorophenyl)-2-oxo-5-oxazolidinyl]methyl acetamide which was then reacted with 610 mg of 2-methoxy-5-iodopyridine in the presence of 0.36 ml of triethyl amine with the catalytic aid of 292 mg of dichlorobistriphenylphosphine palladium (II) at 100° C. for 2 hours after the addition of the reactants at room temperature. Water was then added to the reaction mixture, followed by extraction with ethyl acetate. The organic layer was washed with brine, dehydrated, filtered and concentrated in vacuo. The concentrate was purified by column chromatography to give the title compound. 200 mg.

¹H-NMR (CDCl₃) δ 8.25 (s, 1H), 7.70 (m, 1H), 7.51 (dd, 1H), 7.38 (t, 1H), 7.22 (m, 1H), 6.78 (d, 1H), 6.65 (t, 1H), 4.80 (m, 1H), 4.08 (t, 1H), 3.97 (s, 3H), 3.81 (dd, 1H), 3.65 (m, 2H), 2.00 (s, 3H).

EXAMPLE 46

Preparation of (S)-[N-3-(4-(2-Methoxyacetylaminopyridin-5-yl)-3-fluorophenyl)-2-oxo-5-oxazolidinyl]methyl Acetamide In 2.5 ml of dimethylformamide was dissolved 200 mg of (S)-[N-3-(4-trimethylstannyl-3-fluorophenyl)-2-oxo-5-oxazolidinyl]methyl acetamide and the solution was added with 295 mg of methoxyacetylamino-5-bromdpyridine, 0.17 ml of triethyl amine, and 135 mg of dichlorobistriphenylphosphine palladium (II). Reaction was carried out at 100° C. for 2 hours with stirring. Water was added to the reaction mixture, followed by extraction with ethyl acetate. The organic layer thus separated was washed with brine, dehydrated, filtered, and concentrated under vacuum. Column chromatography of the concentrate provided the title compound. 47 mg.

$^1$H-NMR (DMSO-d$_6$) δ 8.50 (s, 1H), 8.20 (t, 1H), 8.15 (d, 1H), 7.97 (d, 1H), 7.64 (m, 2H), 7.42 (m, 1H), 4.78 (m, 1H), 4.16 (t, 1H), 4.09 (s, 3H), 3.79 (dd, 1H), 3.42 (t, 2H), 3.37 (s, 3H), 1.83 (s, 3H).

EXAMPLE 47

Preparation of (S)-[N-3-(4-(2-(4-Triphenylmethylpiperazin-1-yl)pyridin-5-yl)-3-fluorophenyl)-2-oxo-5-oxazolidinyl]methyl Acetamide With the exception of starting with 2-(4-triphenylmethylpiperazin-1-yl)-5-bromopyridine, the title compound was prepared in a manner similar to that of Example 38.

EXAMPLE 48

Preparation of (S)-[N-3-(4-(2-Triphenylmethylaminopyridin-5-yl)-3-fluorophenyl)-2-oxo-5-oxazolidinyl]methyl Acetamide Hydrochloride With the exception of starting with 2-triphenylmethylamino-5-bromopyridine, the title compound was prepared in a manner similar to that of Example 38.

EXAMPLE 49

Preparation of (S)-[N-3-(4-(2-Azidopyridin-5-yl)-3-fluorophenyl)-2-oxo-5-oxazolidinyl]methyl Acetamide With the exception of starting with 2-azido-5-bromopyridine, the title compound was prepared in a manner similar to that of Example 38.

EXAMPLE 50

Preparation of (S)-[N-3-(4-(2-Hydroxymethylpyridin-4-yl)-3-fluorophenyl)-2-oxo-5-oxazolidinyl]methyl Acetamide In a mixture of ethanol (3 ml) and tetrahydrofuran (1.3 ml) was dissolved 100 mg of (S)-[N-3-(4-(2-methoxycarbonylpyridin-4-yl)-3-fluorophenyl)-2-oxo-5-oxazolidinyl]methyl acetamide and the solution was added with 29.3 mg of sodium borohydride and 32.8 mg of lithium chloride at room temperature. After being reacted at room temperature for 2 hours with stirring, the reaction mixture was added with ethyl acetate. The organic layer thus separated was washed with sodium hydrogen carbonate (NaHCO$_3$) and brine, dried, filtered, and concentrated in vacuo. Purification of the concentrate in ethyl acetate provided the title compound. 35 mg.

$^1$H-NMR (DMSO-d$_6$) δ 8.54 (d, 1H), 8.28 (t, 2H), 7.70 (m, 3H), 7.45 (m, 2H), 5.52 (t, 1H), 4.76 (t, 1H), 4.62 (d, 2H), 4.07 (t, 1H), 3.79 (dd, 1H), 3.42 (t, 2H), 1.83 (s, 3H).

EXAMPLE 51

Preparation of (S)-[N-3-(4-(2-Methoxycarbonylpyridin-4-yl)-3-fluorophenyl)-2-oxo-5-oxazolidinyl]methyl Acetamide In 9.5 ml of dimethylformamide was dissolved 790 mg of (S)-[N-3-(4-trimethylstannyl-3-fluorophenyl)-2-oxo-5-oxazolidinyl]methyl acetamide which was then reacted with 1 g of methyl 4-iodopyridin-2-carboxylate in the presence of 0.67 ml of triethyl amine with the catalytic aid of 533 mg of dichlorobistriphenylphosphine palladium (II) at 100° C. for 3 hours after the addition of the reactants at room temperature.

$^1$H-NMR (DMSO-d$_6$) δ 8.78 (d, 1H), 8.27 (m, 2H), 7.70 (m, 3H), 7.47 (dd, 2H), 4.76 (m, 1H), 4.20 (t, 1H), 4.28 (s, 3H), 3.90 (dd, 1H), 3.43 (t, 2H), 1.83 (s, 3H).

EXAMPLE 52

Preparation of (S)-[N-3-(4-(2-Dimethylaminocarbonylpyridin-4-yl)-3-fluorophenyl)-2-oxo-5-oxazolidinyl]methyl Acetamide In 5 ml of dimethylformamide was dissolved 380 mg of (S)-[N-3-(4-trimethylstannyl-3-fluorophenyl)-2-oxo-5-oxazolidinyl]methyl acetamide and the solution was added with 300 mg of N,N-2-dimethylaminocarbonyl-4-iodopyridine, 0.32 mg of triethyl amine and 255 mg of dichlorobistriphenylphosphine at room temperature. Reaction was carried out at 100° C. for 2 hours with stirring. Water was added to the reaction mixture, followed by extraction with ethyl acetate. The organic layer thus separated was washed with brine, dehydrated, filtered and concentrated in vacuo. Purification of the concentrate through column chromatography gave the title compound. 91 mg.

$^1$H-NMR (DMSO-d$_6$) δ 8.63 (d, 1H), 8.27 (t, 1H), 7.70 (m, 4H), 7.45 (dd, 1H), 4.76 (m, 1H), 4.17 (t, 1H), 3.79 (dd, 1H), 3.42 (t, 2H), 3.01 (s, 3H), 2.96 (s, 3H), 1.83 (s, 3H).

EXAMPLE 53

Preparation of (S)-[N-3-(4-(2-Hydroxypyridin-5-yl)-3-fluorophenyl)-2-oxo-5-oxazolidinyl]methyl Acetamide The title compound was prepared in a manner similar to that of Example 38, with the exception of using 2-hydroxy-5-bromopyridine as a starting material.

EXAMPLE 54

Preparation of (S)-[N-3-(4-(N-2-Dimethylaminoacetoxyacetylaminopyridin-4-yl)-3-fluorophenyl)-2-oxo-5-oxazolidinyl]methyl Acetamide In 2.5 ml of pyridine was dissolved 200 mg of (S)-[N-3-(4-(N-2-hydroxyacetylaminopyridin-4-yl)-3-fluorophenyl)-2-oxo-5-oxazolidinyl]methyl acetamide and the solution was added with 205 mg of N,N-dimethylglycine, 381 mg of 1-(3-dimethylaminopropyl)-3-ethylcarbodiimide hydrochloride 91 mg of 4-dimethylaminopyridine at room temperature. Reaction was carried out at room temperature for 15 hours with stirring. Water was added to the reaction mixture, followed by extraction with ethylacetate. The organic layer thus separated was washed with brine, dehydrated, filtered, and concentrated under vacuum. The concentrate was purified through column chromatography to obtain the title compound. 110 mg.

EXAMPLE 55

Preparation of (S)-[N-3-(4-(2-Methylaminopyridin-5-yl)-3-fluorophenyl)-2-oxo-5-oxazolidinyl]methyl Acetamide In 6 ml of tetrahydrofuran was dissolved 500 mg of (S)-[N-3-(4-trimethylstannyl-3-fluorophenyl)-2-oxo-5- oxazolidinyl]methyl acetamide which was then reacted with 564 mg of 2-methylamino-5-iodopyridine in the presence of 153 mg of lithium chloride 153 mg with the catalytic aid of 278 mg of tetrakistriphenylphosphine palladium (II) for 48 hours under reflux. Water was added to the reaction mixture which was then extracted with ethyl acetate. The organic layer thus separated was washed with brine, dehydrated, filtered, and concentrated under vacuum. The concentrate was purified by column chromatography to give the title compound. 181 mg.

$^1$H-NMR (DMSO-$d_6$) δ 8.26 (t, 1H), 8.16 (s, 1H), 7.58 (m, 2H), 7.35 (dd, 1H), 6.70 (dd, 1H), 6.50 (d, 1H), 4.74 (m, 1H), 4.17 (t, 1H), 3.79 (dd, 1H), 3.43 (t, 2H), 2.78 (d, 3H), 1.82 (s, 3H).

EXAMPLE 56

Preparation of (S)-[N-3-(4-(2-Dimethylaminopyridin-5-yl)-3-fluorophenyl)-2-oxo-5-oxazolidinyl]methyl Acetamide The title compound was prepared in a manner similar to that of Example 55, with the exception of using 2-dimethylamino-5-iodopyridine.

$^1$H-NMR (DMSO-$d_6$) δ 8.31 (m, 2H), 7.71 (dd, 1H), 7.60 (m, 3H), 7.34 (dd, 1H), 6.73 (d, 1H), 4.73 (m, 1H), 4.14 (t, 1H), 3.76 (dd, 1H), 3.42 (t, 2H), 3.05 (s, 6H), 1.82 (s, 3H).

EXAMPLE 57

Preparation of (S)-[N-3-(4-(2-Hydroxyacetylaminopyridin-5-yl)-3-fluorophenyl)-2-oxo-5-oxazolidinyl]methyl Acetamide Hydrochloride In a mixture of methanol and chloroform was dissolved 500 mg of (S)-[N-3-(4-(2-hydroxyacetylaminopyridin-5-yl)-3-fluorophenyl)-2-oxo-5-oxazolidinyl]methyl acetamide which was then reacted with 0.5 ml of hydrochloride at room temperature for 1 hour with stirring. The reaction mixture was concentrated under vacuum and the concentrate was purified many times with ethyl ether to give the title compound. 520 mg.

$^1$H-NMR (DMSO-$d_6$) δ 10.01 (s, 1H), 8.53 (s, 1H), 4.75 (m, 1H), 4.18 (t, 1H), 4.08 (s, 2H), 3.78 (dd, 1H), 3.42 (t, 2H), 1.83 (s, 3H).

EXAMPLE 58

Preparation of (S)-[N-3-(4-(2-Hydroxyacetylaminopyridin-5-yl)-3-fluorophenyl)-2-oxo-5-oxazolidinyl]methyl Acetamide Hydroxypropylmethylcellulose Multiploid In a solvent mixture of ethanol and methylene chloride, a mixture of (S)-[N-3-(4-(2-hydroxyacetylaminopyridin-5-yl)-3-fluorophenyl)-2-oxo-5-oxazolidinyl]methyl acetamide and hydroxypropylmethyl cellulose (HPMC) in a weight proportion of 2:1 was slowly dissolved. After 2 hours of stirring, the solvent was evaporized by use of spray drying to give the title compound.

EXAMPLE 59

Preparation of (S)-[N-3-(4-(2-Acetoxypyridin-5-yl)-3-fluorophenyl)-2-oxo-5-oxazolidinyl]methyl Acetamide The title compound was prepared in a manner similar to that of Example 38, with the exception of using 2-acetoxy-5-bromopyridine as a starting material.

EXAMPLE 60

Preparation of (S)-[N-3-(4-(2-Methoxymethyloxypyridin-5-yl)-3-fluorophenyl)-2-oxo-5-oxazolidinyl]methyl Acetamide The title compound was prepared in a manner similar to that of Example 38, with the exception of using 2-methoxyoxy-5-bromopyridine as a starting material.

EXAMPLE 61

Preparation of (S)-[N-3-(4-(2-Methanesulfonyloxypyridin-5-yl)-3-fluorophenyl)-2-oxo-5-oxazolidinyl]methyl Acetamide The title compound was prepared in a manner similar to that of 38, with the exception of using methylsulfonyloxy-5-bromopyridine as a starting material.

EXAMPLE 62

Preparation of (S)-[N-3-(4-(2-Aminocarbonylpyridin-4-yl)-3-fluorophenyl)-2-oxo-5-oxazolidinyl]methyl Acetamide The title compound was prepared in a manner similar to that of Example 38, with the exception of using 2-aminocarbonyl-4-bromopyridine as a starting material.

EXAMPLE 63

Preparation of (S)-[N-3-(4-(2-Dimethylaminoacetoxymethylpyridin-4-yl)-3-fluorophenyl)-2-oxo-5-oxazolidinyl]methyl Acetamide In 2 ml of pyridine was dissolved 155 mg of (S)-[N-3-(4-(2-hydroxymethylpyridin-4-yl)-3-fluorophenyl)-2-oxo-5-oxazolidinyl]methyl acetamide and the solution was dropwise added with 318 mg of N,N-dimethylglycine, 662 mg of 1-(3-dimethylaminopropyl)-3-ethylcarbodiimide hydrochloride 158 mg of 4-dimethylaminopyridine individually and stirred for 15 hours at room temperature. Water was then added to the reaction mixture, followed by extraction with ethyl acetate. The organic layer was washed with brine, dehydrated, filtered and concentrated in vacuo. The concentrate was subjected to column chromatography to give the title compound. 113 mg.

$^1$H-NMR (CDCl$_3$) δ 8.48 (d, 1H), 5.18 (s, 2H), 4.75 (m, 1H), 4.00 (t, 1H), 3.76 (dd, 1H), 3.60 (bs, 2H), 3.19 (s, 2H), 2.25 (s, 6H), 1.93 (s, 3H).

EXAMPLE 64

Preparation of (S)-[N-3-(4-(2-(2-Hydroxyethyl)aminocarbonylpyridin-4-yl)-3-fluorophenyl)-2-oxo-5-oxazolidinyl]methyl Acetamide In 3 ml of dimethylformamide was dissolved 245 mg of (S)-[N-3-(4-trimethylstannyl-3-fluorophenyl)-2-oxo-5-oxazolidinyl]methyl acetamide 245 mg which was then reacted with 345 mg of 2(2-hydroxyethyl)aminocarbonyl-4-iodopyridine in the presence of 0.21 ml of triethyl amine with the catalytic aid of 166 mg of dichlorobistriphenylphosphine palladium (II) at 100° C. for 3 hours after the addition of the reactants at room temperature. Water was then added to the reaction mixture, followed by extraction with ethyl acetate. The organic layer thus separated was washed with brine, dehydrated, filtered, and concentrated under vacuum.

Through column chromatography, the concentrate was purified to the title compound. 60 mg.

$^1$H-NMR (DMSO-$d_6$) δ 8.69 (d, 1H), 8.27 (t, 1H), 8.19 (s, 1H), 7.81 (m, 1H), 7.70 (m, 1H), 7.45 (dd, 2H), 4.79 (m, 1H), 4.17 (t, 1H), 3.79 (dd, 1H), 3.51 (t, 2H), 3.43 (m, 4H), 1.83 (s, 3H).

EXAMPLE 65

Preparation of (S)-[N-3-(4-(2-N,N-di(2-Hydroxyethyl)aminocarbonylpyridin-4-yl)-3-fluorophenyl)-2-oxo-5-oxazolidinyl]methyl Acetamide Starting with N,N-di(2-hydroxyethyl)aminocarbonyl-4-iodopyridine, the title compound was prepared in a manner similar to that of Example 64.

$^1$H-NMR (DMSO-$d_6$) δ 8.60 (d, 1H), 8.26 (t, 1H), 7.64 (m, 4H), 7.45 (m, 1H), 4.80 (m, 3H), 4.17 (t, 1H), 3.79 (dd, 1H), 3.54 (m, 10H), 1.83 (s, 3H).

EXAMPLE 66

Preparation of (S)-[N-3-(4-(2-Piperazin-1-ylpyridin-5-yl)-3-fluorophenyl)-2-oxo-5-oxazolidinyl]methyl Acetamide Hydrochloride In tetrahydrofuran, 200 mg of (S)-[N-3-(4-(2-(4-triphenylmethylpiperazin-1-yl)pyridin-5-yl)-3-fluorophennyl)-2-oxo-5-oxazolidinyl]methyl acetamide was reacted with 1 ml of a 1N HCl solution at room temperature for one day with stirring to give a solid which was then filtered. Washing the filtrate with tetrahydrofuran and ether provided the title compound. 110 mg. Yield 88%.

EXAMPLE 67

Preparation of (S)-[N-3-(4-(2-(4-Acetoxyacetylpiperazin-1-yl)pyridin-5-yl)-3-fluorophenyl)-2-oxo-5-oxazolidinyl]methyl Acetamide In tetrahydrofuran was dissolved 30 mg of (S)-[N-3-(4-(2-piperazin-1-ylpyridin-5-yl)-3-fluorophenyl)-2-oxo-5-oxazolidinyl]methyl acetamide which was then acetylated with 16 μl of acetoxyacetyl chloride in the presence of 30 Ml of triethyl amine at room temperature for 20 min with stirring. Water was then added to the reaction mixture, followed by extraction with chloroform. The organic layer thus separated was washed with brine, dehydrated, filtered, and concentrated in vacuo. The concentrate was purified through column chromatography to provide the title compound. 23 mg.

EXAMPLE 68

Preparation of (S)-[N-3-(4-(2-(4-Benzyloxyacetylpiperazin-1-yl)pyridin-5-yl)-3-fluorophenyl)-2-oxo-5-oxazolidinyl]methyl Acetamide Starting with benzyloxyacetylpiperazinyl-5-bromopyridine, the title compound was prepared in a manner similar to that of Example 38.

EXAMPLE 69

Preparation of (S)-[N-3-(4-(2-(4-Hydroxyacetylpiperazin-1-yl)pyridin-5-yl)-3-fluorophenyl)-2-oxo-5-oxazolidinyl]methyl Acetamide In methanol, 220 mg of the compound prepared in Example 68 was reacted with 1 ml of a 1 N KOH solution at room temperature with stirring. After removal of excess methanol by vacuum concentration, water was added to the residue, followed by extraction with chloroform. The organic layer thus separated was dehydrated, filtered, and concentrated under vacuum. The concentrate was subjected to column chromatography to provide the title compound. 189 mg.

$^1$H-NMR (CDCl$_3$) δ 8.35 (s, 1H), 7.70 (d, 1H), 7.50 (dd, 1H), 7.37 (t, 1H), 7.27 (dd, 1H), 6.70 (d, 1H), 4.74 (m, 1H), 4.21 (d, 2H), 4.06 (t, 1H), 3.80 (m, 3H), 3.62 (m, 6H), 3.39 (m, 2H), 2.01 (s, 3H).

EXAMPLE 70

Preparation of (S)-[N-3-(4-(2-(4-Dimethylaminoacetoxyacetylpiperazin-1-yl)pyridin-5-yl)-3-fluorophenyl)-2-oxo-5-oxazolidinyl]methyl Acetamide Starting with (S)-[N-3-(4-(2-(4-hydroxyacetylpiperazin-1-yl)pyridin-5-yl)-3-fluorophenyl)-2-oxo-5-oxazolidinyl] methyl acetamide, the title compound was prepared in a manner similar to that of Example 63.

$^1$H-NMR (DMSO-$d_6$) δ 8.34 (s, 1H), 7.53 (m, 1H), 7.37 (dd, 1H), 7.33 (t, 1H), 7.26 (dd, 1H), 6.72 (d, 1H), 5.80 (t, 1H), 4.83 (m, 3H), 3.79 (m, 7H), 3.54 (t, 4H), 3.33 (d, 2H), 2.40 (s, 6H), 2.01 (s, 3H).

EXAMPLE 71

Preparation of (S)-[N-3-(4-(2-(4-Chloroacetylpiperazin-1-yl)pyridin-5-yl)-3-fluorophenyl)-2-oxo-5-oxazolidinyl]methyl Acetamide Starting with chloroacetyl chloride, the title compound was prepared in a manner similar to that of Example 67.

$^1$H-NMR (CDCl$_3$) δ 8.35 (s, 1H), 7.72 (m, 1H), 7.50 (dd, 1H), 7.41 (t, 1H), 6.74 (d, 1H), 6.16 (t, 1H), 4.79 (m, 1H), 3.79 (m, 13H), 2.02 (s, 3H).

EXAMPLE 72

Preparation of (S)-[N-3-(4-(2-(4-Acetylpiperazin-1-yl)pyridin-5-yl)-3-fluorophenyl)-2-oxo-5-oxazolidinyl]methyl Acetamide Starting with acetyl chloride, the title compound was prepared in a manner similar to that of Example 67.

EXAMPLE 73

Preparation of (S)-[N-3-(4-(2-(4-Methoxyacetylpiperazin-1-yl)pyridin-5-yl)-3-fluorophenyl)-2-oxo-5-oxazolidinyl]methyl Acetamide Starting with methoxyacetyl chloride, the title compound was prepared in a manner similar to that of Example 67.

EXAMPLE 74

Preparation of (S)-[N-3-(4-(2-(4-Morpholinylacetylpiperazin-1-yl)pyridin-5-yl)-3-fluorophenyl)-2-oxo-5-oxazolidinyl]methyl Acetamide In tetrahydrofuran was dissolved 30 mg of the compound prepared in Example 72, which was then reacted with 10.4 μl of morpholine in the presence of 25 μl of triethyl amine

EXAMPLE 75

Preparation of (S)-[N-3-(4-(2-(4-Methoxycarbonylmethylaminoacetylpiperazin-1-yl)pyridin-5-yl)-3-fluorophenyl)-2-oxo-5-oxazolidinyl]methyl Acetamide With the exception of using ethoxycarbonylmethylamino hydrochloride as a starting material, the same procedure as in Example 74 was conducted to give the title compound.

$^1$H-NMR (CDCl$_3$) δ 8.34 (s, 1H), 7.70 (dd, 1H), 7.54 (dd, 1H), 7.37 (t, 1H), 7.27 (dd, 1H), 6.68 (d, 1H), 5.98 (m, 1H), 4.76 (m, 1H), 4.06 (t, 1H), 3.90 (m, 1H), 3.782 (m, 8H), 3.63 (m, 3H), 3.52 (m, 5H), 3.39 (m, 1H), 2.01 (s, 3H).

EXAMPLE 76

Preparation of (S)-[N-3-(4-(2-(4-Ethoxycarbonylpiperidin-1-yl)pyridin-5-yl)-3-fluorophenyl)-2-oxo-5-oxazolidinyl]methyl Acetamide With the exception of using (4-ethoxycarbonylpiperidin-1-yl)-5-bromopyridine as a starting material, the same procedure as in Example 38 was conducted to give the title compound.

EXAMPLE 77

Preparation of (S)-[N-3-(4-(2-Azidomethylpyridin-4-yl)-3-fluorophenyl)-2-oxo-5-oxazolidinyl]methyl Acetamide With the exception of using 2-azidomethyl-4-bromopyridine as a starting material, the same procedure as in Example 38 was conducted to give the title compound.

$^1$H-NMR (DMSO-d$_6$) δ 8.67 (d, 1H), 8.27 (t, 1H), 7.72 (d, 1H), 7.68 (dd, 1H), 7.62 (s, 1H), 7.57 (d, 1H), 7.44 (dd, 1H), 4.76 (m, 1H), 4.56 (s, 3H), 4.17 (t, 1H), 3.79 (dd, 1H), 3.42 (t, 2H), 1.82 (s, 3H).

EXAMPLE 78

Preparation of (S)-[N-3-(4-(2-Imidazole-1-yl)methylpyridin-4-yl)-3-fluorophenyl)-2-oxo-5-oxazolidinyl]methyl Acetamide With the exception of using 2-imidazolylmethyl-4-bromopyridine as a starting material, the same procedure as in Example 38 was conducted to give the title compound.

$^1$H-NMR (DMSO-d$_6$) δ 8.55 (d, 1H), 8.18 (t, 1H), 7.68 (s, 1H), 7.58 (m, 2H), 7.40 (m, 2H), 7.28 (s, 1H), 7.16 (s, 1H), 6.81 (s, 1H), 5.22 (s, 2H), 4.68 (m, 1H), 4.16 (t, 1H), 3.69 (dd, 1H), 3.38 (t, 2H), 1.73 (s, 3H).

EXAMPLE 79

Preparation of (S)-[N-3-(4-(2-Morpholin-4-yl)methylpyridin-4-yl)-3-fluorophenyl)-2-oxo-5-oxazolidinyl]methyl Acetamide With the exception of using morpholinylmethyl-4-bromopyridine as a starting material, the same procedure as in Example 38 was conducted to give the title compound.

$^1$H-NMR (DMSO-d$_6$) δ 8.56 (d, 1H), 8.28 (t, 1H), 7.60 (m 3H), 7.45 (m, 2H), 4.78 (m, 1H), 4.17 (t, 1H), 3.77 (dd, 1H), 3.57 (m, 4H), 3.42 (m, 2H), 2.43 (m, 4H), 1.82 (s, 3H).

EXAMPLE 80

Preparation of (S)-[N-3-(4-(2-Acetylthiomethylpyridin-4-yl)-3-fluorophenyl)-2-oxo-5-oxazolidinyl]methyl Acetamide With the exception of using acetylthiomethyl-4-bromopyridine as a starting material, the same procedure as in Example 38 was conducted to give the title compound.

$^1$H-NMR (CDCl$_3$) δ 8.56 (d, 1H), 7.58 (dd, 1H), 7.49 (m, 2H), 7.32 (m, 2H), 6.03 (t, 1H), 4.81 (m, 1H), 4.28 (s, 2H), 4.09 (t, 1H), 3.81 (dd,1H), 3.69 (m, 2H), 2.35 (s, 3H), 2.01 (s, 3H).

EXAMPLE 81

Preparation of (S)-[N-3-(4-(2-Mercaptomethylpyridin-4-yl)-3-fluorophenyl)-2-oxo-5-oxazolidinyl]methyl Acetamide In methanol, 58 mg of the compound prepared in Example 82 was reacted with a 1 N NaOH solution at room temperature for 5 min with stirring. Water was added to the reaction mixture, followed by extraction with ethyl acetate. The organic layer thus separated was dehydrated, filtered, and concentrated under vacuum. Through column chromatography, the concentrate was purified to provide the title compound. 15 mg.

$^1$H-NMR (CDCl$_3$) δ 8.54 (d, 1H), 6.18 (t, 1H), 4.81 (m, 1H), 4.10 (t, 1H), 3.85 (d, 2H), 3.65 (dd, 2H), 2.01 (s, 3H).

EXAMPLE 82

Preparation of (S)-[N-3-(4-(2-(4-Methansulfonyloxyacetylpiperazin-1-yl)pyridin-5-yl)-3-fluorophenyl)-2-oxo-5-oxazolidinyl]methyl Acetamide In tetrahydrofuran, 30 mg of the compound prepared in Example, 70 was reacted with 15 µl of methanesulfonylchloride in the presence of 30 µl of triethylamine at room temperature for 1 hour with stirring. Water was added to the reaction mixture, followed by extraction with ethyl acetate. The organic layer thus separated was dehydrated, filtered, and concentrated under vacuum. Through column chromatography, the concentrate was purified to provide the title compound. 20 mg.

$^1$H-NMR (CDCl$_3$) δ 8.34 (s, 1H), 7.42 (dd, 1H), 7.52 (dd, 1H), 7.38 (t, 1H), 7.27 (dd, 1H), 6.72 (d, 1H), 6.17 (t, 1H), 4.94 (s, 1H), 4.81 (m, 1H), 4.10 (t, 1H), 3.75 (m, 13H), 3.24 (s, 3H), 2.01 (s, 3H).

EXAMPLE 83

Preparation of (S)-[N-3-(4-(2-(4-Acryloylpiperazin-1-yl)pyridin-5-yl)-3-fluorophenyl)-2-oxo-5-oxazolidinyl]methyl Acetamide With the exception of using acryloylchioride as a starting material, the same procedure as in Example 68 was carried out to provide the title compound.

EXAMPLE 84

Preparation of (S)-[N-3-(4-(2-(4-Ethoxyoxoacetylpiperazin-1-yl)pyridin-5-yl)-3-fluorophenyl)-2-oxo-5-oxazolidinyl]methyl Acetamide With the exception of using ethoxyacetyl chloride as a starting material, the same procedure as in Example 67 was carried out to provide the title compound.

EXAMPLE 85

Preparation of (S)-[N-3-(4-(2-(4-Nicotinoylpiperazin-1-yl)pyridin-5-yl)-3-fluorophenyl)-2-oxo-5-oxazolidinyl]methyl Acetamide With the exception of using nicotinoyl chloride as a starting material, the same procedure as in Example 67 was carried out to provide the title compound.

EXAMPLE 86

Preparation of (S)-[N-3-(4-(2-(4-Pivaloylpiperazin-1-yl)pyridin-5-yl)-3-fluorophenyl)-2-oxo-5-oxazolidinyl]methyl Acetamide With the exception of using pivaloylchloride as a starting material, the same procedure as in Example 67 was carried out to provide the title compound.

EXAMPLE 87

Preparation of (S)-[N-3-(4-(2-(4-Tetrabutylacetylpiperazin-1-yl)pyridin-5-yl)-3-fluorophenyl)-2-oxo-5-oxazolidinyl]methyl Acetamide With the exception of using tetrabutylacetylchloride as a starting material, the same procedure as in Example 67 was carried out to provide the title compound.

EXAMPLE 88

Preparation of (S)-[N-3-(4-(2-(4-Nicotinoyloxyacetylpiperazin-1-yl)pyridin-5-yl)-3-fluorophenyl)-2-oxo-5-oxazolidinyl]methyl Acetamide With the exception of using nicotinoylacetylchloride as a starting material, the same procedure as in Example 67 was carried out to provide the title compound.

EXAMPLE 89

Preparation of (S)-[N-3-(4-(2-(4-(2,5-Dimethoxyphenylacetyl)piperazin-1-yl)pyridin-5-yl)-3-fluorophenyl)-2-oxo-5-oxazolidinyl]methyl Acetamide With the exception of using 2,5-dimethoxyacetylchloride as a starting material, the same procedure as in Example 67 was carried out to provide the title compound.

EXAMPLE 90

Preparation of (S)-[N-3-(4-(2-(4-(3,3-Dimethylacryloyl)piperazine-1-yl)pyridin-5-yl)-3-fluorophenyl)-2-oxo-5-oxazolidinyl]methyl Acetamide With the exception of using 2,3-dimethylacryloylchloride as a starting material, the same procedure as in Example 67 was carried out to provide the title compound.

EXAMPLE 91

Preparation of (S)-[N-3-(4-(2-(4-(2,6-Dimethoxybenzoyl)piperazin-1-yl)pyridin-5-yl)-3-fluorophenyl)-2-oxo-5-oxazolidinyl]methyl Acetamide With the exception of using 2,6-dimethoxybenzoylchloride as a starting material, the same procedure as in Example 67 was carried out to provide the title compound.

EXAMPLE 92

Preparation of (S)-[N-3-(4-(2-(4-(2-Trifluoromethyl)benzoyl)piperazin-1-yl)pyridin-5-yl)-3-fluorophenyl]-2-oxo-5-oxazolidinyl]methyl Acetamide With the exception of using 2-trifluoromethylbenzoyl chloride as a starting material, the same procedure as in Example 67 was carried out to provide the title compound.

EXAMPLE 93

Preparation of (S)-[N-3-(4-(2-(4-(4-Trifluoromethyl)benzoyl)piperazin-1-yl)pyridin-5-yl)-3-fluorophenyl]-2-oxo-5-oxazolidinyl]methyl Acetamide With the exception of using 4-trifluoromethylbenzoyl chloride as a starting material, the same procedure as in Example 67 was carried out to provide the title compound.

EXAMPLE 94

Preparation of (S)-[N-3-(4-(2-(4-Benzylcarbonylpiperazin-1-yl)pyridin-5-yl)-3-fluorophenyl)-2-oxo-5-oxazolidinyl]methyl Acetamide With the exception of using phenyl acetyl chloride as a starting material, the same procedure as in Example 67 was carried out to provide the title compound.

EXAMPLE 95

Preparation of (S)-[N-3-(4-(2-(4-Crotonylpiperazin-1-yl)pyridin-5-yl)-3-fluorophenyl)-2-oxo-5-oxazolidinyl]methyl Acetamide With the exception of using crotonylchloride as a starting material, the same procedure as in Example 67 was carried out to provide the title compound.

EXAMPLE 96

Preparation of (S)-[N-3-(4-(2-(4-Trifluoromethylcarbonylpiperazin-1-yl)pyridin-5-yl)-3-fluorophenyl)-2-oxo-5-oxazolidinyl]methyl Acetamide With the exception of using trifluoroacetyl chloride as a starting material, the same procedure as in Example 67 was carried out to provide the title compound.

EXAMPLE 97

Preparation of (S)-[N-3-(4-(2-(4-n-Valerylpiperazin-1-yl)pyridin-5-yl)-3-fluorophenyl)-2-oxo-5-oxazolidinyl]methyl Acetamide With the exception of using valeryl chloride as a starting material, the same procedure as in Example 67 was carried out to provide the title compound.

EXAMPLE 98

Preparation of (S)-[N-3-(4-(2-(4-Phenyloxycarbonylpiperazin-1-yl)pyridin-5-yl)-3-fluorophenyl)-2-oxo-5-oxazolidinyl]methyl Acetamide With the exception of using phenylcarbonyl chloride as a starting material, the same procedure as in Example 67 was carried out to provide the title compound.

EXAMPLE 99

Preparation of (S)-[N-3-(4-(2-(4-Allyloxycarbonylpiperazin-1-yl)pyridin-5-yl)-3-fluorophenyl)-2-oxo-5-oxazolidinyl]methyl Acetamide With the exception of using allyloxycarbonyl chloride as a starting material, the same procedure as in Example 67 was carried out to provide the title compound.

EXAMPLE 100

Preparation of (S)-[N-3-(4-(2-(4-(1-Chloroethyl)oxycarbonylpiperazin-1-yl)pyridin-5-yl)-3-fluorophenyl)-2-oxo-5-oxazolidinyl]methyl Acetamide With the exception of using 1-chloroethyloxycarbonyl chloride as a starting material, the same procedure as in Example 67 was carried out to provide the title compound.

EXAMPLE 101

Preparation of (S)-[N-3-(4-(2-(4-(4-Nitrobenzyl)oxycarbonylpiperazin-1-yl)pyridin-5-yl)-3-fluorophenyl)-2-oxo-5-oxazolidinyl]methyl Acetamide With the exception of using 4-nitrobenzyloxycarbonyl chloride as a starting material, the same procedure as in Example 67 was carried out to provide the title compound.

EXAMPLE 102

Preparation of (S)-[N-3-(4-(2-(4-Benzyloxycarbonylpiperazin-1-yl)pyridin-5-yl)-3-fluorophenyl)-2-oxo-5-oxazolidinyl]methyl Acetamide With the exception of using benzyloxycarbonyl chloride as a starting material, the same procedure as in Example 67 was carried out to provide-the title compound.

EXAMPLE 103

Preparation of (S)-[N-3-(4-(2-(4-(9-Fluorenylmethyloxycarbonyl)piperazin-1-yl)pyridin-5-yl)-3-fluorophenyl)-2-oxo-5-oxazolidinyl]methyl Acetamide With the exception of using 9-fluorenylmethyloxycarbonyl chloride as a starting material, the same procedure as in Example 67 was carried out to provide the title compound.

EXAMPLE 104

Preparation of (S)-[N-3-(4-(2-(4-(2-Pyrimidinyl)piperazin-1-yl)pyridin-5-yl)-3-fluorophenyl)-2-oxo-5-oxazolidinyl]methyl Acetamide In dimethylacetamide was dissolved 20 mg of (S)-[N-3-(4-(2-piperazin-1-yl)pyridin-5-yl)-3-fluorophenyl]-2-oxo-5-oxazolidinyl]methyl acetamide which was then reacted with 38 mg of 2-bromopyridine in the presence of 63 $\mu$l of diisopropylethylamine at 50° C. for 20 hours with stirring. Purification with column chromatography provided the title compound. 39 mg.

EXAMPLE 105

Preparation of (S)-[N-3-(4-(2-(4-Methoxycarbonylmethylpiperazin-1-yl)pyridin-5-yl)-3-fluorophenyl)-2-oxo-5-oxazolidinyl]methyl Acetamide With the exception of using methoxycarbonylmethyl chloride as a starting material, the same procedure as in Example 67 was carried out to provide the title compound.

EXAMPLE 106

Preparation of (S)-[N-3-(4-(2-Fluoromethylpyridin-4-yl)-3-fluorophenyl)-2-oxo-5-oxazolidinyl]methyl Acetamide In methylene chloride was dissolved 68 mg of (S)-[N-3-(4-(2-hydroxymethylpyridin-4-yl)-3-fluorophenyl)-2-oxo-5-oxazolidinyl]methyl acetamide which was then reacted with 0.03 ml of diethylaminosulfurtrifluoride (DAST) in the presence of 0.04 ml of triethylamine at 0° C. for 2 hours with stirring. Water was added to the reaction mixture, followed by extraction with methylene chloride. The organic layer thus separated was dehydrated, filtered, and concentrated under vacuum. Through column chromatography, the concentrate was purified to provide the title compound. 20 mg.
$^1$H-NMR (CDCl$_3$) $\delta$ 8.45 (d, 1H), 5.25 (dd, 1H), 5.02 (dd, 1H), 4.93 (m, 1H), 4.02 (t, 1H), 4.17 (t, 1H), 3.87 (m, 1H), 3.63 (m, 2H), 2.04 (s, 3H).

EXAMPLE 107

Preparation of (S)-[N-3-(4-(2-Cyanomethylpyridin-4-yl)-3-fluorophenyl)-2-oxo-5-oxazolidinyl]methyl Acetamide Starting with 2-cyanomethyl-4-bromopyridine, the title compound was prepared in a manner similar to that of Example 38. $^1$H-NMR (CDCl$_3$) $\delta$ 8.59 (d, 1H), 6.10 (t, 1H), 4.82 (m, 1H), 4.13 (t, 1H), 3.98 (s, 2H), 3.79 (dd, 1H), 3.83 (dd, 2H), 3.68 (m, 2H), 2.02 (s, 3H).

EXAMPLE 108

Preparation of (S)-[N-3-(4-(2-methylpyridin-4-yl)-3-fluorophenyl)-2-oxo-5-oxazolidinyl]methyl Acetamide Starting with 2-methyl-4-bromopyridine, the title compound was prepared in a manner similar to that of Example 38.
$^1$H-NMR (DMSO-d$_6$) $\delta$ 8.54 (d, 1H), 8.27 (t, 1H), 4.78 (m, 1H), 4.17 (t, 1H), 3.80 (dd, 1H), 3.42 (t, 2H), 2.54 (s, 3H), 1.83 (s, 3H).

EXAMPLE 109

Preparation of (S)-[N-3-(4-(2-(4-(2-Hydroxy)ethylpiperazin-1-yl)pyridin-5-yl)-3-fluorophenyl)-2-oxo-5-oxazolidinyl]methyl Acetamide Starting with 2-hydroxyethylpiperazinyl-5-bromopyridine, the title compound was prepared in a manner similar to that of Example 38.

EXAMPLE 110

Preparation of (S)-[N-3-(4-(2-(4-(2-Acetoxy)ethylpiperazin-1-yl)pyridin-5-yl)-3-fluorophenyl)-2-oxo-5-oxazolidinyl]methyl Acetamide Starting with 2-acetoxyethylpiperazinyl-5-bromo pyridine, the title compound was prepared in a manner similar t o that of Example 38.

EXAMPLE 111

Preparation of (S)-[N-3-(4-(2-(4-Methoxycarbonylpiperazin-1-yl)pyridin-5-yl)-3-fluorophenyl)-2-oxo-5-oxazolidinyl]methyl Acetamide Starting with 4-methoxycarbonylpiperazinyl-5-bromopyridine, the title compound was prepared in a manner similar to that of Example 38.

EXAMPLE 112

Preparation of (S)-[N-3-(4-(2-(4-(2-Methanesulfonyloxy)ethylpiperazin-1-yl)pyridin-5-yl)-3-fluorophenyl)-2-oxo-5-oxazolidinyl]methyl Acetamide In tetrahydrofuran was dissolved 30 mg of the compound prepared in Example 76 and the solution was dropwise added with 15 μl of methanesulfonyl chloride and 30 μl of triethyl amine at room temperature. Reaction was conducted for 1 hour with stirring. Water was added to the reaction mixture, followed by extraction with ethyl acetate. The organic layer thus separated was dehydrated, filtered, and concentrated under vacuum. Through column chromatography, the concentrate was purified to provide the title compound. 20 mg.

EXAMPLE 113

Preparation of (S)-[N-3-(4-(2-(3-Hydroxymethylimidazol-1-yl)pyridin-5-yl)-3-fluorophenyl)-2-oxo-5-oxazolidinyl]methyl Acetamide Starting with 3-hydroxymethylimidazolyl-5-bromo pyridine, the title compound was prepared in a manner similar to that of Example 38.

$^1$H-NMR (DMSO-$d_6$) δ 9.80 (s, 1H), 8.79 (s, 1H), 8.31 (m, 3H), 8.11 (d, 1H), 7.64 (m, 2H), 7.45 (dd, 1H), 4.77 (m, 1H), 4.59 (s, 2H), 4.18 (t, 1H), 3.81 (dd, 1H), 3.43 (t, 2H), 1.83 (s, 3H).

EXAMPLE 114

Preparation of (S)-[N-3-(4-(2-Aminoacetylaminopyridin-5-yl)-3-fluorophenyl)-2-oxo-5-oxazolidinyl]methyl Acetamide In 100 ml of pyridine was dissolved 10.13 g of N-t-butoxycarbonylglycine and the solution was added with 5 g of 2-amino-5-bromopyridine, 13.85 g of 1-(3-dimethylaminopropyl)-3-ethylcarbodiimide hydrochloride and 7.06 g of 4-dimethylaminopyridine, individually at room temperature. Stirring was conducted for 15 hours at the same temperature. Water was added to the reaction mixture which was then extracted with ethyl acetate. The organic layer thus separated was washed with brine, dehydrated, filtered, and concentrated under vacuum to give 5.58 g of 2-(N-t-butoxycarbonylglycinylamino)-5-bromopyridine. This compound was dissolved, along with 5.82 g of (S)-[N-3-(4-trimethylstannyl-3-fluorophenyl)-2-oxo-5-oxazolidinyl]methyl acetamide, in 70 ml of dimethylformamide and added with 4.9 ml of triethyl amine and 2.97 g of dichlorobistriphenylphosphine palladium (II) at room temperature. Reaction was performed at 100° C. for 4 hours with stirring. Water was added to the reaction mixture, followed by extraction with ethyl acetate. The organic layer was washed with brine, dehydrated, filtered and concentrated under vacuum. Recrystallization of the concentrate provided 5.13 g of (S)-[N-3-(4-(2-(N-t-butoxycarbonylglycinylaminopyridin-5-yl)-3-fluorophenyl)-2-oxo-5-oxazolidinyl]methyl acetamide. This product was reacted with 1.65 ml of trimethylsilyl iodide in chloroform at room temperature for 30 min under a nitrogen atmosphere with stirring. Following the addition of chloroform, the organic layer thus separated was washed with brine, dehydrated, filtered, and concentrated in vacuo. The concentrate was purified through column chromatography to provide the title compound. 550 mg.

$^1$H-NMR (DMSO-$d_6$) δ 8.49 (s, 1H), 8.23 (m, 2H), 8.00 (m, 1H), 7.64 (m, 2H), 7.40 (dd, 1H), 4.75 (m, 1H), 4.16 (t, 1H), 3.77 (dd, 1H), 3.42 (t, 2H), 3.32 (s, 2H), 1.83 (s, 3H).

EXAMPLE 115

Preparation of (S)-[N-3-(4-(2-(4-Cyanopiperazin-1-yl)pyridin-5-yl)-3-fluorophenyl)-2-oxo-5-oxazolidinyl]methyl Acetamide In methanol, 500 mg of (S)-[N-3-(4-(2-piperazin-1-ylpyridin-5-yl)-3-fluorophenyl)-2-oxo-5-oxazolidinyl]methyl acetamide hydrochloride was reacted with 192 mg of cyanobromide in the presence of 295 mg of sodium acetate at room temperature for 3 hours with stirring. Chloroform was added to the reaction mixture, and the organic layer thus separated was washed with brine, dehydrated, filtered and concentrated under vacuum. The concentrate was purified through column chromatography to provide the title compound. 480 mg. Yield 90%.

EXAMPLE 116

Preparation of (S)-[N-3-(4-(2-(4-Carboxamideoximepiperazin-1-yl)pyridin-5-yl)-3-fluorophenyl)-2-oxo-5-oxazolidinyl]methyl Acetamide In ethanol was-dissolved 250 mg of (S)-[N-3-(4-(2-(4-cyanopiperazin-1-yl)pyridin-5-yl)-3-fluorophenyl)-2-oxo-5-oxazolidinyl]methyl acetamide and the solution was added with 79 mg of hydroxylamine hydrochloride and 211 mg of sodium carbonate. Reaction was conducted for 3 hours with refluxing. Following the addition of chloroform, the organic layer thus separated was washed with brine, dehydrated, filtered and concentrated in vacuo. The concentrate was subjected to column chromatography to give the title compound. 150 mg. Yield 39%.

EXAMPLE 117

Preparation of (S)-[N-3-(4-(2-(4-Oxopiperidin-1-yl)pyridin-5-yl)-3-fluorophenyl)-2-oxo-5-oxazolidinyl]methyl Acetamide In a mixture of acetone (3 ml) and water (1 ml), 3.3 g of (S)-[N-3-(4-(2-(1,4-dioxa-8-azaspiro(4,5)decan-8-yl)pyridin-5-yl)-3-fluorophenyl)-2-oxo-5-oxazolidinyl]methyl acetamide was reacted with 4 g of p-toluenesulfonic acid for 24 hours under reflux. Following the addition of ethyl acetate, the organic layer thus separated was washed with brine, dehydrated, filtered and concentrated in vacuo. Purification of the concentrate through column chromatography gave the title compound. 1.2 g. Yield 40%.

$^1$H-NMR (CDCl$_3$) δ 8.35 (s, 1H), 7.73 (m, 1H), 7.53 (dd, 1H), 7.42 (t, 1H), 7.25 (m, 1H), 6.80 (d, 1H), 6.12 (t, 1H), 4.79 (m, 1H), 4.09 (t, 1H), 3.98 (t, 4H), 3.78 (m, 1H), 3.67 (m, 2H), 2.52 (t, 4H), 2.01 (s, 3H).

EXAMPLE 118

Preparation of (S)-[N-3-(4-(2-Azidoacetylaminopyridin-5-yl)-3-fluorophenyl)-2-oxo-5-oxazolidinyl]methyl Acetamide In 6.2 ml of methylene chloride was dissolved 500 mg of (S)-[N-3-(4-(2-hydroxyacetylaminopyridin-5-yl)-3-fluorophenyl)-2-oxo-5-oxazolidinyl]methyl acetamide which was then reacted with 0.144 ml of methanesulfonyl chloride in the presence of 0.35 ml of triethyl amine at 0° C.

for 1 hour with stirring. Following the addition of methylene chloride, the organic layer thus separated was washed with brine, dehydrated, filtered and concentrated under vacuum to give 0.47 g of (S)-[N-3-(4-(2-methanesulfonyloxyacetyl aminopyridin-5-yl)-3-fluorophenyl)-2-oxo-5-oxazolidinyl] methyl acetamide. This intermediate was dissolved in 5 ml of dimethylformamide and added with 1.5 g of sodium azide at room temperature. Thereafter, reaction was conducted at 100° C. for 2 hours with stirring. Following the addition of ethyl acetate, the organic layer thus separated was washed with brine, dehydrated, filtered, and concentrated under vacuum. The concentrated was subjected to column chromatography to produce the title compound. 180 mg. Yield 34%.

$^1$H-NMR (DMSO-d$_6$) δ 10.83 (s, 1H), 8.51 (s, 1H), 8.28 (t, 1H), 8.18 (d, 1H), 8.00 (dd, 1H), 7.64 (m, 2H), 7.40 (dd, 1H), 4.76 (m, 4H), 4.21 (t, 1H), 4.13 (s, 2H), 3.78 (dd, 1H), 3.42 (t, 2H), 1.83 (s, 3H)

EXAMPLE 119

Preparation of (S)-[N-3-(4-(2-(1,2,3,4,6,7-Hexahydro-5-oxo-1,4-diazepan-1-yl)-pyridin-5-yl)-3-fluorophenyl)-2-oxo-5-oxazolidinyl]methyl Acetamide In 20 ml of formic acid, 1.2 g of (S)-[N-3-(4-(2-(4-oxopiperidin-1-yl)pyridin-5-yl)-3-fluorophenyl)-2-oxo-5-oxazolidinyl]methyl acetamide, prepared in Example 117, was reacted with 1.6 g of hydroxylamino-o-sulfonic acid at 100° C. for 8 hours with stirring. The reaction mixture was neutralized with sodium hydroxide, followed by extraction with methylene chloride. The organic layer was washed with brine, dehydrated, filtered, and concentrated in vacuo. Purification of the concentrate with column chromatography provided the title compound. 120 mg.

$^1$H-NMR (DMSO-d$_6$) δ 8.30 (s, 1H), 8.26 (t, 1H), 7.74 (m, 1H), 7.59 (m, 3H), 7.38 (dd, 1H), 6.80 (d, 1H), 4.76 (m, 1H), 4.16 (t, 1H), 3.77 (m, 6H), 3.47 (t, 2H), 3.19 (m, 2H), 1.83 (s, 3H).

EXAMPLE 120

Preparation of (S)-[N-3-(4-(2-N-(Dimethylaminomethyene)aminopyridin-5-yl)-3-fluorophenyl)-2-oxo-5-oxazolidinyl]ethyl Acetamide In methanol, 50 mg of (S)-[N-3-(4-(2-aminopyridin-5-yl)-3-fluorophenyl)-2-oxo-5-oxazolidinyl]methyl acetamide was reacted with 58 ml of N,N-dimethylaminodimethoxymethane at room temperature for 24 hours under reflux. Methylene chloride was added to the reaction mixture. The organic layer thus separated was then washed with brine, dehydrated, filtered, and concentrated under vacuum, followed by purification with column chromatography to provide the title compound. 52 mg. Yield 90%.

$^1$H-NMR (CDCl$_3$) δ 8.46 (s, 1H), 8.39 (s, 1H), 7.73 (m, 1H), 7.53 (dd, 3H), 7.47 (d, 1H), 7.27 (m, 1H), 7.70 (d, 1H), 6.04 (t, 1H), 4.80 (m, 1H), 4.08 (t, 2H), 3.81 (dd, 1H), 3.61 (m, 2H), 3.10 (s, 6H), 2.02 (s, 3H).

EXAMPLE 121

Preparation of (S)-[N-3-(4-(2-(4-Hydroxyiminopiperidin-1-yl)pyridin-5-yl)-3-fluorophenyl)-2-oxo-5-oxazolidinyl]methyl Acetamide In ethanol, 600 mg of (S)-[N-3-(4-(2-(4-oxopiperidin-1-yl)pyridin-5-yl)-3-fluorophenyl)-2-oxo-5-oxazolidinyl] methyl acetamide, prepared in Example 117, was reacted with 200 mg of hydroxylamine hydrochloride in the presence of 250 mg of pyridine for 2 hours under reflux. Following the addition of ethyl acetate, the organic layer thus separated was washed with brine, dehydrated, filtered, and concentrated under vacuum. Recrystallization of the concentrate (in chloroform/methanol/ethyl ether) provided the title compound. 600 mg. Yield 96%.

$^1$H-NMR (DMSO-d$_6$) δ 10.42 (s, 1H), 8.31 (m, 2H), 7.75 (m, 1H), 7.55 (d, 1H), 7.51 (m, 1H), 7.38 (dd, 1H), 6.95 (d, 1H), 4.79 (m, 1H), 4.14 (t, 1H), 3.75 (m, 5H), 3.41 (t, 2H), 2.49 (t, 2H), 2.36 (t, 2H), 1.82 (s, 3H).

EXAMPLE 122

Preparation of (S)-[N-3-(4-(2-(4-Methanesulfonyloxyiminopiperidinl-yl)pyridin-5-yl)-3-fluorophenyl)-2-oxo-5-oxazolidinyl]methyl Acetamide In tetrahydrofuran, 50 mg of (S)-[N-3-(4-(2-(4-hydroxyiminopiperidin-1-yl)pyridin-5-yl)-3-fluorophenyl)-2-oxo-5-oxazolidinyl]methyl acetamide, prepared in Example 121, was reacted with 14 mg of methanesulfonyl chloride in the presence of 50 mg of triethyl amine at room temperature for 30 min with stirring. Following the addition of ethyl acetate, the organic layer thus separated was washed with brine, dehydrated, filtered and concentrated in vacuo. The concentrate was subjected to column chromatography to produce the title compound. 40 mg. Yield 65%.

EXAMPLE 123

Preparation of (S)-[N-3-(4-(2-(4-Methyliminopiperidin-1-yl)pyridin-5-yl)-3-fluorophenyl)-2-oxo-5-oxazolidinyl]methyl Acetamide In ethanol, 50 mg of (S)-[N-3-(4-(2-(4-oxopiperidin-1-yl) pyridin-5-yl)-3-fluorophenyl)-2-oxo-5-oxazolidinyl]methyl acetamide, prepared in Example 117, was reacted with 16 mg of methylamine hydrochloride in the presence of 28 mg of pyridine. The imination was conducted for 3 hours under reflux. Addition of ethyl acetate to the reaction mixture separated an organic layer. This organic layer was washed with brine, followed by conducting dehydration, filtration and vacuum concentration in order. Column chromatography of the concentrate provided the title compound of purity. 10 mg. Yield 20%

EXAMPLE 124

Preparation of (S)-[N-3-(4-(2-(4-Methoxycarbonylhydrazinopiperidin-1-yl)pyridin-5-yl)-3-fluorophenyl)-2-oxo-5-oxazolidinyl]methyl Acetamide In ethanol, 100, mg of (S)-[N-3-(4-(2-(4-oxopiperidin-1-yl)pyridin-5-yl)-3-fluorophenyl)-2-oxo-5-oxazolidinyl] methyl acetamide, prepared in Example 117, was reacted with 106 mg of methoxycarbonylhydrazine for 3 hours under reflux. Addition of ethyl acetate to the reaction mixture separated an organic layer. This layer was washed with brine, followed by dehydration, filtration and vacuum concentration in order. The concentrate was subjected to column chromatography to provide the title compound. 80 mg. Yield 70%.

$^1$H-NMR (DMSO-d$_6$) δ 9.94 (s, 1H), 8.27 (m, 2H), 7.78 (d, 1H), 7.64 (m, 2H), 7.38 (dd, 1H), 7.00 (d, 1H), 4.78 (m,

1H), 4.16 (t, 1H), 3.79 (m, 5H), 3.63 (s, 3H), 3.42 (t, 4H), 2.49 (t, 2H), 1.83 (s, 3H).

EXAMPLE 125

Preparation of (S) [N-3-(4-(2-N-(L-Alanyl)aminopyridin-5-yl)-3-fluorophenyl)-2-oxo-5-oxazolidinyl]methyl Acetamide In 20 ml of pyridine was dissolved 2.19 g of N-t-butoxycarbonyl-L-alanine and the solution was added with 1 g of 2-amino-5-bromopyridine, 2.77 g of 1-(3-dimethyl (aminopropyl)-3-ethylcarbodiimide hydrochloride and 1.41 g of 4-dimethylaminopyridine individually and stirred at room temperature for 15 hours. Water was then added to the reaction mixture, followed by extraction with ethyl acetate. The organic layer thus separated was washed with brine, dehydrated, filtered, and concentrated in vacuo to give 0.713 g of 2-(N-t-butoxycarbonyl-L-alanylamino)-5-bromopyridine. This compound was dissolved, along with 0.714 g of (S)-[N-3-(4-trimethylstannyl-3-fluorophenyl)-2-oxo-5-oxazolidinyl]methyl acetamide, in 20 ml of dimethylformamide. Reaction was conducted at 100° C. for 4 hours in the presence of 0.6 ml of triethyl amine with the catalytic aid of 0.36 g of dichlorobistriphenylphosphine palladium (II) with stirring after their addition at room temperature. Water was then added to the reaction mixture, followed by the extraction with ethyl acetate. The organic layer thus separated was washed with brine, dehydrated, filtered and concentrated in vacuo. Recrystallization of the concentrate gave 0.27 g of (S)-[N-3-(4-(2-(N-t-buxotycarbonyl-L-alanylaminopyridin-5-yl)-3-fluorophenyl)-2-oxo-5-oxazolidinyl)methyl acetamide. This compound was reacted with 0.15 ml of trimethylsilyl iodide in chloroform at room temperature for 30 min under a nitrogen atmosphere. Following the addition of chloroform, the organic layer thus separated was washed with brine, dehydrated, filtered, and concentrated in vacuo. The concentrate was subjected to column chromatography to produce the title compound. 50 mg.

$^1$H-NMR (DMSO-d$_6$) δ 8.50 (s, 1H), 8.27 (t, 1H), 8.20 (d, 1H), 8.01 (m, 1H), 7.63 (m, 2H), 7.40 (dd, 1H), 4.78 (m, 1H), 4.16 (t, 1H), 3.78 (dd, 1H), 3.51 (q, 1H), 3.42 (t, 2H), 1.83 (s, 3H), 1.20 (d, 3H).

EXAMPLE 126

Preparation of (S)-[N-3-(4-(2-Acetylaminoacetylaminopyridin-5-yl)-3-fluorophenyl)-2-oxo-5-oxazolidinyl]methyl Acetamide In 10 ml of methylene chloride was dissolved 50 mg of (S)-[N-3-(4-(2-aminoacetylaminopyridin-5-yl)-3-fluorophenyl)-2-oxo-5-oxazolidinyl]methyl acetamide to which 0.018 ml of acetic anhydride and 0.035 ml of triethyl amine were dropwise added. Reaction was conducted at room temperature for 30 min with stirring. Addition of methylene chloride separated an organic layer. This layer was washed with brine, followed by dehydration, filtration, and vacuum concentration. The concentrate was purified by column chromatography to give the title compound. 15 mg. Yield 27%.

$^1$H-NMR (DMSO-d$_6$) δ 10.60 (s, 1H), 8.49 (s, 1H), 8.20 (m, 3H), 7.99 (m, 1H), 7.64 (m, 2H), 7.43 (dd, 1H), 4.78 (m, 1H), 4.16 (t, 1H), 3.95 (d, 2H), 3.79 (m, 1H), 3.42 (t, 2H), 1.88 (s, 3H), 1.83 (s, 3H).

EXAMPLE 127

Preparation of (S)-[N-3-(4-(2-Dimethylaminoacetylaminopyridin-5-yl)-3-fluorophenyl)-2-oxo-5-oxazolidinyl]methyl Acetamide In 100 ml of pyridine was dissolved 5.96 g of N,N-dimethylglycine and the solution was added with 5 g of 2-amino-5-bromopyridine 5 g, 13.85 g of 1-(3-dimethylaminopropyl)-3-ethylcarbodiimide hydrochloride and 7.06 g of 4-dimethylaminopyridine individually at room temperature. Reaction was carried out at room temperature for 15 hours with stirring. Water was then added to the reaction mixture, followed by extraction with ethyl acetate. The organic layer thus separated was washed with brine, dehydrated, filtered and concentrated in vacuo to give 1.0 g of 2-(N,N-dimethylaminoacetylamino)-5-bromopyridine. This compound was dissolved, along with 1.34 g of (S)-[N-3-(4-trimethylstannyl-3-fluorophenyl)-2-oxo-5-oxazolidinyl]methyl acetamide, in 14 ml of dimethylformamide and added with 0.68 ml of triethyl amine and 0.68 g of dichloro bistriphenylphosphine palladium (II) individually. Reaction was conducted at 100° C. for 4 hours with stirring. Water was then added to the reaction mixture, followed by extraction with ethyl acetate. The organic layer thus separated was washed with brine, dehydrate, filtered, and concentrated in vacuo. The concentrate was subjected to column chromatography to produce the title compound. 430 mg.

$^1$H-NMR (DMSO-d$_6$) δ 10.03 (s, 1H), 8.49 (s, 1H), 8.27 (m, 2H), 7.99 (m, 1H), 7.64 (m, 2H), 7.38 (dd, 1H), 4.78 (m, 1H), 4.16 (t, 1H), 3.79 (dd, 1H), 3.42 (t, 2H), 3.16 (s, 2H), 2.31 (s, 6H), 1.83 (s, 3H).

EXAMPLE 128

Preparation of (S)-[N-3-(4-(2-Nicotinoylaminopyridin-5-yl)-3-fluorophenyl)-2-oxo-5-oxazolidinyl]methyl Acetamide With the exception of using, instead of N,N-dimethylglycine, nicotinic acid as a starting material, the same procedure as in Example 127 was conducted to prepare the title compound.

$^1$H-NMR (DMSO-d$_6$) δ 11.21 (s, 1H), 9.15 (d, 1H), 8.77 (dd, 1H), 8.59 (s, 1H), 8.38 (m, 1H), 8.28 (m, 1H), 8.02 (m, 1H), 7.67 (m, 1H), 7.59 (m, 3H), 7.43 (m, 1H), 4.76 (m, 1H), 4.17 (t, 1H), 3.81 (dd, 1H), 3.42 (t, 2H), 1.83 (s, 3H).

EXAMPLE 129

Preparation of (S)-[N-3-(4-(2-(1,2,4-Triazol-1-yl)pyridin-5-yl)-3-fluorophenyl)-2-oxo-5-oxazoldinyl]methyl Acetamide In 20 ml of dimethylformamide, 1 g of 2,5-dibromopyridin was reacted with 0.58 g of 1,2,4-triazole sodium at 80° C. for 10 hours with stirring. Following the addition of ethyl acetate, the organic layer thus separated was washed with brine, dehydrated, filtered, and concentrated in vacuo to give 880 mg of 2-(1,2,4-triazol-1-yl)-5-bromopyridine. This compound was dissolved, along with 1.4 g of (S)-[N-3-(4-trimethylstannyl-3-fluorophenyl)-2-oxo-5-oxazolidinyl]methyl acetamide, in 50 ml of dimethylformamide and then added with 1.2 ml of triethyl amine and 1.1 g of dichlorobistriphenylphosphine palladium (II) at room temperature. Reaction was conducted at 100° C. for 3 hours. Water was then added to the reaction mixture, followed by extraction with ethyl acetate. The organic layer thus separated was washed with brine, dehydrated, filtered, and concentrated in vacuo. Purification of the concentrate with column chromatography provided the title compound. 320 mg. Yield 23%.

$^1$H-NMR (DMSO-d$_6$) δ 9.41 (s, 1H), 8.72 (s, 1H), 8.33 (s, 1H), 8.25 (m, 2H), 7.96 (d, 1H), 7.72 (m, 2H), 7.47 (dd, 1H), 4.76 (m, 1H), 4.18 (t, 1H), 3.43 (t, 2H), 1.83 (s, 3H).

EXAMPLE 130

Preparation of (S)-[N-3-(4-(2-(4-Hydroxypiperidin-1-yl)pyridin-5-yl)-3-fluorophenyl)-2-oxo-5-oxazolidinyl]methyl Acetamide In a mixture of ethanol and tetrahydrofuran, 300 mg of (S)-[N-3-(4-(2-(4-oxopiperidin-1-yl)pyridin-5-yl)-3- fluorophenyl)-2-oxo-5-oxazolidinyl]methylacetamide, prepared in Example 82, was reacted with 106 mg of sodium borohydride at room temperature for 1 hour with stirring. The organic layer was concentrated in vacuo, followed by the recrystallization of the concentrate in methanol, chloroform and ethyl ether to provide the title compound. 270 mg. Yield 90%.

$^1$H-NMR (DMSO-d$_6$) δ 8.27 (m, 2H), 7.70 (m, 1H), 7.52 (m, 2H), 7.34 (m, 1H), 6.90 (d, 1H), 4.76 (m, 1H), 4.69 (d, 1H), 4.17 (t, 1H), 4.07 (m, 2H), 3.79 (m, 2H), 3.42 (t, 2H), 3.12 (m, 2H), 1.83 (s, 3H), 1.75 (m, 2H), 1.41 (m, 2H).

EXAMPLE 131

Preparation of (S)-[N-3-(4-(2-N,N-(Hydroxyacetyl) methylaminopyridin-5-yl)-3-fluorophenyl)-2-oxo-5-oxazolidinyl]methyl Acetamide In a mixture of methanol and chloroform, 470 mg of (S)-[N-3-(4-(2-N,N-(acetoxyacetyl)methylaminopyridin-5-yl)-3-fluorophenyl)-2-oxo-5-oxazolidinyl]methyl acetamide was reacted with 1.5 ml of a 1 N KOH solution at room temperature for 15 min with stirring. After vacuum concentration, addition of ethylacetate separated an organic layer. This layer was dehydrated, filtered, and concentrated in vacuo. Through column chromatography, the concentrate was purified to the title compound. 64 mg.

$^1$H-NMR (DMSO-d$_6$) δ 8.61 (s, 1H), 8.26 (t, 1H), 8.06 (m, 1H), 7.62 (m, 3H), 7.47 (dd, 1H), 4.85 (t, 1H), 4.78 (m, 1H), 4.21 (d, 2H), 4.16 (t, 1H), 3.79 (t, 1H), 3.42 (t, 2H), 3.32 (s, 3H), 1.83 (s, 3H).

EXAMPLE 132

Preparation of (S)-[N-3-(4-(2-(4-Methylimidazol-1-yl)pyridin-5-yl)-3-fluorophenyl)-2-oxo-5-oxazolidinyl]methyl Acetamide Except that 2-(4-methylimidazole)-5-bromopyridine was used as a starting material, the same procedure as in Example 129 was conducted to prepare the title compound.

$^1$H-NMR (DMSO-d$_6$) δ 8.64 (s, 1H), 8.45 (s, 1H), 8.30 (t, 1H), 8.17 (m, 1H), 7.81 (d, 1H), 7.64 (m, 3H), 7.38 (dd, 1H), 4.78 (m, 1H), 4.16 (t, 1H), 3.79 (m, 1H), 3.42 (t, 2H), 2.18 (s, 3H), 1.83 (s, 3H).

EXAMPLE 133

Preparation of (S)-[N-3-(4-(2-(2-Hydroxypropionyl) aminopyridin-5-yl)-3-fluorophenyl)-2-oxo-5-oxazolidinyl]methyl Acetamide Staring with (S)-[N-3-(4-(2-(2-acetoxypropionyl) aminopyridin-5-yl)-3-fluorophenyl)-2-oxo-5-oxazolidinyl] methyl acetamide, the title compound was prepared in a manner similar to that of Example 121.

$^1$H-NMR (DMSO-d$_6$) δ 9.73 (s, 1H), 8.50 (s, 1H), 8.26 (t, 1H), 8.16 (d, 1H), 8.03 (d, 1H), 7.63 (m, 2H), 7.40 (dd, 1H), 5.90 (d, 1H), 4.75 (m, 1H), 4.20 (m, 2H), 3.79 (dd, 1H), 3.43 (t, 2H), 1.82 (s, 3H), 1.31 (d, 3H).

EXAMPLE 134

Preparation of (S)-[N-3-(4-(2-(3-Amino-1,2,4-Triazol-1-yl)pyridin-5-yl)-3-fluorophenyl)-2-oxo-5-oxazolidinyl]methyl Acetamide Staring with 2-(3-amino-1,2,4-triazinyl)-5-bromo pyridine, the title compound was prepared in a manner similar to that of Example 129.

$^1$H-NMR (DMSO-d$_6$) δ 8.64 (s, 1H), 8.24 (m, 2H), 7.83 (d, 1H), 7.61 (m, 5H), 7.43 (dd, 1H), 4.77 (m, 1H), 4.17 (t, 1H), 3.76 (dd, 1H), 3.42 (t, 2H), 1.82 (s, 3H).

EXAMPLE 135

Preparation of (S)-[N-3-(4-(2-(4-Ethoxycarbbnylimidazol-1-yl)pyridin-5-yl)-3-fluorophenyl)-2-oxo-5-oxazolidinyl]methyl Acetamide The title compound was prepared in a manner similar to that of Example 129, except that 2-(4-ethoxycarbonylimidazolyl)-5-bromopyridine was used as a starting material.

EXAMPLE 136

Preparation of (S)-[N-3-(4-(2-(Tetrazol-1-yl)-5-pyridinyl)-3-fluorophenyl)-2-oxo-5-oxazolidinyl] methyl Acetamide In 8.8 ml of dimethylformamide was dissolved 734 mg of (S)-[N-3-(4-trimethylstannyl-3-fluorophenyl)-2-oxo-5-oxazolidinyl]methyl acetamide, prepared in Preparation. Example 8, which was then reacted with 600 mg of 2-(1-tetrazolyl)-5-bromopyridine, prepared in Preparation Example 13, in the presence of 0.49 ml of triethyl amine with the catalytic aid of 372 mg of dichlorobistriphenylphosphine palladium (II) at 100° C. for 4 hours with stirring. Water was then added to the reaction mixture, followed by extraction with ethyl, acetate. The organic layer thus separated was washed with brine, dehydrated, filtered and concentrated in vacuo. The concentrate was purified through column chromatography to provide the title compound. 110 mg.

$^1$H-NMR (DMSO-d$_6$) δ 10.22 (s, 1H), 8.83 (s, 1H), 8.39 (dd, 1H), 8.30 (t, 1H), 8.15 (d, 1H), 7.76 (m, 2H), 7.47 (dd, 1H) 4.78 (m, 1H), 4.16 (t, 1H), 3.80 (dd, 1H), 3.43 (t, 2H), 1.83 (s, 3H).

EXAMPLE 137

Preparation of (S)-[N-3-(4-(2-(5-Methyl-(1,3,4)-Oxadiazol-2-yl)-pyridin-5-yl)-3-fluorophenyl)-2-oxo-5-oxazolidinyl]methyl Acetamide In 10 ml of 1-methyl-2-pyrrolidone was dissolved 1 g of (S)-[N-3-(4-trimethylstannyl-3-fluorophenyl)-2-oxo-5-oxazolidinyl]methyl acetamide, prepared in Preparation Example 8, and the solution was added at room temperature with 600 mg of 2-(1,3,4-oxadiazol)-5-bromopyridine, 320 mg of lithium chloride, and 100 mg of dichlorobistriphenyl phosphine palladium (II) individually, followed by stirring at 100° C. for 4 hours. Water was then added to the reaction mixture, then extracted with ethyl acetate. The organic layer thus separated was washed with brine, dehydrated, filtered and concentrated in vacuo. Through column chromatography, the concentrate was purified to the title compound. 300 mg.

$^1$H-NMR (DMSO-d$_6$) δ 9.99 (s, 1H), 8.73 (s, 1H), 8.26 (t, 1H), 7.95 (m, 2H), 7.64 (m, 2H), 7.47 (dd, 1H), 4.78 (m, 1H), 4.16 (t, 1H), 3.80 (dd, 1H), 3.43 (t, 2H), 1.83 (s, 3H).

EXAMPLE 138

Preparation of (S)-[N-3-(4-(2-(5-Methyl-(1,2,4)-oxadiazol-3-yl)pyridin-5-yl)-3-fluorophenyl)-2-oxo-5-oxazolidinyl]methyl Acetamide Starting with 2.8 g of 2-[5-methyl-(1,2,4)-oxadiazol-3-yl]-5-bromopyridine, the title compound was prepared in a manner similar to that of Example 137. 280 mg.

¹H-NMR (CDCl₃) δ 8.85 (s, 1H), 8.09 (d, 1H), 7.97 (m, 1H), 7.58 (dd, 1H), 7.45 (t, 1H), 7.26 (dd, 1H), 6.50 (t, 1H), 4.81 (m, 1H), 4.10 (t, 1H), 3.84 (dd, 1H), 3.68 (m, 2H), 2.67 (s, 3H), 2.01 (s, 3H).

EXAMPLE 139

Preparation of (S)-[N-3-(4-(2-(1-Methyl-5-tetrazol-yl)-pyridin-5-yl)-3-fluorophenyl)-2-oxo-5-oxazolidinyl]methyl Acetamide Starting with 110 mg of 2-(1-methyl-5-tetrazoly)-5-bromopyridine, the title compound was prepared in a manner similar to that of Example 137. 60 mg.

¹H-NMR (CDCl₃) δ 8.89 (s, 1H), 8.29 (d, 1H), 8.00 (m, 1H), 7.61 (dd, 1H), 7.46 (t, 1H), 7.26 (dd, 1H), 6.12 (t, 1H), 4.80 (m, 1H), 4.45 (s, 3H), 4.07 (t, 1H), 3.83 (dd, 1H), 3.67 (m, 2H), 2.02 (s, 3H).

EXAMPLE 140

Preparation of (S)-[N-3-(4-(2-(2-Methyl-5-tetrazolyl)-pyridin-5-yl)-3-fluorophenyl)-2-oxo-5-oxazolidinyl]methyl Acetamide Starting with 220 mg of 2-(2-methyl-5-tetrazolyl)-5-bromopyridine (220 mg), the title compound was prepared in a manner similar to that of Example 137. 180 mg.

¹H-NMR (CDCl₃) δ 8.85 (s, 1H), 8.34 (d, 1H), 8.00 (m, 1H), 7.56 (dd, 1H), 7.40 (t, 1H), 7.26 (dd, 1H), 4.76 (m, 1H), 4.49 (s, 3H), 4.07 (t, 1H), 3.79 (dd, 1H), 3.59 (m, 2H), 1.96 (s, 3H).

EXAMPLE 141

Preparation of (S)-[N-3-(4-(2-(4-Ethoxycarbonyl-(1,2,3)-triazol-1-yl)-5-pyridinyl)-3-fluorophenyl)-2-oxo-5-oxazolidinyl]methyl Acetamide Starting with 200 mg of 2-(4-ethoxycarbonyl-(1,2,3)-triazol-1-yl]-5-bromopyridine, the title compound was prepared in a manner similar to that of Example 137. 60 mg.

¹H-NMR (DMSO-d₆) δ 9.02 (s, 1H), 8.59 (s, 1H), 8.16 (dd, 1H), 8.02 (dd, 1H), 7.51 (dd, 7H), 7.35 (t, 4H), 7.29 (dd, 1H), 6.63 (t, 1H), 4.78 (m, 1H), 4.42 (tr, 2H) 4.16 (t, 3H), 3.80 (dd, 1H), 3.43 (t, 2H), 1.83 (s, 3H), 1.37 (t, 3H).

EXAMPLE 142

Preparation of (S)-[N-3-(4-(2-(3-Pyrrolinyl)-5-pyridinyl)-3-fluorophenyl)-2-oxo-5-oxazolidinyl]methyl Acetamide Starting with 200 mg of 2-(3-pyrrolinyl)-5-bromopyridine, the title compound was prepared in a manner similar to that of Example 137.

¹H-NMR (CDCl₃) δ 8.27 (brm, 2H), 7.53 (m, 2H), 7.40 (m, 1H), 6.49 (dd, 2H), 6.03 (s, 1H), 4.76 (m, 1H), 4.07 (t, 1H), 3.79 (dd, 1H), 3.59 (m, 2H), 3.40 (t, 2H), 1.96 (m, 2H), 1.92 (s, 3H).

EXAMPLE 143

Preparation of (S)-[N-3-(4-(2-(2-oxo-1,3-Oxazolidin-3-yl)-5-pyridinyl)-3-fluorophenyl)-2-oxo-5-oxazolidinyl]methyl Acetamide Starting with 150 mg of 2-(2-oxo-3-oxazolidinyl)-5-bromopyridine, the title compound was prepared in a manner similar to that of Example 137. 14 mg.

¹H-NMR (CDCl₃) δ 8.37 (s, 1H), 8.19 (d, 1H), 7.80 (m, 1H), 7.44 (m, 2H), 7.34 (t, 1H), 7.16 (dd, 1H), 4.67 (m, 1H), 4.41 (m, 1H), 4.23 (m, 2H), 3.91 (t, 2H), 3.74 (dd, 2H), 3.50 (m, 2H), 1.87 (s, 3H).

EXAMPLE 144

Preparation of (S)-[N-3-(4-(2-(2-oxazolyidinyl)-5-fluorophenyl)-2-oxo-5-oxazolidinyl]methyl Acetamide Starting with 204 mg of 2-(5-oxazolyl)-5-bromopyridine, the title compound was prepared in a manner similar to that of Example 137. 130 mg.

¹H-NMR (DMSO-d₆) δ 8.82 (s, 1H), 8.57 (s, 1H), 8.27 (m, 1H), 8.10 (m, 1H), 7.88 (s, 1H), 7.85 (s, 1H), 7.68 (m, 2H), 7.44 (dd, 1H), 4.76 (m, 1H), 4.17 (t, 1H), 3.79 (dd, 1H), 3.43 (t, 2H), 1.83 (s, 3H).

EXAMPLE 145

Preparation of (S)7[N-3-(4-(2-((1,2,4)-Oxadiazol-3-yl)-5-pyridinyl)-3-fluorophenyl)-2-oxo-5-oxazolidinyl]methyl Acetamide Except that 700 mg of 2-[(1,2,4)-oxadiazol-3-yl]-5-bromopyridine was used as a starting material, the title compound was prepared in a manner similar to that of Example 137. 300 mg.

¹H-NMR (CDCl₃) δ 8.82 (t, 1H), 7.99 (m, 1H), 7.75 (dd, 1H), 7.61 (dd, 1H), 7.30 (t, 2H), 7.28 (dd, 1H), 4.76 (m, 1H), 4.06 (t, 1H), 3.80 (dd, 1H), 3.58 (m, 2H), 1.96 (s, 3H).

EXAMPLE 146

Preparation of (S)-[N-3-(4-(2-((1,2,3)-Triazol-1-yl)-5-pyridinyl)-3-fluorophenyl)-2-oxo-5-oxazolidinyl]methyl Acetamide Except that 120 mg of 2-((1,2,4)-triazol-1-yl]-5-bromopyridine was used as a starting material, the title compound was prepared in a manner similar to that of Example 137. 90 mg.

¹H-NMR (DMSO-d₆) δ 8.90 (d, 1H), 8.78 (s, 1H), 8.29 (m, 3H), 8.02 (d, 1H), 7.70 (m, 2H), 7.46 (dd, 1H), 4.76 (m, 1H), 4.17 (t, 1H), 3.79 (dd, 2H), 3.43 (t, 2H), 1.83 (s, 3H).

EXAMPLE 147

Preparation of (S)-[N-3-(4-(2-(3-Methyl-2-oxo-(1,3,4)-triazol-1-yl)-5-pyridinyl)-3-fluorophenyl)-2-oxo-5-oxazolidinyl]methyl Acetamide Except that 290 mg of 2-[3-methyl-2-oxo-(1,3,4)-triazol-1-yl]-5-bromopyridine was used as a starting material, the title compound was prepared in a manner similar to that of Example 137. 160 mg.

¹H-NMR (DMSO-d₆) δ 8.68 (s, 1H), 8.66 (s, 1H), 8.27 (m, 3H), 7.64 (m, 2H), 7.46 (dd, 1H), 4.75 (m, 1H), 4.17 (t, 1H), 3.78 (dd, 1H), 3.44 (t, 2H), 3.41 (s, 3H), 1.83 (s, 3H).

EXAMPLE 148

Preparation of (S)-[N-3-(4-(2-(2-oxo-(1,3)-Imidazolidin-1-yl)-5-pyridinyl)-3-fluorophenyl)-2-oxo-5-oxazolidinyl]methyl Acetamide Except that 150 mg of 2-[2-oxo-3-t-butyloxy carbonyl-(1,3)-imidazolidin-1-yl]-5-bromopyridine was used as a starting material, the same procedure as in Example 137 was carried out to prepare the-title compound. 25 mg.

¹H-NMR (CDCl₃) δ 8.29 (s, 1H), 8.21 (dd, 1H), 7.66 (m, 1H), 7.52–7.39 (m, 2H), 7.27 (d, 1H), 7.12 (dd, 1H), 4.67 (m, 1H), 4.07–3.88 (m, 2H), 3.70 (dd, 1H), 3.50–3.27 (mt, 4H), 1.87 (s, 3H).

EXAMPLE 149

Preparation of (S)-[N-3-(4-(2-(4-Hydroxy-piperidin-1-yl)-5-piridinyl)-3-fluorophenyl)-2-oxo-5-oxazolidinyl]methyl Acetamide Starting with 1.9 g of 2-(4-hydroxypiperidin-1-yl)-5-bromopyridine, the title compound was prepared in a manner similar to that of Example 137. 400 mg.

¹H-NMR (DMSO-d₆) δ 8.27 (s, 1H), 8.24–8.22 (t, 1H), 7.67 (dd, 2H), 7.52 (dd, 1H), 7.47 (dd, 1H), 6.91 (d, 4H), 4.75 (m, 2H), 4.69 (d, 1H), 4.16 (d, 1H), 1.07 (m, 2H), 3.72 (m, 2H), 3.43 (t, 2H), 3.12 (m, 2H), 1.83 (s, 3H), 1.75 (m, 2H), 1.34 (m, 2H).

EXAMPLE 150

Preparation of (S)-[N-3-(4-((2-oxo-(2,3)-Dihydro-(1,3,4)-triazol-3-yl)-5-pyridinyl)-3-fluorophenyl)-2-oxo-5-oxazolidinyl]methyl Acetamide Except that 500 mg of 2-[3-t-butoxycarbonyl-2-oxo-(2,3)-dihydro-1,3,4-triazol-1-yl]-5-bromopyridine, the title compound was prepared in a manner similar to that of Example 137. 100 mg.

¹H-NMR (DMSO-d₆) δ 8.60 (dd, 1H), 8.21 (m, 2H), 7.68 (d, 1H), 7.62–7.44 (dd, H), 4.76 (m, 1H), (t, 1H), 3.79 (dd, 1H), 3.59 (m, 2H), 3.15 (m, 2H), 1.96 (s, 3H).

EXAMPLE 151

Preparation of (S)-[N-3-(4-(2-(5-Hydroxymethyl-(1,2,4)-oxadiazol-3-yl)-5-pyridinyl)-3-fluorophenyl)-2-oxo-5-oxazolidinyl]methyl Acetamide (Step 1) Preparation of (S)-[N-3-(4-(2-Cyano-5-pyridinyl)-3-fluorophenyl)-2-oxo-5-oxazolidinyl]methyl Acetamide In 85 ml of 1-methyl-2-pyrrolidone was dissolved 10.7 g of (S)-[N-3-(4-trimethylstannyl-3-fluorophenyl)-2-oxo-5-oxazolidinyl]methyl acetamide, prepared in Preparation Example 8, and the solution was added at room temperature with 4.7 g of 2-cyano-5-bromopyridine, 3.27 g of lithium chloride, and 0.9 g of dichlorobistriphenylphosphine palladium (II) individually. Reaction was conducted at 120° C. for 4 hours with stirring. After completion of the reaction, the same post-treatment as in above examples was effected to give the title compound. 4.67 mg.

¹H-NMR (DMSO-d₆) δ 8.95 (s, 1H), 8.26–8.22 (dd, 2H), 8.15 (d, 1H), 7.76 (m, 2H), 7.47 (dd, 1H), 4.78 (m, 1H), 4.16 (t, 1H), 3.80 (dd, 1H), 3.43 (t, 2H), 1.83 (s, 3H).

(Step 2): Preparation of (S)-[N-3-(4-(2-Imino-N-hydroxyaminomethyl-5-pyridinyl)-3-fluorophenyl)-2-oxo-5-oxazolidinyl]methyl Acetamide In 100 ml of ethanol, 7 g of (S)-[N-3-(2-cyano-5-pyridinyl)-3-fluorophenyl]-2-oxo-5-oxazolidinyl]methyl acetamide was reacted at room temperature for 2 hours with 3.4 g of hydroxy amine in the presence of 5.0 g of sodium hydrogen carbonate under reflux. After completion of the imination, an ordinary post-treatment was conducted to give the title compound. 6 g.

¹H-NMR (DMSO-d₆) δ 9.99 (s, 1H), 8.73 (s, 1H), 8.26 (t, 1H), 7.95 (m, 2H), 7.64 (m, 2H), 7.47 (dd, 1H), 4.78 (m, 1H), 4.16 (t, 1H), 3.80 (dd, 1H), 3.43 (t, 2H), 1.83 (s, 3H).

(Step 3): Preparation of (S)-[N-3-(4-(2-(5-Hydroxymethyl-(1,2,4)-oxadiazol-3-yl)-5-pyridinyl)-3-fluorophenyl)-2-oxo-5-oxazolidinyl]methyl Acetamide In 20 ml of acetone, 2 g of (S)-[N-3-(4-(2-imino-N-hydroxyaminomethyl-5-pyridinyl)-3-fluorophenyl)-2-oxo-5-oxazolidinyl]methyl acetamide was reacted for 6 hours with 0.7 ml of acetoxyacetyl chloride in the presence of 1.1 g of potassium carbonate under reflux. After completion of the reaction, a typical post-treatment was conducted. The resulting residue was dissolved in 20 ml of pyridine and refluxed for 7 hours. Afterwards, the reaction mixture was concentrated in vacuo and added with a citric acid solution, followed by extraction with ethyl acetate. The organic layer thus separated was washed with brine, dehydrated, filtered, and concentrated in vacuo. The concentrate was dissolved in methanol and reacted with 588 mg of potassium carbonate at room temperature for 2 hours. After the reaction was completed, the reaction mixture was added with water and extracted with chloroform. Subsequently, the organic layer was dehydrated, filtered, and concentrated in vacuo. The concentrate was subjected to column chromatography to give the title compound. 600 mg.

¹H NMR (CDCl₃) δ 8.85 (s, 1H), 8.06 (d, 1H), 8.00 (dd, 1H), 7.86 (t, 1H), 7.45 (dd, 1H), 7.40 (t, 1H), 7.22 (dd, 1H), 4.80 (s, 1H) 4.76 (m, 1H), 4.07 (t, 1H), 3.79 (dd, 1H), 3.59 (m, 2H), 1.96 (s, 3H).

EXAMPLE 152

Preparation of (S)-[N-3-(4-(2-(5-Tetrazolyl)-5-pyridinyl)-3-fluorophenyl)-2-oxo-5-oxazolidinyl] methyl Acetamide In 15 ml of dimethylformamide was dissolved 1 g of (S)-[N-3-(4-(2-cyano-5-pyridinyl)-3-fluorophenyl)-2-oxo-5-oxazolidinyl]methyl acetamide, prepared in Example 151 and the solution was added at room temperature with 1.10 g of sodium azide and 0.91 g of ammonium chloride, followed by stirring at 120° C. for 2 hours. After begin cooled to room temperature, the reaction mixture was added with 4 ml of ice water and 4 ml of ethyl acetate, along with 2 g of sodium nitrate, and controlled to pH 2 with a 6 N HCl solution. Following stirring at room temperature 1 hour, the reaction mixture was extracted with ethyl acetate. The organic layer thus separated was dehydrated, filtered, and concentrated to give a solid which was then recrystallized in ethyl ether to provide the title compound. 0.8 g.

¹H-NMR (DMSO-d₆) δ 8.97 (s, 1H), 8.29 (m, 3H), 7.72 (t, 1H), 7.65 (dd, 1H), 7.47 (dd, 1H), 4.78 (m, 1H), 4.18 (t, 1H), 3.81 (dd, 1H), 3.44 (dd, 2H), 1.83 (s, 3H).

EXAMPLE 153

Preparation of (S)-[N-3-(4-(2-(5-Methoxymethyl-(1,2,4)-oxadiazol-3-yl)-5-pyridinyl)-3-fluorophenyl)-2-oxo-5-oxazolidinyl]methyl Acetamide In 5 ml of pyridine was dissolved 300 mg of the intermediate (S)-[N-3-(4-(2-imino-N-hydroxyaminomethyl-5-pyridinyl)-3-fluorophenyl)-2-oxo-5-oxazolidinyl]methyl acetamide (300 mg), prepared in Example 151, which was then reacted with 450 ml of methoxyacetyl chloride for 1 hour under reflux. After completion of the reaction, the reaction mixture was concentrate under vacuum. Water was then added to the concentrate, followed by extraction with ethyl acetate. The organic layer thus separated was washed with brine, dehydrated, filtered, and concentrated under vacuum. Purification of the concentrate through column chromatography provided the title compound. 200 mg.

$^1$H-NMR (CDCl$_3$) δ 8.86 (s, 1H), 8.22 (d, 1H), 8.00 (dd, 1H), 7.64 (m, 1H), 7.46 (t, 1H), 7.25 (dd, 1H), 6.16 (t, 1H), 4.81 (s, 1H), 4.75 (m, 1H), 4.17 (t, 1H), 3.78 (dd, 1H), 3.44 (t, 2H), 3.55 (s, 3H), 2.01 (s, 3H).

EXAMPLE 154

Preparation of (S)-[N-3-(4-(2-(5-Trichloromethyl-(1, 2,4)-oxadiazol-3-yl)-5-pyridinyl)-3-fluorophenyl)-2-oxo-5-oxazolidinyl]methyl Acetamide In 20 ml of trichloroacetic acid was dissolved 600 mg of the intermediate (S)-[N-3-(4-(2-imino-N-hydroxyaminomethyl-5-pyridinyl)-3-fluorophenyl)-2-oxo-5-oxazolidinyl]methyl acetamide and the solution was added with 34 ml of trichloroacetyl chloride at 85° C. Reaction was conducted at 95° C. for 3 hours. Water was then added to the reaction mixture, followed by extraction with ethyl acetate. The organic layers thus separated was washed with brine, dehydrated, filtered, and concentrated in vacuo. Purification of the concentrate through column chromatography provided the title compound. 600 mg.

$^1$H-NMR (CDCl$_3$) δ 7.99 (m, 1H), 7.75 (dd, 1H), 7.61 (dd, 1H), 7.30 (t, 2H), 7.28 (dd, 1H), 4.76 (m, 1H), 4.06 (t, 1H), 3.80 (dd, 1H), 3.58 (m, 2H), 1.96 (s, 3H).

EXAMPLE 155

Preparation of (S)-[N-3-(4-(2-(5-Dimethylamino-(1, 2,4)-oxadiazol-3-yl)-5-pyridinyl)-3-fluorophenyl)-2-oxo-5-oxazolidinyl]methyl Acetamide In 5 ml of dimethylformamide was dissolved 80 mg of (S)-[N-3-(4-(2-(5-trichloromethyl-(1,2,4)-oxadiazol-3-yl)-5-pyridinyl)-3-fluorophenyl)-2-oxo-5-oxazolidinyl]methyl acetamide, prepared in Example 154, which was then reacted at room temperature for 4 hours with 2 ml of dimethylamine. Water was then added to the reaction mixture, followed by extraction with ethyl acetate. The organic layer thus separated was washed with brine, dehydrated, filtered, and concentrated under vacuum. The concentrate was subjected to column chromatography to provide the title compound. 40 mg.

$^1$H-NMR (CDCl$_3$) δ 8.85 (s, 1H), 8.34 (d, 1H), 8.00 (m, 1H), 7.56 (dd, 1H), 7.40 (t, 1H), 7.26 (dd, 1H), 4.76 (m, 1H), 4.07 (t, 1H), 3.79 (dd, 1H), 3.59 (m, 2H), 3.15 (s, 6H), 1.96 (s, 3H).

EXAMPLE 156

Preparation of (S)-[N-3-(4-(2-(5-Amino-(1,2,4)-oxadiazol-3-yl)-5-pyridinyl)-3-fluorophenyl)-2-oxo-5-oxazolidinyl]methyl Acetamide In 5 ml of methanol was dissolved 500 mg of (S)-[N-3-(4-(2-(5-trichloromethyl-(1,2,4)-oxadiazol-3-yl)-5-pyridinyl)-3-fluorophenyl)-2-oxo-5-oxazolidinyl]methyl acetamide, prepared in Example 154, which was then reacted at room temperature for 24 hours with 273 mg of cyanogens bromide under reflux. The reaction was stopped by the addition of water, followed by extraction with ethyl acetate. The organic layer thus separated was washed with brine, dehydrated, filtered, and concentrated in vacuo. The concentrate was subjected to column chromatography to provide the title compound. 13 mg.

$^1$H-NMR (CDCl$_3$) δ 8.87 (brm, 1H), 7.92 (m, 2H), 7.41 (m, 2H), 4.76 (m, 1H), 4.07 (t, 1H), 3.79 (dd, 1H), 3.59 (m, 2H), 3.40 (m, 2H), 1.96 (m, 2H).

EXAMPLE 157

Preparation of (S)-[N-3-(4-(2-(4-Acetylamino-piperidin-1-yl)-5-pyridinyl)-3-fluorophenyl)-2-oxo-5-oxazolidinyl]methyl Acetamide In 5 ml of methylene chloride was dissolved 400 mg of (S)-[N-3-(4-(2-(4-hydroxy-piperidin-1-yl)-5-pyridinyl)-3-fluorophenyl)-2-oxo-5-oxazolidinyl]methyl acetamide, prepared in Example 149, and the solution was added with at 0° C. with 530 ml of triethylamine, 150 ml of methansulfonyl chloride. Reaction was conducted at room temperature. Subsequently, water was added to the reaction mixture to stop the reaction, followed by extraction with ethyl acetate. The organic layer thus separated was washed with brine, dehydrated, filtered, concentrated in vacuo, and dried. In 5 ml of dimethylformamide, 450 mg of the residue was reacted with 200 mg of sodium azide at 90° C. for 3 hours. After water was added to stop the reaction, the reaction mixture was extracted with ethyl acetate. The organic thus separated was washed with brine, dehydrated, filtered, concentrated under vacuum, and dried. Without additional purification, 300 mg of the residue was dissolved in 4 ml of tetrahydrofuran and reacted with 200 mg of triphenylphosphine in the presence of a small quantity of water for 3 hours under reflux. Water was then added, followed by extraction with ethyl acetate. The organic layer thus separated was dehydrated, filtered, concentrated under vacuum, and dried to give 250 mg of (S)-[N-3-(4-(2-(4-amino-piperidine-1-yl)-5-pyridinyl)-3-fluorophenyl)-2-oxo-5-oxazolidinyl]methyl acetamide. To 100 mg of this compound, 5 ml of methylene chloride was added, followed by the addition of 48 ml of triethylamine and 36 ml of acetic anhydride at 0° C. Reaction was conducted at room temperature for 1 hour. After water was added to stop the reaction, the reaction mixture was extracted with ethyl acetate. The organic layer thus separated was washed with brine, dehydrated, filtered, and concentrated under vacuum. Through column chromatography, the concentrate was purified to the title compound. 80 mg.

$^1$H-NMR (CDCl$_3$) δ 7.69 (dd, 1H), 7.52 (dd, 2H), 7.40 (dd, 1H), 6.98 (dd, 1H), 4.76 (m, 1H), 4.07 (t, 1H), 3.79 (dd, 1H), 3.59 (m, 2H), 3.15 (m, 2H), 2.88 (t, 2H) 1.99 (m, 2H), 1.94 (s, 3H), 1.96 (s, 3H), 1.52 (m, 2H).

EXAMPLE 158

Preparation of (S)-[N-3-(4-(2-(4-Acetyloxymethylcarbonylamino-1-piperidinyl)-5-pyridinyl)-3-fluorophenyl)-2-oxo-5-oxazolidinyl] methyl Acetamide In 5 ml of tetrahydrofuran was dissolved 300 mg of the intermediate (S)-[N-3-(4-(2-(4-amino-piperidin-1-yl)-5-pyridinyl)-3-fluorophenyl)-2-oxo-5-oxazolidinyl]methyl acetamide, prepared in Example 157, and the solution was added with 0° C. with 300 ml of triethyl amine and 115 ml of acetoxyacetyl chloride. Reaction was conducted at room temperature for 1 hour. Water was then added to stop the reaction, followed by extraction with ethyl acetate. The organic layer thus separated was washed with brine, dehydrated, filtered, and concentrated in vacuo. The concentrate was purified through column chromatography to provide the title compound. 150 mg.

$^1$H-NMR (DMSO-d$_6$) δ 7.69 (dd, 1H), 7.52 (dd, 2H), 7.40 (dd, 1H), 6.98 (dd, 1H), 4.76 (m, 1H), 4.73 (s, 2H), 4.07 (t, 1H), 3.79 (dd, 1H), 3.59 (m, 2H), 3.15 (m, 2H), 2.88 (t, 2H), 2:16 (s, 3H), 1.99 (m, 2H), 1.96 (s, 3H), 1.52 (m, 2H).

EXAMPLE 159

Preparation of (S)-[N-3-(4-(2-(4-Hydroxymethylcarbonylamino-piperidin-1-yl)-5-pyridinyl)-3-fluorophenyl)-2-oxo-5-oxazolidinyl] methyl Acetamide In 2 ml of methanol was dissolved 150 mg of (S)-[N-3-(4-(2-(4-acetyloxymethylcarbonylamino-1-piperidinyl)-5- pyridinyl)-3-fluorophenyl)-2-oxo-5-oxazolidinyl]methyl acetamide, prepared in Example 158, which was reacted with 200 mg of potassium carbonate at room temperature for 2 hours. After completion of the reaction, an ordinary post-treatment was conducted to provide the title compound. 100 mg.

$^1$H-NMR (DMSO-d$_6$) δ 7.69 (dd, 1H), 7.49 (dd, 2H), 7.40 (dd, 1H), 6.97 (dd, 1H), 4.76 (m, 1H), 4.75 (s, 2H), 4.08 (t, 1H), 3.74 (dd, 1H), 3.59 (m, 2H), 3.15 (m, 2H), 2.88 (t, 2H), 1.99 (m, 2H), 1.96 (s, 3H), 1.52 (m, 2H).

EXAMPLE 160

Preparation of (S)-[N-3-(4-(2-((3,4)-Dihydroxy-pyrrolidin-1-yl)-5-pyridinyl)-3-fluorophenyl)-2-oxo-5-oxazolidinyl]methyl Acetamide In 2 ml of a mixture of water/acetone/acetonitrile (1:1:1) was dissolved 100 mg of (S)-[N-3-(4-(2-(3-pyrrolinyl)-5-pyridinyl)-3-fluoronyl)-2-oxo-5-oxazolidinyl]methyl acetamide, which was reacted with 10 mg of osmiumtetraoxide at room temperature for 10 hours. After completion of the reaction, an ordinary post-treatment was conducted to provide the title compound. 30 mg.

$^1$H-NMR (DMSO-d$_6$) δ 8.23 (m, 2H), 7.65 (dd, 1H), 7.47 (mdd, 1H), 7.40 (dd, 1H), 4.90 (m, 1H), 4.73 (t, 1H) 4.13 (t, 1H), 3.79 (dd, 1H), 3.59 (m, 2H), 3.20 (m, 2H), 3.15 (m, 2H), 1.96 (s, 3H).

EXPERIMENTAL EXAMPLE

Assay for In Vitro Antibacterial Activity

Using an agar dilution method, compounds of the present invention were assayed for inhibitory activity against various microorganisms, including methicilin resistant *Staphylococcus aureus* (MRSA), vancomycin resistant Enterococci (VRE), *H. Influenzae*, Ethanmbutol resistant *Mycobacterium tuberculosis* (ATCC 35837), and vancomycin resistant *Mycobacterium tuberculosis* (ATCC 35837). For comparison, U-100766 (Zyvox) of formula 3, which gained the approval of the FDA (Food and Drug Administration) of U.S.A., Cycloserine, and Rifampin were also tested (*Chemotheraphy*, 29 (1), 76, (1981)). In this regard, the level of antibacterial activity was expressed as minimal inhibitory concentration (MIC, μ/ml), and the results are given in Table 1, below.

TABLE 1

| | Antibacterial Activity (MIC50, μg/ml) | | | | |
|---|---|---|---|---|---|
| Cpd. | MRSA[1] | VRE[2] | Influenzae[3] | ATCC 35837[4] | ATCC 27294[5] |
| U-100766 | 3.13 | 1.56 | 25 | 1.56 | 1.56 |
| Cycloserine | — | — | — | 6.25 | 6.25 |
| Rifampin | — | — | — | 0.2 | 0.2 |
| Exmp. 129 | 0.39 | 0.2 | 6.25 | 0.2 | 0.1 |
| Exmp. 136 | 0.78 | 0.2 | 12.5 | 0.1 | 0.1 |
| Exmp. 137 | 0.39 | 0.2 | 3.13 | 0.1 | 0.1 |
| Exmp. 138 | 0.78 | 0.39 | 3.13 | 0.1 | 0.1 |
| Exmp. 139 | 0.78 | 0.2 | 3.13 | 0.1 | 0.1 |
| Exmp. 140 | 0.78 | 0.2 | 12.5 | 0.1 | 0.1 |

TABLE 1-continued

| | Antibacterial Activity (MIC50, μg/ml) | | | | |
|---|---|---|---|---|---|
| Cpd. | MRSA[1] | VRE[2] | Influenzae[3] | ATCC 35837[4] | ATCC 27294[5] |
| Exmp. 143 | 0.78 | 0.2 | 1.56 | 0.1 | 0.1 |
| Exmp. 152 | >25 | >25 | >25 | >25 | >25 |

[1]MRSA: methicillin resistant *Staphylococcus aureus*
[2]VRE: vancomycin resistant Enterococci
[3]H. Influenzae
[4]ATCC 35837: Ethanmbutol resistant *Mycobacterium tuberculosis*
[5]ATCC 27294: Vancomycine *Mycobacterium tuberculosis*

As apparent from the data of Table 1, the compounds of the present invention have more potent inhibitory activity against Staphylococcus and Enterococci, both resistant to conventional antibiotics, compared to U-100766 (Zyvox), which gained the approval of the FDA of U.S.A. In particular, compounds having the tetrazole-substituted pyridine ring show various potentials of antibacterial activity, depending on the substitution position of the tetrazole moiety and the substituents attached to the tetrazole moiety (Compounds of Example Nos. 136, 137, 140 and 152. Additionally, most of the compounds of the present invention are found to be superior in inhibitory activity against the tuberculosis germs compared to Cycloserine and Rifampin.

INDUSTRIAL APPLICABILITY

As described hereinbefore, the oxazolidinone compounds of formula 1 have potent antibacterial activity against a broad spectrum of bacteria and their antibacterial activity is maintained high in vivo. Exerting potent antibacterial activity versus various human and animal pathogens, including Gram-positive bacteria such as Staphylococi, Enterococci and Streptococi, anaerobic microorganisms such as Bacteroides and Clostridia, and acid-resistant microorganisms such as Mycobacterium, the compounds of the present invention are therefore useful as antibiotics.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. Derivatives of oxazolidinone of formula 1, and pharmaceutically acceptable salt thereof:

formula 1

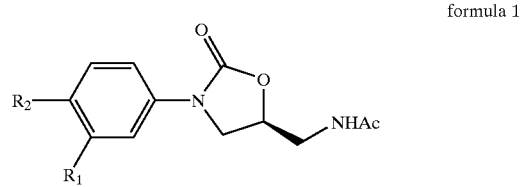

wherein, $R_1$ is H, F, Cl or $CF_3$;

$R_2$ is

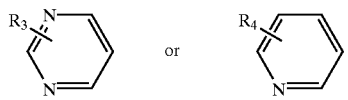 or where $R_3$ is 1) amino or piperazinyl optionally substituted with $R_5$, where $R_5$ is:
   (a) H;
   (b) triphenylmethyl;
   (c) substituted or unsubstituted acetyl, provided that the substituted acetyl is selected from the group consisting of benzyloxyacetyl, acetoxyacetyl, hydroxy acetyl, $C_1$–$C_3$ alkylaminoacetoxyacetyl, acetyl substituted with halogen, morpholi-4-nylacetyl, imidazol-1-ylcarbonyloxy acetyl, $C_1$–$C_3$ alkoxycarbonylmethylaminoacetyl, $C_1$–$C_3$ alkoxyacetyl, t-butyl acetyl, phenyl acetyl optionally substituted with $C_1$–$C_3$ alkoxy, and $C_1$–$C_3$ alkoxyoxoacetyl;
   (d) substituted or unsubstituted benzoyl, provided that the substituted benzoyl is selected from the group consisting of $C_1$–$C_4$ alkoxybenzoyl, trihalomethylbenzoyl and nitrobenzoyl;
   (e) substituted or unsubstituted carbonyl, provided that the substituted carbonyl is selected from the group consisting of $C_1$–$C_4$ haloalkylcarbonyl, phenoxycarbonyl and benzyloxycarbonyl;
   (f) $C_1$–$C_3$ alkoxyphenyl;
   (g) acryloyl optionally substituted with $C_1$–$C_3$ alkyl;
   (h) nicotinoyl;
   (i) pivaloyl;
   (j) crotonyl, or
   (k) n-valeryl, $R_4$ is: azido; —(C=O)$_l$—$R_6$; —$NR_7R_8$; —(CH$_2$)$_m$—$R_9$; or —$OR_{10}$,
   where $R_6$ is: $C_1$–$C_3$ alkoxy; amino; $C_1$–$C_3$ alkylamino; or $C_1$–$C_3$ hydroxyalkylamino,
   l is an integer of 1 to 2,
   $R_7$ and $R_8$, which may be the same or different, represent,
      (a) $C_1$–$C_4$ alkyl substituted with one or more phenyl groups, or $C_1$–$C_4$ alkenyl substituted with $C_1$–$C_3$ alkylamino;
      (b) substituted or unsubstituted acetyl, provided that the substituted acetyl is selected from the group consisting of acetoxyacetyl, hydroxyacetyl, $C_1$–$C_3$ alkylaminoacetoxyacetyl, $C_1$–$C_3$ alkoxyacetyl, aminoacetyl, azidoacetyl, acetylaminoacetyl, $C_1$–$C_3$ alkylaminoacetyl, aminopropionyl, and hydroxylpropionyl; or
      (c) nicotinoyl,
   $R_9$ is: azido; hydroxy; $C_1$–$C_3$ alkylaminoacetoxy; acetylthio, mercapto, cyano, a halogen atom, or a 5- or 6-membered heterocycle,
   m is an integer of 1 to 4,
   $R_{10}$ is: acetyl; alkoxyalkyl; methanesulfonyl;

2) Heterocylic rings selected from the group consisting of:
   a) 5- or 6-membered heteroring containing one or more N or O as ring members, preferably represented by the following formula:

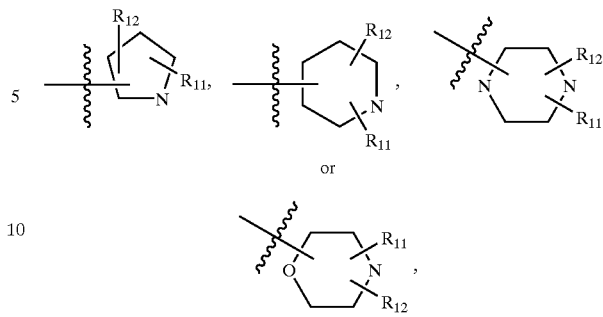

or b) a 5-membered heterocyclic ring containing at least one nitrogen or oxygen atom or both of them, as ring members, in which any one carbon atom is saturated with two hydrogen atoms or forms a double bond with oxygen (ketone), nitrogen (imino) or sulfur (thioketone), preferably of the following formula:

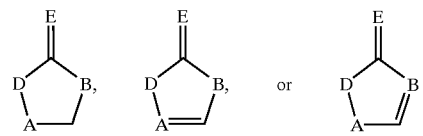

wherein A, B, and D, which may be the same or different, each represents a carbon, an oxygen or a nitrogen atom, and E represents two hydrogen atoms, an oxygen, a sulfur, or a nitrogen atom, and more preferably of the following formula:

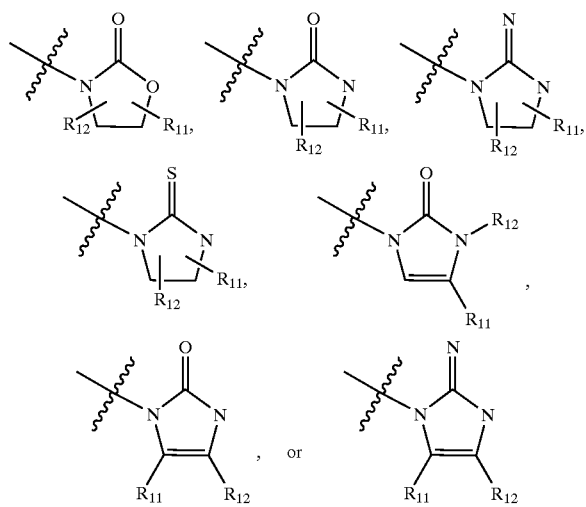

c) 5- or 6-membered hetero aromatic ring containing C, N, O or S as ring members and preferably one or two N or O, or at least one nitrogen and at least one oxygen atom together, as ring members of the following formula:

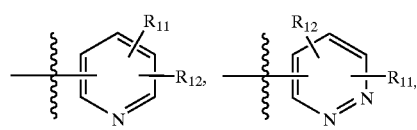

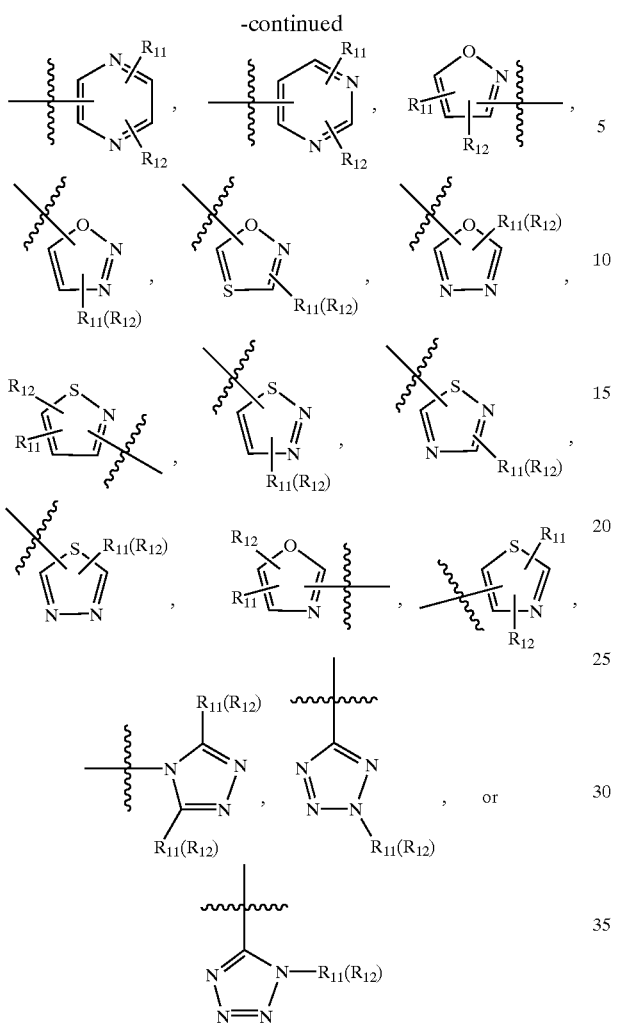

where $R_{11}$ and $R_{12}$, which are the same or different, each represents:
(i) H, F, Cl, Br or I;
(ii) $C_1$–$C_4$ alkyl substituted optionally with at least one substituent, provided that the substituted alkyl is selected from the group consisting of hydroxyalkyl, alkoxycarbonylalkyl, trihaloalkyl, acetoxyalkyl, alkylaminoalkyl, alkoxyalkyl, and methanesulfonyloxyalkyl;
(iii) substituted or unsubstituted acetyl, provided that the substituted acetyl is selected from the group consisting of acetoxyacetyl, hydroxyacetyl, $C_1$–$C_3$ alkylamino acetoxyacetyl, $C_1$–$C_3$ alkoxyacetyl, aminoacetyl, azidoacetyl, acetylaminoacetyl, $C_1$–$C_3$ alkylaminoacetyl, aminopropionyl, and hydroxypropionyl;
(iv) azido, hydroxy, mercapto, cyano, ketone, or amino;
(v) substituted or unsubstituted imino, provided that the substituted imino is selected from the group consisting of hydroxyimino, alkylimino, alkoxyimino or methanesulfonyloxyimino;
(vi) hydrozino optionally substituted with alkoxycarbonyl;
(vii) —$OR_{13}$, where $R_{13}$ is H, $C_1$–$C_3$ alkyl, acetyl, alkoxyalkyl, hydroxyacetyl or methanesulfonyl;
(viii) —$NR_{14}R_{15}$, wherein $R_{14}$ and $R_{15}$ represent independently H, $C_1$–$C_3$ alkyl, acetyl, alkoxylalkyl, hydroxyacetyl or methansulfonyl;
(ix) —(C=O)—$(R_{16})_n$—,
where $R_{16}$ is:
1) $C_1$–$C_6$ alkyl, or alkenyl optionally substituted with $C_1$–$C_3$ alkyl;
2) alkoxycarbonyl;
3) acetoxymethyl, benzyloxymethyl, hydroxymethyl, $C_1$–$C_3$ alkylacetoxymethyl, halomethyl, $C_1$–$C_3$ alkoxymethyl, morpholinylmethyl, $C_1$–$C_3$ alkoxycarbonylmethyl aminomethyl, $C_1$–$C_3$ methanesulfonyloxymethyl, alkoxyoxomethyl, $C_1$–$C_3$ nicotinoyloxymethyl, alkoxyphenylmethyl, benzyl, or trihalomethyl;
4) $C_1$–$C_3$ alkoxy, phenyloxy, allyloxy, $C_1$–$C_3$ haloalkyloxy, benzyloxy optionally substituted with nitoro, or 9-fluorenylmethyloxy;
5) nicotinoylmethyl; or
6) a 5- or 6-membered heterocyclic ring.

2. The oxazoline derivatives according to claim 1, wherein the derivatives are selected from the group consisted of;

3) (S)-[N-3-(4-(2-piperazin-1-ylpyrimidin-5-yl)-3-fluorophenyl)-2-oxo-5-oxazolidinyl]methyl acetamide,
4) (S)-[N-3-(4-(2-(4-acetylpiperazin-1-yl)pyrimidin-5-yl)-3-fluorophenyl]-2-oxo-5-oxazolidinyl]methyl acetamide,
5) (S)-[N-3-(4-(2-(4-benzyloxyacetylpiperazin-1-yl)pyrimidin-5-yl)-3-fluorophenyl]-2-oxo-5-oxazolidinyl]methyl acetamide,
6) (S)-[N-3-(4-(2-(4-acetoxyacetylpiperazin-1-yl)pyrimidin-5-yl)-3-fluorophenyl)-2-oxo-5-oxazolidinyl]methyl acetamide,
7) (S)-[N-3-(4-(2-(4-hydroxyacetylpiperazin-1-yl)pyrimidin-5-yl)-3-fluorophenyl)-2-oxo-5-oxazolidinyl]methyl acetamide,
8) (S)-[N-3-(4-(2-(4-dimethylaminoacetoxyacetylpiperazin-1-yl)pyrimidin-5-yl)-3-fluorophenyl)-2-oxo-5-oxazolidinyl]methyl acetamide,
9) (S)-[N-3-(4-(2-(4-bromoacetylpiperazin-1-yl)pyrimidin-5-yl)-3-fluorophenyl)-2-oxo-5-oxazolidinyl]methyl acetamide,
10) (S)-[N-3-(4-(2-(4-morpholin-4-ylacetylpiperazin-1-yl)pyrimidin-5-yl)-3-fluorophenyl)-2-oxo-5-oxazolidinyl]methyl acetamide,
11) (S)-[N-3-(4-(2-(4-imidazol-1-ylcarbonyloxyacetyl piperazin-1-yl)pyrimidin-5-yl)-3-fluorophenyl)-2-oxo-5-oxazolidinyl]methyl acetamide,
12) (S)-[N-3-(4-(2-(4-chloroacetylpiperazin-1-yl)pyrimidin-5-yl)-3-fluorophenyl)-2-oxo-5-oxazolidinyl]methyl acetamide,
13) (S)-[N-3-(4-(2-(4-methoxycarbonylmethylaminoacetyl piperazin-1-yl)pyrimidin-5-yl)-3-fluorophenyl)-2-oxo-5-oxazolidinyl]methyl acetamide,
14) (S)-[N-3-(4-(2-(4-(4-methoxyphenylpiperazin-4-yl)acetylpiperazin-1-yl)pyrimidin-5-yl)-3-fluorophenyl)-2-oxo-5-oxazolidinyl]methyl acetamide,
15) (S)-[N-3-(4-(2-(4-methoxyacetylpiperazin-1-yl)pyrimidin-5-yl)-3-fluorophenyl)-2-oxo-5-oxazolidinyl]methyl acetamide,
16) (S)-[N-3-(4-(2-(4-acryloylpiperazin-1-yl)pyrimidin-5-yl)-3-fluorophenyl)-2-oxo-5-oxazolidinyl]methyl acetamide, 17) (S)-[N-3-(4-(2-(4-ethoxyoxoacetylpiperazin-1-yl) pyrimidin-5-yl)-3-fluorophenyl)-2-oxo-5-oxazolidinyl]methyl acetamide,
18) (S)-[N-3-(4-(2-(4-nicotinoylpiperazin-1-yl) pyrimidin-5-yl)-3-fluorophenyl)-2-oxo-5-oxazolidinyl]methyl acetamide,
19) (S)-[N-3-(4-(2-(4-pivaloylpiperazin-1-yl)pyrimidin-5-yl)-3-fluorophenyl)-2-oxo-5-oxazolidinyl]methyl acetamide,
20) (S)-[N-3-(4-(2-(4-t-butylacetylpiperazin-1-yl) pyrimidin-5-yl)-3-fluorophenyl)-2-oxo-5-oxazolidinyl]methyl acetamide,
21) (S)-[N-3-(4-(2-(4-(2,5-dimethoxyphenyl) acetylpiperazin-1-yl)pyrimidin-5-yl)-3-fluorophenyl)-2-oxo-5-oxazolidinyl]methyl acetamide,
22) (S)-[N-3-(4-(2-(4-(3,3-dimethylacryloyl)piperazin-1-yl)pyrimidin-5-yl)-3-fluorophenyl)-2-oxo-5-oxazolidinyl]methyl acetamide,
23) (S)-[N-3-(4-(2-(4-(2,6-dimethoxybenzoyl)piperazin-1-yl)pyrimidin-5-yl)-3-fluorophenyl)-2-oxo-5-oxazolidinyl]methyl acetamide,
24) (S)-[N-3-(4-(2-(4-(2-trifluoromethylbenzoyl) piperazin-1-yl)pyrimidin-5-yl)-3-fluorophenyl)-2-oxo-5-oxazolidinyl]methyl acetamide,
25) (S)-[N-3-(4-(2-(4-(4-trifluoromethylbenzoyl) piperazin-1-yl)pyrimidin-5-yl)-3-fluorophenyl)-2-oxo-5-oxazolidinyl]methyl acetamide,
26) (S)-[N-3-(4-(2-(4-phenylacetylpiperazin-1-yl) pyrimidin-5-yl)-3-fluorophenyl)-2-oxo-5-oxazolidinyl]methyl acetamide,
27) (S)-[N-3-(4-(2-(4-(3,5-dinitrobenzoyl)piperazin-1-yl) pyrimidin-5-yl)-3-fluorophenyl)-2-oxo-5-oxazolidinyl]methyl acetamide,
28) (S)-[N-3-(4-(2-(4-crotonylpiperazin-1-yl)pyrimidin-5-yl)-3-fluorophenyl)-2-oxo-5-oxazolidinyl]methyl acetamide,
29) (S)-[N-3-(4-(2-(4-trichloroacetylpiperazin-1-yl) pyrimidin-5-yl)-3-fluorophenyl)-2-oxo-5-oxazolidinyl]methyl acetamide,
30) (S)-[N-3-(4-(2-(4-n-valerylpiperazin-1-yl)pyrimidin-5-yl)-3-fluorophenyl)-2-oxo-5-oxazolidinyl]methyl acetamide,
31) (S)-[N-3-(4-(2-(4-(1-bromoethylcarbonyl)piperazin-1-yl)pyrimidin-5-yl)-3-fluorophenyl)-2-oxo-5-oxazolidinyl]methyl acetamide,
32) (S)-[N-3-(4-(2-(4-phenoxycarbonylpiperazin-1-yl) pyrimidin-5-yl)-3-fluorophenyl)-2-oxo-5-oxazolidinyl]methyl acetamide,
33) (S)-[N-3-(4-(2-(4-benzyloxycarbonylpiperazin-1-yl) pyrimidin-5-yl)-3-fluorophenyl)-2-oxo-5-oxazolidinyl]methyl acetamide,
34) (S)-[N-3-(4-(3-methoxycarbonylpyridin-5-yl)-3-fluorophenyl)-2-oxo-5-oxazolidinyl]methyl acetamide,
35) (S)-[N-3-(4-(2-acetylaminopyridin-5-yl)-3-fluorophenyl)-2-oxo-5-oxazolidinyl]methyl acetamide,
37) (S)-[N-3-(4-(2-hydroxyacetylaminopyridin-5-yl)-3-fluorophenyl)-2-oxo-5-oxazolidinyl]methyl acetamide,
38) (S)-[N-3-(4-(2-imidazol-1-yl-pyridin-5-yl)-3-fluorophenyl)-2-oxo-5-oxazolidinyl]methyl acetamide,
39) (S)-[N-3-(4-(2-morpholin-4-yl-pyridin-5-yl)-3-fluorophenyl)-2-oxo-5-oxazolidinyl]methyl acetamide,
40) (S)-[N-3-(4-(2-triphenylmethylaminopyridin-5-yl)-3-fluorophenyl)-2-oxo-5-oxazolidinyl]methyl acetamide,
41) (S)-[N-3-(4-(2-methoxyacetylaminopyridin-5-yl)-3-fluorophenyl)-2-oxo-5-oxazolidinyl]methyl acetamide,
42) (S)-[N-3-(4-(2-(4-triphenylmethylpiperazin-1-yl) pyridin-5-yl)-3-fluorophenyl)-2-oxo-5-oxazolidinyl] methyl acetamide,
43) (S)-[N-3-(4-(2-triphenylmethylaminopyridin-5-yl)-3-fluorophenyl)-2-oxo-5-oxazolidinyl]methyl acetamide,
44) (S)-[N-3-(4-(2-azidopyridin-5-yl)-3-fluorophenyl)-2-oxo-5-oxazolidinyl]methyl acetamide,
46) (S)-[N-3-(4-(2-methoxycarbonylpyridin-4-yl)-3-fluorophenyl)-2-oxo-5-oxazolidinyl]methyl acetamide,
47) (S)-[N-3-(4-(2-dimethylaminocarbonylpyridin-4-yl)-3-fluorophenyl)-2-oxo-5-oxazolidinyl]methyl acetamide,
48) (S)-[N-3-(4-(N-2-dimethylaminoacetoxyacetyl aminopyridin-4-yl)-3-fluorophenyl)-2-oxo-5-oxazolidinyl]methyl acetamide,
49) (S)-[N-3-(4-(2-hydroxyacetylaminopyridin-5-yl)-3-fluorophenyl)-2-oxo-5-oxazolidinyl]methyl acetamide,
50) (S)-[N-3-(4-(2-hydroxyacetylaminopyridin-5-yl)-3-fluorophenyl)-2-oxo-5-oxazolidinyl]methyl acetamide-hydroxypropylmethyl cellulose (HPMC, hydroxypropylmethyl cellulose),
51) (S)-[N-3-(4-(2-acetoxypyridin-5-yl)-3-fluorophenyl)-2-oxo-5-oxazolidinyl]methyl acetamide,
52) (S)-[N-3-(4-(2-methoxymethyloxypyridin-5-yl)-3-fluorophenyl)-2-oxo-5-oxazolidinyl]methyl acetamide,
54) (S)-[N-3-(4-(2-aminocarbonylpyridin-4-yl)-3-fluorophenyl)-2-oxo-5-oxazolidinyl]methyl acetamide,
56) (S)-[N-3-(4-(2-(2-hydroxyethyl)aminocarbonyl pyridin-4-yl)-3-fluorophenyl)-2-oxo-5-oxazolidinyl] methyl acetamide,
57) (S)-[N-3-(4-(2-N,N-di(2-hydroxyethyl)amino carbonylpyridin-4-yl)-3-fluorophenyl)-2-oxo-5-oxazolidinyl]methyl acetamide,
58) (S)-[N-3-(4-(2-piperazin-1-ylpyridin-5-yl)-3-fluorophenyl)-2-oxo-5-oxazolidinyl]methyl acetamide,
59) (S)-[N-3-(4-(2-(4-acetoxyacetylpiperazin-1-yl) pyridin-5-yl)-3-fluorophenyl)-2-oxo-5-oxazolidinyl] methyl acetamide,
60) (S)-[N-3-(4-(2-(4-benzyloxyacetylpiperazin-1-yl) pyridin-5-yl)-3-fluorophenyl)-2-oxo-5-oxazolidinyl] methyl acetamide,
61) (S)-[N-3-(4-(2-(4-hydroxyacetylpiperazin-1-yl) pyridin-5-yl)-3-fluorophenyl)-2-oxo-5-oxazolidinyl] methyl acetamide,
62) (S)-[N-3-(4-(2-(4-dimethylaminoacetoxyacetyl piperazin-1-yl)pyridin-5-yl)-3-fluorophenyl)-2-oxo-5-oxazolidinyl]methyl acetamide,
63) (S)-[N-3-(4-(2-(4-chloroacetylpiperazin-1-yl)pyridin-5-yl)-3-fluorophenyl)-2-oxo-5-oxazolidinyl]methyl acetamide,
64) (S)-[N-3-(4-(2-(4-acetylpiperazin-1-yl)pyridin-5-yl)-3-fluorophenyl)-2-oxo-5-oxazolidinyl]methyl acetamide,
65) (S)-[N-3-(4-(2-(4-methoxyacetylpiperazin-1-yl) pyridin-5-yl)-3-fluorophenyl)-2-oxo-5-oxazolidinyl] methyl acetamide,
66) (S)-[N-3-(4-(2-(4-morpholinylacetylpiperazin-1-yl) pyridin-5-yl)-3-fluorophenyl)-2-oxo-5-oxazolidinyl] methyl acetamide,
67) (S)-[N-3-(4-(2-(4-methoxycarbonylmethylamino acetylpiperazin-1-yl)pyridin-5-yl)-3-fluorophenyl)-2-oxo-5-oxazolidinyl]methyl acetamide, 68) (S)-[N-3-(4-(2-(4-ethoxycarbonylpiperidin-1-yl)pyridin-5-yl)-3-fuorophenyl)-2-oxo-5-oxazolidinyl]methyl acetamide,
69) (S)-[N-3-(4-(2-azidomethylpyridin-4-yl)-3-fluorophenyl)-2-oxo-5-oxazolidinyl]methyl acetamide,
70) (S)-[N-3-(4-(2-imidazol-1-yl)methylpyridin-4-yl)-3-fluorophenyl]-2-oxo-5-oxazolidinyl]methyl acetamide,
71) (S)-[N-3-(4-(2-morpholin-4-yl)methylpyridin-4-yl)-3-fluorophenyl]-2-oxo-5-oxazolidinyl]methyl acetamide,
72) (S)-[N-3-(4-(2-acetylthiomethylpyridin-4-yl)-3-fluorophenyl)-2-oxo-5-oxazolidinyl]methyl acetamide,
73) (S)-[N-3-(4-(2-mercaptomethylpyridin-4-yl)-3-fluorophenyl)-2-oxo-5-oxazolidinyl]methyl acetamide,
74) (S)-[N-3-(4-(2-(4-methanesulfonyloxyacetyl piperazin-1-yl)pyridin-5-yl)-3-fluorophenyl)-2-oxo-5-oxazolidinyl]methyl acetamide,
75) (S)-[N-3-(4-(2-(4-acryloylpiperazin-1-yl)pyridin-5-yl)-3-fluorophenyl)-2-oxo-5-oxazolidinyl]methyl acetamide,
76) (S)-[N-3-(4-(2-(4-ethoxyoxoacetylpiperazin-1-yl)pyridin-5-yl)-3-fluorophenyl)-2-oxo-5-oxazolidinyl]methyl acetamide,
77) (S)-[N-3-(4-(2-(4-nicotinoylpiperazin-1-yl)pyridin-5-yl)-3-fluorophenyl)-2-oxo-5-oxazolidinyl]methyl acetamide,
78) (S)-[N-3-(4-(2-(4-pivaloylpiperazin-1-yl)pyridin-5-yl)-3-fluorophenyl)-2-oxo-5-oxazolidinyl]methyl acetamide,
79) (S)-[N-3-(4-(2-(4-tetrabutylacetylpiperazin-1-yl)pyridin-5-yl)-3-fluorophenyl)-2-oxo-5-oxazolidinyl]methyl acetamide,
80) (S)-[N-3-(4-(2-(4-nicotinoyloxyacetylpiperazin-1-yl)pyridin-5-yl)-3-fluorophenyl)-2-oxo-5-oxazolidinyl]methyl acetamide,
81) (S)-[N-3-(4-(2-(4-(2,5-dimethoxyphenylacetyl)piperazin-1-yl)pyridin-5-yl)-3-fluorophenyl)-2-oxo-5-oxazolidinyl]methyl acetamide,
82) (S)-[N-3-(4-(2-(4-(3,3-dimethylacryloyl)piperazin-1-yl)pyridin-5-yl)-3-fluorophenyl)-2-oxo-5-oxazolidinyl]methyl acetamide,
83) (S)-[N-3-(4-(2-(4-(2,6-dimethoxybenzoyl)piperazin-1-yl)pyridin-5-yl)-3-fluorophenyl)-2-oxo-5-oxazolidinyl]methyl acetamide,
84) (S)-[N-3-(4-(2-(4-(2-trifluoromethyl)benzoyl)piperazin-1-yl)pyridin-5-yl)-3-fluorophenyl]-2-oxo-5-oxazolidinyl]methyl acetamide,
85) (S)-[N-3-(4-(2-(4-(4-trifluoromethyl)benzoyl)piperazin-1-yl)pyridin-5-yl)-3-fluorophenyl]-2-oxo-5-oxazolidinyl]methyl acetamide,
86) (S)-[N-3-(4-(2-(4-benzylcarbonylpiperazin-1-yl)pyridin-5-yl)-3-fluorophenyl)-2-oxo-5-oxazolidinyl]methyl acetamide,
87) (S)-[N-3-(4-(2-(4-crotonylpiperazin-1-yl)pyridin-5-yl)-3-fluorophenyl)-2-oxo-5-oxazolidinyl]methyl acetamide,
88) (S)-[N-3-(4-(2-(4-trifluoromethylcarbonyl piperazin-1-yl)pyridin-5-yl)-3-fluorophenyl)-2-oxo-5-oxazolidinyl]methyl acetamide,
89) (S)-[N-3-(4-(2-(4-n-valerylpiperazin-1-yl)pyridin-5-yl)-3-fluorophenyl)-2-oxo-5-oxazolidinyl]methyl acetamide,
90) (S)-[N-3-(4-(2-(4-phenyloxycarbonylpiperazin-1-yl)pyridin-5-yl)-3-fluorophenyl)-2-oxo-5-oxazolidinyl]methyl acetamide,
91) (S)-[N-3-(4-(2-(4-allyloxycarbonylpiperazin-1-yl)pyridin-5-yl)-3-fluorophenyl)-2-oxo-5-xazolidinyl]methyl acetamide,
92) (S)-[N-3-(4-(2-(4-(1-chloroethyl)oxycarbonyl piperazin-1-yl)pyridin-5-yl)-3-fluorophenyl)-2-oxo-5-oxazolidinyl]methyl acetamide,
93) (S)-[N-3-(4-(2-(4-(4-nitrobenzyl)oxycarbonyl piperazin-1-yl)pyridin-5-yl)-3-fluorophenyl)-2-oxo-5-oxazolidinyl]methyl acetamide,
94) (S)-[N-3-(4-(2-(4-benzyloxycarbonylpiperazin-1-yl)pyridin-5-yl)-3-fluorophenyl)-2-oxo-5-oxazolidinyl]methyl acetamide,
95) (S)-[N-3-(4-(2-(4-(9-fluorenylmethyloxycarbonyl)piperazin-1-yl)pyridin-5-yl)-3-fluorophenyl)-2-oxo-5-oxazolidinyl]methyl acetamide,
96) (S)-[N-3-(4-(2-(4-(2-pyrimidinyl)piperazin-1-yl)pyridin-5-yl)-3-fluorophenyl)-2-oxo-5-oxazolidinyl]methyl acetamide,
97) (S)-[N-3-(4-(2-(4-methoxycarbonylmethylpiperazin-1-yl)pyridin-5-yl)-3-fluorophenyl)-2-oxo-5-oxazolidinyl]methyl acetamide,
98) (S)-[N-3-(4-(2-fluoromethylpyridin-4-yl)-3-fluorophenyl)-2-oxo-5-oxazolidinyl]methyl acetamide,
99) (S)-[N-3-(4-(2-cyanomethylpyridin-4-yl)-3-fluorophenyl)-2-oxo-5-oxazolidinyl]methyl acetamide,
100) (S)-[N-3-(4-(2-(4-(2-hydroxy)ethylpiperazin-1-yl)pyridin-5-yl)-3-fluorophenyl)-2-oxo-5-oxazolidinyl]methyl acetamide,
101) (S)-[N-3-(4-(2-(4-(2-acetoxy)ethylpiperazin-1-yl)pyridin-5-yl)-3-fluorophenyl)-2-oxo-5-oxazolidinyl]methyl acetamide,
102) (S)-[N-3-(4-(2-(4-methoxycarbonylpiperazin-1-yl)pyridin-5-yl)-3-fluorophenyl)-2-oxo-5-oxazolidinyl]methyl acetamide,
103) (S)-[N-3-(4-(2-(4-(2-methanesulfonyloxy)ethylpiperazin-1-yl)pyridin-5-yl)-3-fluorophenyl)-2-oxo-5-oxazolidinyl]methyl acetamide,
104) (S)-[N-3-(4-(2-(4-hydroxymethyl)imidazol-1-yl)pyridin-5-yl)-3-fluorophenyl]-2-oxo-5-oxazolidinyl]methyl acetamide,
105) (S)-[N-3-(4-(2-aminoacetylaminopyridin-5-yl)-3-fluorophenyl)-2-oxo-5-oxazolidinyl]methyl acetamide,
106) (S)-[N-3-(4-(2-(4-cyanopiperazin-1-yl)pyridin-5-yl)-3-fluorophenyl)-2-oxo-5-oxazolidinyl]methyl acetamide,
107) (S)-[N-3-(4-(2-(4-carboxamideoximpiperazin-1-yl)pyridin-5-yl)-3-fluorophenyl)-2-oxo-5-oxazolidinyl]methyl acetamide,
109) (S)-[N-3-(4-(2-azidoacetylaminopyridin-5-yl)-3-fluorophenyl)-2-oxo-5-oxazolidinyl]methyl acetamide,
110) (S)-[N-3-(4-(2-(1,2,3,4,6,7-hexahydro-5-oxo-1,4-diazepan-1-yl)-pyridin-5-yl)-3-fluorophenyl)-2-oxo-5-oxazolidinyl]methyl acetamide,
111) (S)-[N-3-(4-(2-N-(dimethylaminomethylene)aminopyridin-5-yl)-3-fluorophenyl)-2-oxo-5-oxazolidinyl]methyl acetamide,
112) (S)-[N-3-(4-(2-(4-hydroxyiminopiperidin-1-yl)pyridin-5-yl)-3-fluorophenyl)-2-oxo-5-oxazolidinyl]methyl acetamide,
113) (S)-[N-3-(4-(2-(4-methanesulfonyloxyiminopiperidin-1-yl)pyridin-5-yl)-3-fluorophenyl)-2-oxo-5-oxazolidinyl]methyl acetamide, 114) (S)-[N-3-(4-(2-(4-methyliminopiperidin-1-yl)pyridin-5-yl)-3-fluorophenyl)-2-oxo-5-oxazolidinyl]methyl acetamide,
115) (S)-[N-3-(4-(2-(4-methoxycarbonylhydrazinopiperidin-1-yl)pyridin-5-yl)-3-fluorophenyl)-2-oxo-5-oxazolidinyl]methyl acetamide,
116) (S)-[N-3-(4-(2-N-(L-alanyl)aminopyridin-5-yl)-3-fluorophenyl)-2-oxo-5-oxazolidinyl]methyl acetamide,
117) (S)-[N-3-(4-(2-acetylaminoacetylaminopyridin-5-yl)-3-fluorophenyl)-2-oxo-5-oxazolidinyl]methyl acetamide,
118) (S)-[N-3-(4-(2-dimethylaminoacetylaminopyridin-5-yl)-3-fluorophenyl)-2-oxo-5-oxazolidinyl]methyl acetamide,
119) (S)-[N-3-(4-(2-nicotinoylaminopyridin-5-yl)-3-fluorophenyl)-2-oxo-5-oxazolidinyl]methyl acetamide,
120) (S)-[N-3-(4-(2-(1,2,4-triazol-1-yl)pyridin-5-yl)-3-fluorophenyl)-2-oxo-5-oxazolidinyl]methyl acetamide,
121) (S)-[N-3-(4-(2-(4-hydroxypiperidin-1-yl)pyridin-5-yl)-3-fluorophenyl)-2-oxo-5-oxazolidinyl]methyl acetamide,
122) (S)-[N-3-(4-(2-N,N-(hydroxyacetyl)methylaminopyridin-5-yl)-3-fluorophenyl)-2-oxo-5-oxazolidinyl]methyl acetamide,
123) (S)-[N-3-(4-(2-(4-methylimidazol-1-yl)pyridin-5-yl)-3-fluorophenyl)-2-oxo-5-oxazolidinyl]methyl acetamide,
124) (S)-[N-3-(4-(2-(2-hydroxypropionyl)aminopyridin-5-yl)-3-fluorophenyl)-2-oxo-5-oxazolidinyl]methyl acetamide,
125) (S)-[N-3-(4-(2-(3-amino-1,2,4-triazol-1-yl)pyridin-5-yl)-3-fluorophenyl)-2-oxo-5-oxazolidinyl]methyl acetamide,
126) (S)-[N-3-(4-(2-(4-ethoxycarbonylimidazol-1-yl)pyridin-5-yl)-3-fluorophenyl)-2-oxo-5-oxazolidinyl]methyl acetamide,
127) (S)-(N-3-(4-(2-(1-tetrazolyl)-pyridin-5-yl)-3-fluorophenyl)-2-oxo-5-oxazolidinyl) methyl acetamide,
128) (S)-[N-3-(4-(2-(5-methyl-(1,3,4)-oxadiazol-2-yl)pyridin-5-yl)-3-fluorophenyl)-2-oxo-5-oxazolidinyl]methyl acetamide,
129) (S)-[N-3-(4-(2-(5-methyl-(1,2,4)-oxadiazol-3-yl)pyridin-5-yl)-3-fluorophenyl)-2-oxo-5-oxazolidinyl]methyl acetamide,
130) (S)-[N-3-(4-(2-(1-methyl-5-tetrazolyl)-pyridin-5-yl)-3-fluorophenyl)-2-oxo-5-oxazolidinyl]methyl acetamide,
131) (S)-[N-3-(4-(2-(2-methyl-5-tetrazolyl)-pyridin-5-yl)-3-fluorophenyl)-2-oxo-5-oxazolidinyl]methyl acetamide,
132) (S)-[N-3-(4-(2-(4-ethoxycarbonyl-(1,2,3)-triazol-1-yl)-5-pyridinyl)-3-fluorophenyl)-2-oxo-5-oxazolidinyl]methyl acetamide,
133) (S)-[N-3-(4-(2-(3-pyrrolynyl)-5-pyridinyl)-3-fluorophenyl)-2-oxo-5-oxazolidinyl]methyl acetamide,
134) (S)-[N-3-(4-(2-(2-oxo-(1,3)-oxazolidin-3-yl)-pyridin-5-yl)-3-fluorophenyl)-2-oxo-5-oxazolidinyl]methyl acetamide,
135) (S)-[N-3-(4-(2-((1,3)-oxazol-5-yl)-pyridin-5-yl)-3-fluorophenyl)-2-oxo-5-oxazolidinyl]methyl acetamide,
136) (S)-[N-3-(4-(2-((1,2,4)-oxadiazol-3-yl)-pyridin-5-yl)-3-fluorophenyl)-2-oxo-5-oxazolidinyl]methyl acetamide,
137) (S)-[N-3-(4-(2-((1,2,3)-triazol-1-yl)-pyridin-5-yl)-3-fluorophenyl)-2-oxo-5-oxazolidinyl]methyl acetamide,
138) (S)-[N-3-(4-(2-(3-methyl-2-oxo-2,3-dihydro-(1,3,4)-triazol-1-yl)-5-pyridinyl)-3-fluorophenyl)-2-oxo-5-oxazolidinyl]methyl acetamide,
139) (S)-[N-3-(4-(2-(2-oxo-(1,3)-imidazolidin-1-yl)-pyridin-5-yl)-3-fluorophenyl)-2-oxo-5-oxazolidinyl]methyl acetamide,
140) (S)-[N-3-(4-(2-(4-hydroxy-piperidin-1-yl)-5-pyridinyl)-3-fluorophenyl)-2-oxo-5-oxazolidinyl]methyl acetamide,
141) (S)-[N-3-(4-(2-(2-oxo-(2,3)-dihydro-(1,3,4)-triazol-1-yl)-5-pyridinyl)-3-fluorophenyl)-2-oxo-5-oxazolidinyl]methyl acetamide,
142) (S)-[N-3-(4-(2-(5-hydroxymethyl-(1,2,4)-oxadiazol-3-yl)-5-pyridinyl)-3-fluorophenyl)-2-oxo-5-oxazolidinyl]methyl acetamide,
143) (S)-[N-3-(4-(2-(5-tetrazolyl)-5-pyridinyl)-3-fluorophenyl)-2-oxo-5-oxazolidinyl]methyl acetamide,
144) (S)-[N-3-(4-(2-(5-methoxymethyl-(1,2,4)-oxadiazol-3-yl)-5-pyridinyl)-3-fluorophenyl)-2-oxo-5-oxazolidinyl]methyl acetamide,
145) (S)-[N-3-(4-(2-(5-trichloromethyl-(1,2,4)-oxadiazol-3-yl)-5-pyridinyl)-3-fluorophenyl)-2-oxo-5-oxazolidinyl]methyl acetamide,
146) (S)-[N-3-(4-(2-(5-dimethylamino-(1,2,4)-oxadiazol-3-yl)-5-pyridinyl)-3-fluorophenyl)-2-oxo-5-oxazolidinyl]methyl acetamide,
147) (S)-[N-3-(4-(2-(5-amino-(1,2,4)-oxadiazol-3-yl)-pyridin-5-yl)-3-fluorophenyl)-2-oxo-5-oxazolidinyl]methyl acetamide,
148) (S)-[N-3-(4-(2-(4-acetylamino-1-piperidinyl)-pyridin-5-yl)-3-fluorophenyl)-2-oxo-5-oxazolidinyl]methyl acetamide,
149) (S)-[N-3-(4-(2-(4-acetyloxymethylcarbonylamino-piperidin-1-yl)-pyridin-5-yl)-3-fluorophenyl)-2-oxo-5-oxazolidinyl]methyl acetamide,
150) (S)-[N-3-(4-(2-(4-hydroxymethylcarbonylamino-piperidin-1-yl)-pyridin-5-yl)-3-fluorophenyl)-2-oxo-5-oxazolidinyl]methyl acetamide, and
151) (S)-[N-3-(4-(2-(3,4-dihydroxy-pyrrolidin-1-yl)-pyridin-5-yl)-3-fluorophenyl)-2-oxo-5-oxazolidinyl]methyl acetamide.

3. The oxazoline derivatives according to claim 1, wherein the derivatives are selected from the group consisted of;
1) (S)-[N-3-(4-(2-(1,2,4-triazol-1-yl)pyridin-5-yl)-3-fluorophenyl)-2-oxo-5-oxazolidinyl]methyl acetamide,
2) (S)-[N-3-(4-(2-(5-methyl-(1,3,4)-oxadiazol-2-yl)-pyridin-5-yl)3-fluorophenyl)-2-oxo-5-oxazolidinyl]methyl acetamide,
3) (S)-[N-3-(4-(2-(5-methyl-1,2,4-oxadiazol-3-yl)-pyridin-5-yl)-3-fluorophenyl)-2-oxo-5-oxazolidinyl]methyl acetamide,
4) (S)-[N-3-(4-(2-(1-methyl-5-tetrazolyl)-pyridin-5-yl)-3-fluorophenyl)-2-oxo-5-oxazolidinyl]methyl acetamide, and
5) (S)-[N-3-(4-(2-oxo-(1,3)-oxazolidin-3-yl)-pyridin-5-yl)-3-fluorophenyl]-2-oxo-5-oxazolidinyl]methyl acetamide.

4. A method for preparing an oxazolidinone derivative of formula 1 of claim 1, comprising the step of reacting a trimethylstannyl oxazolidinone derivative of formula 2 with a pyridine or pyrimidine derivative of formula 3, in the presence of a palladium catalyst,

Scheme 1

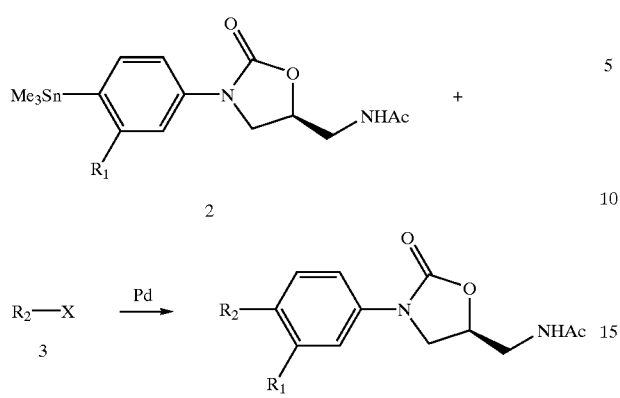

wherein, $R_1$, $R_2$ and X are each as defined above.

5. The method according to claim 2, comprising the steps of:
   a) aminating a hydroxymethyloxazolidinone derivative of formula 4, at its hydroxy group to give an amine compound of formula 5 (step 1);
   b) acetylating the amine compound of formula 5 by use of acetic anhydride to produce an acetyl compound of formula 6 (step 2);
   c) halogenating the acetyl compound of formula 6 at its phenyl ring to produce a halogen compound of formula 7 (step 3);
   d) stannylating the halogen compound of formula 7 in the presence of a palladium catalyst to give a trimethylstannyl oxazolidinone derivative of formula 2 (step 4); and
   e) substituting the trimetylstannyl group of the oxazolidinone derivative of formula 2 with a pyridine or pyrimidine moiety in the presence of a palladium catalyst to yield a compound of formula 1 (step 5),

Scheme 2

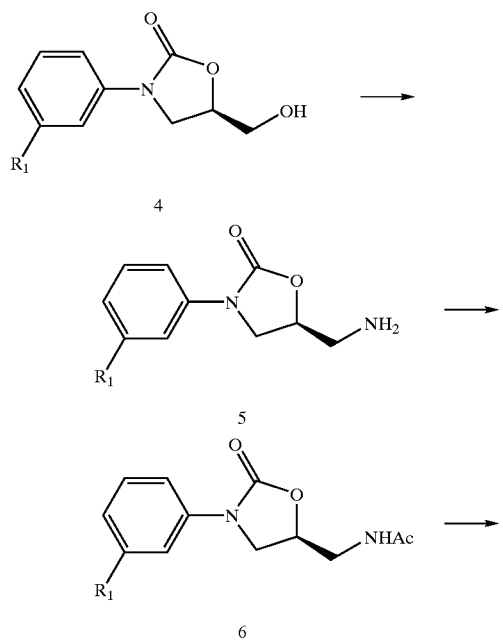

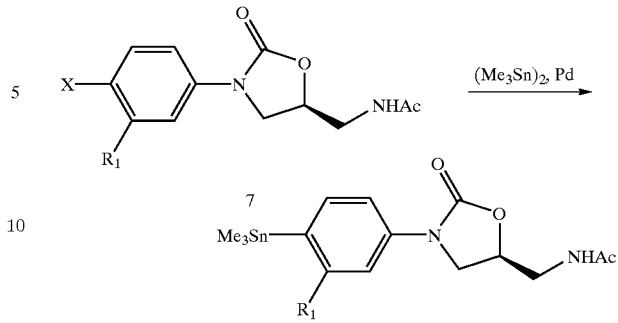

wherein $R_1$ and $R_2$ are as defined above, and X is a halogen atom.

6. A method for preparing an oxazolidinone derivative of formula 1 of claim 1, comprising the steps of:
   a) reacting the trimethylstannyl oxazolidinone derivative of formula 2 with a cyanopyridine derivative to synthesize an intermediate of formula 13;
   b) iminating the compound of formula 13 with hydroxyl amine to give the corresponding imine compound of formula 14; and
   c) cyclizing the imine compound of formula 14 with a carboxylic acid derivative,

Scheme 5

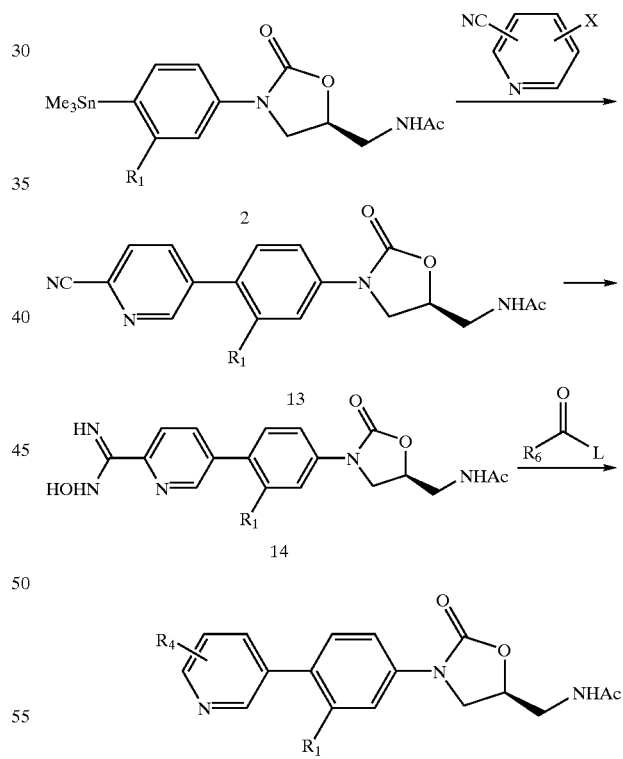

wherein $R_1$, $R_2$, $R_6$ and X are each as defined above, and L is a typical leaving group.

7. A pharmaceutical composition suitable for use in antibiotics, comprising the oxazolidinone derivative or its pharmaceutically acceptable salt of claim 1 as an effective ingredient.

* * * * *